(12) United States Patent
Ross et al.

(10) Patent No.: US 10,377,711 B2
(45) Date of Patent: Aug. 13, 2019

(54) CANNABINOID TYPE 1 RECEPTOR MODULATORS

(71) Applicants: The Governing Council of the University of Toronto, Toronto (CA); The University Court of the University of Aberdeen, Aberdeen (GB)

(72) Inventors: Ruth Ross, Toronto (CA); Iain Greig, Aberdeen (GB); Matteo Zanda, Aberdeen (GB); Chih-Chung Tseng, Aberdeen (GB)

(73) Assignees: The University Court of the University of Aberdeen, Aberdeen (GB); The Governing Council of the University of Toronto, Toronto (CA)

( * ) Notice: Subject to any disclaimer, the term of this patent is extended or adjusted under 35 U.S.C. 154(b) by 17 days.

(21) Appl. No.: 15/507,079

(22) PCT Filed: Aug. 26, 2015

(86) PCT No.: PCT/CA2015/050815
§ 371 (c)(1),
(2) Date: Feb. 27, 2017

(87) PCT Pub. No.: WO2016/029310
PCT Pub. Date: Mar. 3, 2016

(65) Prior Publication Data
US 2018/0118681 A1    May 3, 2018

Related U.S. Application Data

(60) Provisional application No. 62/042,361, filed on Aug. 27, 2014.

(51) Int. Cl.
| | |
|---|---|
| *C07D 209/10* | (2006.01) |
| *C07D 209/12* | (2006.01) |
| *C07D 401/04* | (2006.01) |
| *C07D 405/06* | (2006.01) |
| *C07D 409/06* | (2006.01) |
| *C07D 209/14* | (2006.01) |
| *A61P 25/14* | (2006.01) |
| *A61P 25/34* | (2006.01) |
| *A61P 27/02* | (2006.01) |
| *A61P 17/06* | (2006.01) |
| *A61P 27/06* | (2006.01) |
| *A61P 9/10* | (2006.01) |
| *A61P 19/00* | (2006.01) |
| *A61P 25/28* | (2006.01) |
| *A61P 25/30* | (2006.01) |
| *A61P 43/00* | (2006.01) |
| *A61P 1/16* | (2006.01) |
| *A61P 9/00* | (2006.01) |
| *A61P 11/06* | (2006.01) |
| *A61P 25/22* | (2006.01) |

(Continued)

(52) U.S. Cl.
CPC .............. *C07D 209/14* (2013.01); *A61P 1/00* (2018.01); *A61P 1/08* (2018.01); *A61P 1/16* (2018.01); *A61P 9/00* (2018.01); *A61P 9/10* (2018.01); *A61P 9/12* (2018.01); *A61P 11/06* (2018.01); *A61P 13/12* (2018.01); *A61P 17/06* (2018.01); *A61P 19/00* (2018.01); *A61P 19/02* (2018.01); *A61P 19/08* (2018.01); *A61P 19/10* (2018.01); *A61P 25/00* (2018.01); *A61P 25/08* (2018.01); *A61P 25/14* (2018.01); *A61P 25/16* (2018.01); *A61P 25/18* (2018.01); *A61P 25/22* (2018.01); *A61P 25/24* (2018.01); *A61P 25/28* (2018.01); *A61P 25/30* (2018.01); *A61P 25/32* (2018.01); *A61P 25/34* (2018.01); *A61P 27/02* (2018.01); *A61P 27/06* (2018.01); *A61P 29/00* (2018.01); *A61P 35/00* (2018.01); *A61P 43/00* (2018.01); *C07D 209/10* (2013.01); *C07D 209/12* (2013.01); *C07D 401/04* (2013.01); *C07D 405/06* (2013.01); *C07D 409/06* (2013.01)

(58) Field of Classification Search
CPC .. C07D 209/10; C07D 209/12; C07D 401/04; C07D 405/06; C07D 409/06
See application file for complete search history.

(56) References Cited

FOREIGN PATENT DOCUMENTS

| WO | WO 2013/103967 | * | 7/2013 |
|---|---|---|---|
| WO | WO-2013103967 | | 7/2013 |
| WO | WO-2016029310 | | 3/2016 |

OTHER PUBLICATIONS

Lancianesi (Adv. Synth. Catal. 2012, 354, 3539-3544).*

(Continued)

*Primary Examiner* — Valerie Rodriguez-Garcia
(74) *Attorney, Agent, or Firm* — Schwegman Lundberg & Woessner, P.A.

(57) ABSTRACT

The present disclosure relates to indole derivatives of the formula (I) which are cannabinoid type 1 receptor modulators and which are useful in the treatment of diseases in which modulation of the receptor is beneficial; to processes for their preparation; to pharmaceutical compositions comprising them; and to methods of using them.

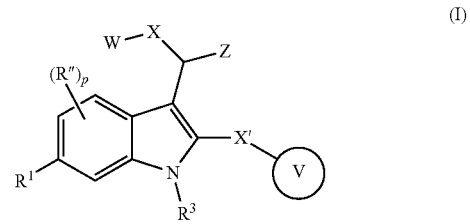

(I)

15 Claims, No Drawings

(51) Int. Cl.
| | |
|---|---|
| A61P 25/32 | (2006.01) |
| A61P 19/02 | (2006.01) |
| A61P 9/12 | (2006.01) |
| A61P 13/12 | (2006.01) |
| A61P 25/18 | (2006.01) |
| A61P 25/24 | (2006.01) |
| A61P 1/00 | (2006.01) |
| A61P 19/08 | (2006.01) |
| A61P 25/00 | (2006.01) |
| A61P 25/08 | (2006.01) |
| A61P 25/16 | (2006.01) |
| A61P 29/00 | (2006.01) |
| A61P 1/08 | (2006.01) |
| A61P 19/10 | (2006.01) |
| A61P 35/00 | (2006.01) |

(56) References Cited

OTHER PUBLICATIONS

Ballini (Adv. Synth. Catal. 2008, 350, 129-134).*
"European Application No. 15836620.3, Extended European Search Report dated Jan. 31, 2018", (Jan. 31, 2018), 6 pgs.
Ballini, Roberto, et al., "Reaction of 3-(1-Arylsulfonylalkyl)-indoles with Easily Enolisable Derivatives Promoted by Potassium Fluoride on Basic Alumina", Adv. Synth. Catal., 2008, 350, 129-134, (Dec. 14, 2007), 129-134.
Adam, Julia M., et al., "Low brain penetrant CB1 receptor agonists for the treatment of neuropathic pain", Bioorganic & Medicinal Chemistry Letters 22 (2012) 2932-2937, (Feb. 23, 2012), 2932-2937.
Adam, Lynda, et al., "Positive allosteric modulators of CB1 receptors", Symposium on the Cannabinoids. Burlington, Vermont, USA. International Cannabinoid Research Society, p. 86, (2007), 1 pg.
Baell, Jonathan B., et al., "New Substructure Filters for Removal of Pan Assay Interference Compounds (PAINS) from Screening Libraries and for Their Exclusion in Bioassays", J. Med. Chem. 2010, 53, 2719-2740, (Feb. 4, 20102010), 2719-2740.
Cravatt, Benjamin F., et al., "The Endogenous Cannabinoid System and Its Role in Nociceptive Behavior", J. Neurobiol., vol. 61, pp. 149-160 (2004), (May 17, 2004), 149-160.
Crowe, Molly S., et al., "The endocannabinoid system modulates stress, emotionality, and inflammation", Brain, Behavior, and Immunity; Nov. 2014; 42:1-5, (Nov. 2014), 1-5.
Di Marzo, Vincenzo, "Targeting the endocannabinoid system: to enhance or reduce?", Nature Reviews, vol. 7, May 2008; 438-455, (May 2008), 438-455.

Gao, Zhan-Guo, et al., "Keynote review: Allosterism in membrane receptors", DDT • vol. 11, No. 5/6 • Mar. 2006, (Mar. 2006), 191-202.
Ignatowska-Jankowska, Bogna M., et al., "A Cannabinoid CB1 Receptor-Positive Allosteric Modulator Reduces Neuropathic Pain in the Mouse with No Psychoactive Effects", Neuropsychopharmacology (2015), 1-12, epub ahead of print Jun. 8, 2015, (2015), 1-12.
Ignatowska-Jankowska, Bogna M., et al., "In Vivo Effects of ZCZ011: A Positive Allosteric Modulator of the CB1 Receptor", 23rd Annual Symposium of the International Cannabinoid Reach Society, Vancouver, British Columbia, Canada, Jun. 21, 2013. (abstract p. 14)., (Jun. 21, 2013), 1 pg.
Kelly, T. Ross, et al., "Relative Binding Affinity of Carboxylate and Its Isosteres: Nitro, Phosphate, Phosphonate, Sulfonate, and d-Lactone", J. Am. Chem. Soc. 1994, 116, 7072-7080, (Feb. 2, 1994), 7072-7080.
Kunos, George, et al., "Should peripheral CB1 cannabinoid receptors be selectively targeted for therapeutic gain?", Trends Pharmacol Sci. Jan. 2009; 30(1): 1-7, (Jan. 2009), 1-7.
Meanwell, Nicholas A., et al., "Synopsis of Some Recent Tactical Application of Bioisosteres in Drug Design", J. Med. Chem. 2011, 54, 2529-2591, (Mar. 17, 2011), 2529-2591.
Mechoulam, Raphael, et al., "The Endocannabinoid System and the Brain", Annu. Rev. Psychol. 2013. 64:21-47, (Jul. 12, 2012), 21-47.
Noland, Wayland E., et al., "The Nitroethylation of Indoles. III.1-3 a Synthetic Route to Substituted Tryptamines", J. Amer. Chem. Soc., vol. 81, pp. 1203-1209, (Mar. 5, 2959), 1203-1209.
Parolaro, Daniela, "The endocannabinoid system and psychiatric disorders", Experimental Neurology 224 (2010) 3-14, (Mar. 29, 2010), 3-14.
Pertwee, Roger G., "Emerging strategies for exploiting cannabinoid receptor agonists as medicines", British Journal of Pharmacology (2009), 156, 397-411, (2009), 397-411.
Pertwee, Roger G., "Targeting the endocannabinoid system with cannabinoid receptor agonists: pharmacological strategies and therapeutic possibilities", Phil. Trans. R. Soc. B (2012) 367, 3353-3363, (2012), 3353-3363.
Price, Martin R., et al., "Allosteric Modulation of the Cannabinoid CB1 Receptor", Mol Pharmacol 68:1484-1495, 2005, (1484-1495), 2005.
Ross, Ruth A., et al., "Allosterism and cannabinoid CB1 receptors: the shape of things to come", TRENDS in Pharmacological Sciences vol. 28 No. 11, (Nov. 8, 2007), 567-572.
Soudijn, Willem, et al., "Allosteric modulation of G protein- coupled receptors: perspectives and recent developments", DDT vol. 9, No. 17 Sep. 2004, (Sep. 2004), 752-758.
"International Application No. PCT/CA2015/050815, International Search Report and Written Opinion dated Nov. 4, 2015", (Nov. 4, 2015), 11 pgs.

* cited by examiner

CANNABINOID TYPE 1 RECEPTOR MODULATORS

PRIORITY CLAIM TO RELATED APPLICATIONS

This application is a U.S. national stage application filed under 35 U.S.C. § 371 from International Application Ser. No. PCT/CA2015/050815, which was filed 26 Aug. 2015, and published as WO2016/029310 on 3 Mar. 2016, and which claims priority to United States Provisional Application No. 62/042,361, filed 27 Aug. 2014, which applications and publication are incorporated by reference as if reproduced herein and made a part hereof in their entirety, and the benefit of priority of each of which is claimed herein.

RELATED APPLICATIONS

This Patent Cooperation Treaty Application claims the benefit under 35 USC § 119(e) from U.S. Provisional Patent Application No. 62/042,361, filed on Aug. 27, 2014, which is incorporated by reference herein in its entirety.

FIELD

The present disclosure relates to compounds of the Formula (I) which are cannabinoid type 1 receptor modulators, and their use in the treatment of diseases in which modulation of the receptor is beneficial.

INTRODUCTION

The endocannabinoid system encompasses a family of endogenous eicosanoid ligands, known as "endocannabinoids". Prominent examples include arachidonoylethanolamide (anandamide) and 2-arachidonoyl glycerol (2-AG), both of which are synthesised on demand and are rapidly hydrolysed by the enzymes fatty acid amide hydrolase (FAAH) and monoacyl glycerol lipase (MAG lipase) respectively (see, e.g., Di Marzo, 2004). Levels of the endocannabinoids are altered in certain disease states, where they have an autoprotective role (see, e.g., Pertwee, 2005). Mammalian tissues express at least two types of cannabinoid receptor, CB1 and CB2, both G protein coupled receptors (GPCR).

Cannabinoid receptors have been shown to play an important role in many areas of human physiology and are treatments or potential treatments for a number of human medical conditions. Cannabinoid receptor agonists are already in use (e.g., Marinol®, Solvay; Nabilone®, Eli Lilly; Sativex®, GW Pharmaceuticals) as treatments for chemotherapy-induced nausea; for the control of pain and the treatment of spasticity in patients with multiple sclerosis; and as appetite enhancers for patients with HIV/AIDS or undergoing chemotherapy.

Other studies have demonstrated a role in inflammation for both the CB1 and CB2 receptors and the ability of drugs which antagonize these receptors to be used as anti-inflammatory agents in the treatment of a number of disorders, including rheumatoid arthritis, psoriasis and inflammatory bowel disease (see, e.g., Croci et al., 2003).

More recently there has been intense interest in the therapeutic properties of drugs which act as antagonists at CB1. These include SR141716A (Acomplia®, Sanofi-Aventis) and taranabant (Merck) for which clinical trials demonstrated efficacy in facilitation of weight loss, treatment of type-2 diabetes and cessation of smoking. Other studies have shown that similar compounds are able to prevent bone loss and therefore can used in the treatment of disorders involving excessive or inappropriate bone loss, including osteoporosis, Paget's disease of bone, and bone cancers (see, e.g., Greig et al., 2004; Idris et al., 2005).

However, some of these compounds have drawbacks which are caused both by down-regulation of the receptor (due to the property of inverse agonism) leading to a reduction in efficacy and reversal of weight loss on cessation of treatment, and the CNS effects, which included suicidal thought, nausea and depression.

It has been suggested that the toxicological issues associated with cannabinoid antagonism could be avoided if a drug tuned down excessive receptor activation, rather than turned it off completely. This effect can be achieved by the use of allosteric modulators and the therapeutic potential of cannabinoid receptor modulation harnessed without the associated side effects of global activation or inhibition of the receptor (see, e.g., Di Marzo, 2008).

Advantages of Allosteric Modulation of Receptors

It is now acknowledged that numerous GPCRs contain allosteric binding sites for endogenous and/or synthetic ligands, which are discrete from the agonist-binding site, which is known as the orthosteric site (the normal binding site for the endogenous ligand) (see, e.g., Christopoulos et al., 2002). The binding of an allosteric modulator delivers a conformational change which impacts the affinity and/or efficacy of orthosteric ligands, thereby influencing the behaviour of a receptor and tuning the pre-existing actions of the endogenous ligands (see, e.g., May et al., 2003). The action may increase or decrease the affinity of the endogenous ligand and its association or dissociation rate constant, and may either increase or decrease the intracellular signalling caused by the binding of the endogenous ligand. Thus, allosteric modulators may be defined as positive or negative according to whether they enhance or inhibit the transmission of signalling caused by the endogenous ligand binding.

Allosteric modulators (acting at a site away from that which binds the normal ligand) play an increasingly prominent role in therapeutics, and are recognized particularly as a promising approach to achieving receptor selectivity.

Allosteric modulation has a number of advantages, including more subtle modulation or resetting of receptor activity than seen with intervention at the orthosteric site. As an allosteric modulator can only act in the presence of the natural ligand, it allows for drug therapy that more effectively maintains normal receptor function. That is, many synthetic drugs will remain bound to the receptor for a lengthy period, or have been designed to have improved metabolic stability (as required to reach the site of activity), thus causing an extended effect and either desensitization or continued and excessive activation of the receptor. On the other hand, the endogenous ligand is often rapidly broken down or recycled, causing only a transient activation or deactivation and thus avoiding such changes as receptor expression levels. Thus, allosteric modulation may be less likely to cause side-effects, as the pharmacological effects more closely model normal physiology. (See, e.g., Conn et al, 2009; Gao et al., 2006).

Furthermore, the endogenous ligand is generally synthesized and released on demand at the site in which the action is required; rapid breakdown ensures that the effects on distant receptors sites in other tissue types is kept to a minimum. Likewise, in disease states, receptor over-activation or under-activation may be restricted to particular tissues and it is desirable only to modulate at these sites; altering receptor activity at other sites may lead in turn to undesirable harmful effects. Synthetic ligands tend to be delivered systemically and thus affect a variety of tissue types, but cannot usually be designed to have the same binding characteristics as the endogenous ligand, due to the requirements for metabolic and chemical stability. Thus, tuning of the signal from the endogenous ligand also has the advantage of introducing tissue selectivity and thus affecting only the tissues affected by the disease state, giving a more effective therapy.

Furthermore, with less evolutionary pressure and lower sequence conservation between receptor sub-types, the allosteric sites of many receptors offer greater opportunities for selectivity, whereas the orthosteric sites of many receptors can be too similar to allow a drug to distinguish between them (as they often must bind the same endogenous ligand, e.g., a neurotransmitter). An example of this has been the development of sub-type specific muscarinic acetylcholine receptor (M) and metabotropic glutamate receptor (mGluR) allosteric modulators, following repeated failure to achieve selectivity with orthosteric modulators. General reviews on the growing importance and promise of allosteric modulation can be found in, e.g., Conn et al., 2009. Reviews regarding the potential of cannabinoids can be found in, e.g., Ross, 2007.

Furthermore, allosteric modulation may offer an approach to targeting the activities of orthosteric receptors which are regarded as "un-druggable", in that the physiochemical characteristics of the binding site (the mixture of hydrophobic and polar groups lining the pocket) may be incompatible with the physicochemical attributes required of a drug with sufficient solubility, membrane permeability and metabolic stability to reach the site of action. In these cases, an allosteric site may be found which has better compatibility with drug-like substances.

Furthermore, allosteric modulation may offer an approach to targeting diseases in which receptor number has been reduced (e.g., Parkinson's disease, in which the number of dopaminergic neurons is diminished).

A number of receptors have been shown to be amenable to positive or negative allosteric modulation by small molecules, including the GABA (against which diazepam acts), adenosine, muscarinic and metabotropic glutamate receptors (see, e.g., Soudijn et al, 2004; Gao et al., 2006).

Recent reviews highlight the potential of developing positive and negative allosteric modulators of GPCRs (see, e.g., Wang et al., 2009). Similarly, there are key advantages in targeting drugs to allosteric sites on the cannabinoid CB1 receptor: reduced side-effect profile; greater receptor-subtype selectivity; reduced drug-induced alterations in receptor coupling mechanisms (see, e.g., Ross, 2007). In particular, allosteric modulators possess specific advantages when considering the treatment of multi-factorial syndromes, such as metabolic disorders (see, e.g., Wang et al., 2009).

In 2005, the first evidence was published indicating that the cannabinoid CB1 receptor contains an allosteric binding site and compounds were identified that unexpectedly are allosteric enhancers of agonist binding affinity, but are functionally allosteric inhibitors of agonist signalling efficacy (see, e.g., Price et al., 2005). Allosteric enhancers have the potential to treat anxiety, depression, multiple sclerosis, pain and other disorders in which cannabinoid activation has been shown to play a beneficial role; enhancers would lessen psychoactive side-effects associated with direct agonism of CB1. Allosteric inhibitors have the potential to treat metabolic syndrome (obesity, type-2 diabetes and associated conditions), drug addiction and other conditions in which excessive activation of the cannabinoid system has been implicated.

Cannabinoid Allosteric Modulators and Greater Receptor-Subtype Selectivity

Generating receptor ligands with high subtype-selectivity is often hampered by the large extent of sequence homology within the orthosteric binding domain across receptor subtypes (see, e.g., Rees, 2002). Whilst a number of ligands that are selective for the cannabinoid CB1 and CB2 receptor have been developed to date, issues of receptor subtype selectivity remain. A number of well-established cannabinoid receptor agonists and antagonists have affinity for an orphan receptor GPR55 and the TRPV1 channel (see, e.g., Ryberg et al., 2007; Ross, 2003).

Allosteric Modulators and Reduced Side-Effect Profile

There is ample evidence that the levels of endocannabinoids are increased in both physiological and pathophysiological situations, in which an autoprotective action of the endocannabinoids has been also implicated (see, e.g., Pertwee, 2005).

Hypothetically, positive allosteric modulators (allosteric enhancers) would selectively magnify this autoprotective effect, but have no effect on CB1 receptors that are not bound by endocannabinoid, thus avoiding global CNS effects. By triggering activation of the endocannabinoid system without causing the unwanted psychotropic effects, positive allosteric modulation of the CB1 receptor would signify a nexus in cannabinoid research. Proof of principle for the concept that enhancing endocannabinoid signalling is a beneficial therapeutic strategy can be found in the effects of inhibitors of the enzymes responsible for the rapid intracellular hydrolysis of anandamide and 2AG. FAAH inhibitors are anxiolytic and antidepressant and both FAAH and MAG lipase (MAGL) inhibitors are antinociceptive; neither displays the psychoactive effects that are characteristic of direct CB1 receptor agonism (see, e.g., Cravatt et al., 2004; Piomelli et al., 2006; Guindon et al., 2007). Allosteric enhancement of the actions of anandamide and 2AG may be preferable to the global increased levels of endocannabinoid associated with inhibition of FAAH or MAG lipase respectively. Positive allosteric modulators (PAMs) would thereby afford a strategy which specifically targets known CB1 receptor signalling. In contrast, inhibition of the enzymatic breakdown of the endocannabinoids may potentially augment signalling associated with additional putative receptor targets for these eicosanoids (e.g., GPR55), thus introducing potential unexpected side-effects. In addition, in the presence of FAAH or MAGL inhibitors, the increased levels of endocannabinoids may lead to enhanced production of by-products of other metabolic pathways (e.g., COX-2), again potentially introducing unexpected side-effects. The latter two issues would not be encountered with PAMs that specifically target the CB1 receptor.

As with all allosteric enhancers, CB1 allosteric enhancers have a safety advantage over agonists in that they are less prone to overdose or toxic effect; the maximum ceiling of activity is controlled by the natural amount of endogenous ligand already in existence. Thus, positive allosteric modulators of the CB1 receptor have the advantage that they would not be expected to cause the psychotropic effects seen with agonists; allosteric inhibitors (negative modulators) of the CB1 receptor have the advantage that they would not be expected to cause the nausea and depression seen with inverse agonists. In both cases, tissue selectivity and subtle tuning (rather than global activation or complete blockage) of receptor function is expected to give an outcome more resembling normal physiology, with fewer side-effects than intervention at the orthosteric site.

Therapeutic Indications for Cannabinoid Positive Allosteric Modulators

CB1 PAMs may find clinical use, as safer alternatives to CB1 agonists, in all of the fields for which CB1 activation has been found to be of potential therapeutic benefit. These therapeutic indications include, but are not limited to: pain (neuropathic, inflammatory, acute, chemotherapy-induced pain), pain and spasticity in multiple sclerosis, chemotherapy-induced nausea, cachexia and anorexia, anxiety, post-traumatic stress disorder, depression, schizophrenia, epilepsy, Parkinson's and Huntington's diseases, Alzheimer's disease, stroke, glaucoma and retinopathy, cardiovascular and respiratory disorders, hypertension, myocardial reperfusion injury, atherosclerosis, asthma, migraine, cancer, insomnia, inflammatory bowel disease, liver disease, arthritis and osteoporosis. For reviews see e.g.: Pacher et al., 2006 and references therein; Pertwee, 2009; Parolaro et al., 2010; Pertwee, 2012. In addition, CB1 agonists have been shown to have additional therapeutic benefit when co-administered with other drugs for the treatment of a range of disorders, including: anxiety and depression, epilepsy, glaucoma, and cancer or cancer-induced vomiting (Pertwee, 2012). Thus CB1 PAMs may also be used as adjunctive therapy in these and other disorders.

Therapeutic Indications for Cannabinoid Positive Allosteric Modulators—Pain

The endocannabinoids are one of the body's most important natural painkillers, released on demand as and when they are required. Currently available compounds (agonists) indiscriminately activate this system throughout the body, causing unacceptable psychotropic side effects. Positive allosteric modulation has the advantage of increasing endocannabinoid effects only at the site of release (e.g., in the spinal cord or at the site of inflammation), thus providing pain relief where required.

The potential for modulation of the cannabinoid system for the treatment of pain has been extensively reviewed (see e.g. Pertwee, 2007, Talwar et al., 2011; Lynch and Campbell, 2011). Cannabinoids are particularly effective in the treatment of neuropathic pain and hence have potential as an adjunct to opioids in palliative care. Neuropathic pain is most commonly associated with diabetes, herpes, HIV, cancer, back pain or post-operative pain. There is ample evidence that the levels of endocannabinoids are increased in both physiological and pathophysiological situations, in which an autoprotective action of the endocannabinoids has been also implicated (Pertwee, 2005). Allosteric enhancement has the advantage of increasing endocannabinoid effects only at the site of release (e.g., in the spinal cord or at the site of inflammation), thus providing pain relief where required. CB1 PAMs are predicted to have therapeutic potential similar to that of cannabinoid agonists but, again, with a reduction in the side effects of indiscriminate systemic activation of the cannabinoid system. CB1 receptor agonists are already in use e.g., Marinol® (Solvay); Nabilone® (Eli Lilly); and in particular Sativex® (cannabis extract, GW Pharmaceuticals), which has been approved in Canada for the treatment of spasticity and pain in multiple sclerosis; it is also in development in cancer pain and neuropathic pain of various origins. There are currently ~40,000 people across Canada approved to use medical marijuana, soon to be provided by growers licensed by Health Canada. Clearly, cannabis has proven efficacy in a number of medical conditions. However, CB1 direct agonists (including $\Delta^9$-THC contained in cannabis) indiscriminately activate this system throughout the body, causing limiting psychoactive side effects and abuse liability. Recently, peripherally-restricted agonists have been described, which showed a good therapeutic window, measured in terms of anti-allodynic and anti-hyperalgesic effects without causing catalepsy (Adam et al., 2012). Furthermore, compounds which increase levels of endocannabinoids by preventing their breakdown (FAAH inhibitors) are being pursued by many pharmaceutical companies and are in Phase II clinical trials for the treatment of depression and anxiety and are in Phase I for neuropathic pain (for a review see Seierstad and Breitenbucher, 2008). Arguably, allosteric enhancement of the actions of the endocannabinoids, anandamide and 2AG may be preferable to the global increased levels of endocannabinoid associated with inhibition of FAAH or MAG lipase respectively. This would afford a strategy which specifically targets known CB1 receptor signalling, as opposed to also potentially augmenting signalling associated with putative additional targets for these eicosanoids (see Ross, 2007). On the other hand, combination of a CB1 receptor allosteric enhancer with an FAAH or MAG lipase inhibitor may afford a potent enhancement that is specific to each endocannabinoid; these combinations may prove to have disorder-specific advantages.

Therapeutic Indications for Cannabinoid Positive Allosteric Modulators—Anxiety and Depression The side effects of anti-depressants and anxiolytics are frequently reported in the scientific literature and popular media. Moreover, their efficacy is often challenged, and there is therefore a huge requirement for better drugs. It has been found that both insufficient and excessive endocannabinoid levels can lead to anxiety (Parolaro et al., 2010). The acute effects of cannabis range from euphoria and relaxation to dysphoria (potentially due to activation of TRPV1 receptors) and anxiety (Parolaro et al., 2008), again suggesting that a PAM might prove a safer alternative to direct CB1 agonism, avoiding this biphasic effect. The important role of the cannabinoid receptors in psychiatric disorders and mood states is shown by a number of observations and findings: the CB1 antagonist Acomplia was withdrawn from clinical use after being found to cause depression and suicidal ideation in a number of patients; by the long-known mood-elevating and stress-reducing properties of inhaled cannabis; the anxiolytic, antidepressant and antinociceptive properties of compounds which prevent breakdown of endocannabinoids (FAAH inhibitors); by the high levels of expression of CB1 receptors in the areas of the brain known to play a major role in mood control and cognition (Parolaro et al., 2010); by an increase in endocannabinoid concentrations following stress tests (see e.g., Crowe et al., 2014).

It is hypothesized that the endocannabinoid system exerts significant levels of control over the activation of the hormonal hypothalamic-pituitary-adrenal (HPA) axis. Excessive activity of the HPA axis is characteristic of major depressive disorder and is normalised by the use of antidepressants (Parolaro et al., 2010). CB1 activation is thought to prevent synaptic changes caused by the stress response, and thus may exert the same anti-depressant effect.

The mechanisms by which cannabinoids mediate anxiety are multiple and complex, probably involving modulation of a number of differing neurotransmitters systems, including GABA, as well as the HPA axis, and modulation of the release of opioids and cholecystokinin (Pacher et al., 2008)

It is hypothesized that that downregulation of neurogenesis leads plays a role in depression and that neurogenesis is upregulated by treatment with antidepressants. Cannabinoid agonists and FAAH inhibitors promote hippocampal neurogenesis and survival, and thus may exert an anti-depressant effect though the same mechanisms as shown by existing anti-depressants (see, e.g., Parolaro et al., 2010; Mechoulam and Parker, 2012).

It is hypothesized that CB1 agonists and inhibitors of endocannabinoid hydrolysis, may exert an anti-depressant effect by increasing the firing of serotonin and noradrenergic neurones, thus increasing the levels of these neurotransmitters. As many anti-depressant agents also increase levels of serotonin and noradrenaline (e.g., serotonin-specific reuptake inhibitors, such as fluoxetine and sertraline; serotonin-norepinephrine reuptake inhibitors, such as venlafaxine and duloxetine; and tricyclic anti-depressants, such as amitriptyline) it is thus suggested that CB1 PAMs, by increasing CB1 activity, will also show similar therapeutic benefits in the treatment of depression and anxiety.

Therapeutic Indications for Cannabinoid Positive Allosteric Modulators—Cancer

The therapeutic use of cannabinoid agonists for the control of cancer symptoms (e.g., pain, nausea and weight loss) is well-documented and a number of agents are already in clinical use. However, there is also substantial evidence that the cannabinoid system plays a significant role in tumour cell growth, proliferation and apoptosis. Endocannabinoids have been shown to induce apoptosis in many tumour cell lines, including: glioma, breast and prostate cancer, leukemia, and colon carcinoma; as well as inhibiting the growth of tumour xenografts for lung and skin carcinomas, and lymphoma (see Pacher et al., 2008 and references therein). As with many aspects of cannabinoid pharmacology, the proposed mechanisms are both complex and the response biphasic, with low concentrations having a proliferative effect and high concentrations an anti-proliferative effect (Pacher et al., 2008). Thus use of a CB1 PAM to augment the effects of a CB1 agonist, may be of therapeutic benefit.

Therapeutic Indications for Cannabinoid Negative Allosteric Modulators

It has become clear over recent decades that lifestyle-related intervention is no longer sufficient for the control of obesity, a modern plague associated with many cardiovascular complications. The possibility of pharmacological assistance is being widely investigated, but safety concerns and poor efficacy have severely limited the number of drugs to reach the market.

As described previously, drugs which block cannabinoid receptor activation were expected to find widespread use for the treatment of obesity, addiction and metabolic syndrome (see, e.g., Wadman, 2006). These were either withdrawn from the market, or clinical development halted once the side-effects of depression and suicidal thought became apparent. These events demonstrate that centrally-acting cannabinoid inverse agonists could not be used safely for the treatment of obesity.

Alongside other health risks, obesity is associated with insulin resistance and impaired glucose tolerance; the endocannabinoid system is a powerful regulator of the overactive systemic metabolism seen in type-2 diabetes.

Cannabinoid antagonists have been proposed as useful therapeutic agents in this field, but again the lack of a safe agent has thus far prevented clinical exploitation. Centrally acting CB1 antagonists such as Acomplia® and taranabant were all expected to find use in the treatment of type-2 diabetes (see, e.g., Patti, 2010). Whilst some of the beneficial effects of these agents on metabolism could be attributed to reduction in body fat, some of the effects are believed to relate to their peripheral activity. This has been demonstrated by chronic treatment with Acomplia® that not only resulted in reduction of body weight gain, but also in significant improvement in lipid profiles (reduced triglycerides and cholesterol), and glucose tolerance in obese humans and rodents (see, e.g., Bensaid et al., 2003; Scheen et al., 2006). Evidence suggests that the activation of CB1 receptors in these peripheral tissues promotes lipogenesis, lipid storage, insulin secretion, glucagon secretion and adiponectin modulation (see, e.g., Cota et al. 2003; Osei-Hyiaman et al., 2005; Bermudez-Silva et al., 2008). CB1 receptors and endocannabinoids are present in peripheral tissues involved in metabolic dysfunction associated with obesity, including adipose tissue, liver, skeletal muscle and pancreas, and there is evidence for the upregulation of the endocannabinoid system in these tissues in experimental and human obesity (see, e.g., Kunos et al., 2009). Furthermore, a peripherally-restricted CB1 receptor antagonist does not affect behavioural responses in mice with genetic or diet-induced obesity, but it does cause weight-independent improvements in glucose homeostasis, fatty liver, and plasma lipid profile (see, e.g., Tam et al., 2010). These findings confirm a role for peripheral CB1 receptors in the modulation of metabolism (see, e.g., Son et al., 2010).

Taken together, these data indicate that use of either a CB1 receptor negative allosteric modulator or a peripherally-acting negative allosteric modulator (allosteric inhibitor) may be useful in therapy for, e.g., type-2 diabetes, but may lack the side-effects seen with centrally acting CB1 receptor antagonists that target the orthosteric site.

3-(1-Nitro-1-arylethyl)-Substituted Indoles as Cannabinoid Allosteric Enhancers

Noland and Lange, 1959 first reported the synthesis of 3-(2-nitro-1-phenylethyl)-2-phenyl-1H-indole (CAS Registry Number: 102704-40-5; F-0870-0064 sometimes referred to as F-0870 or AZ-4; we believe it was first reported in a conference poster by researchers at AstraZeneca Montreal (Adam et al., 2007) and has since been reported as a $CB_1$ positive allosteric modulator at a number of academic conferences; it is commercially-available from a number of sources. At present it has only been published in Thakur and Kulkarni, 2013.

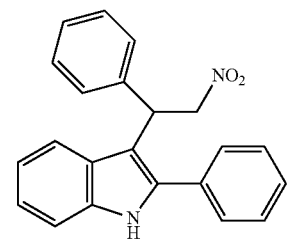

F-0870

Noland and Lange

A number of derivatives have since been reported

| CAS Registry Number or other identifier | |
|---|---|
| R = 4-Cl: 102451-67-2<br>R = 4-F: F0870-0017<br>R = 4-OMe: 33723-38-5<br>R = 2-NO2: 1240076-36-1<br>R = 2,3-OMe: 33723-37-4<br>R = 2,4-OMe: AF-399/14945096<br>R = 3,4,5-OMe: F-0870-0062 | 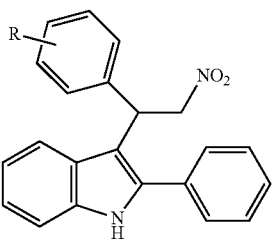 |
| R₁ = 4-OMe, R₂ = 4-OMe: 33714-05-5 / F0842-0063<br>R₁ = 3,4-OMe, R₂ = 4-Cl: AF-399/14945098<br>R2 = 4-Cl: 102451-68-3 / F-0870-0013<br>R₁ = 4-F, R₂ = 3,4-OMe: F1031-0140 | 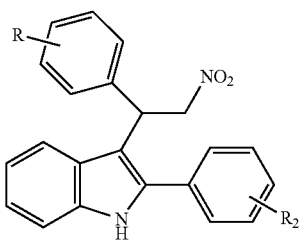 |
| 102590-84-1 | 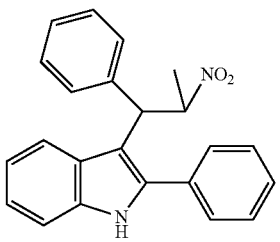 [SMILES: CC(C(c1ccccc1)c1c(-c2ccccc2)[nH]c2ccccc12)[N+](=O)[O-]] |
| R = 3,4,5-OMe: F-0870-0031<br>R = 4-Me: F-0870-0032<br>R = 4-CF₃: F-0870-0059 | 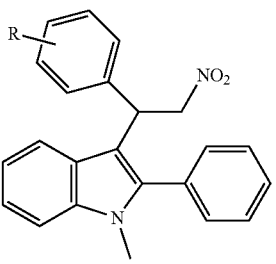 |
| R = Me: F-0870-0057<br>R = Cl: F-0870-0058 | 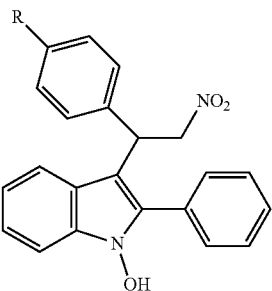 |
| AC1N5BF9 | 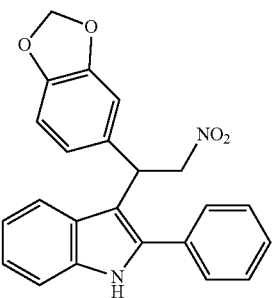 [SMILES: O=[N+]([O-])CC(c1ccc2c(c1)OCO2)c1c(-c2ccccc2)[nH]c2ccccc12] |

| CAS Registry Number or other identifier |
| --- |
| F-0870-0063 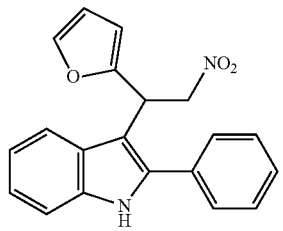 [SMILES: O=[N+]([O-])CC(c1ccco1)c1c(-c2ccccc2)[nH]c2ccccc12] |
| R = Me: F-0870-0061<br>R = 3,4-OMe: F-1031-0132 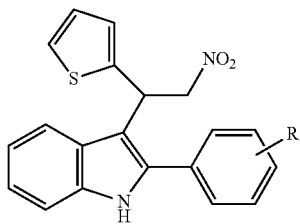 |
Thakur and Kulkarni, 2013, describes certain compounds, including the following compounds, which allegedly act as cannabinoid positive allosteric modulators with cAMP activity of <1000 nM.
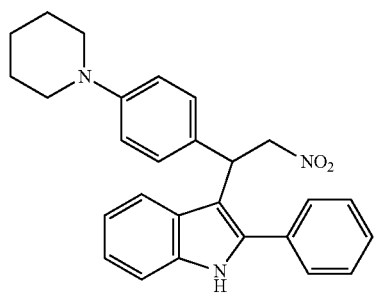
Example 5, page 63
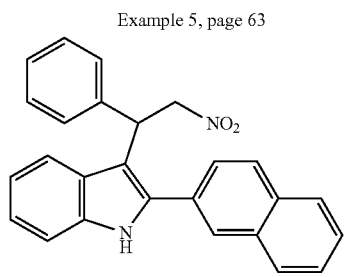
Example 6, page 64
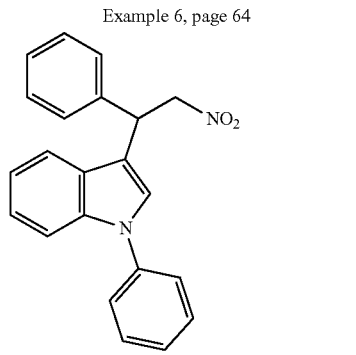
Example 9, page 64
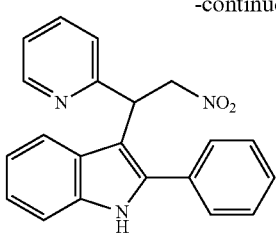
Example 10, page 65
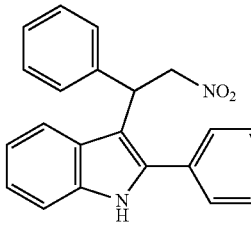
Example 13, page 65
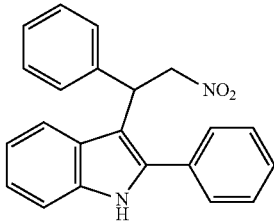
Example 14, page 65
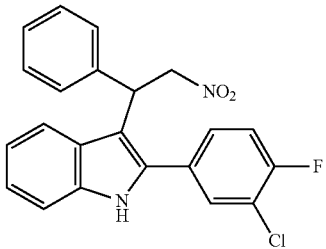
Example 15, page 65

Baillie et al., 2013, Ignatowska-Jankowska et al., 2013 and Ignatowska-Jankowska et al., 2015 report the anti-allodynic effects of ZCZ011. The potential of nitro-indole PAMs for the treatment of pain was demonstrated. ZCZ011 (40 mg/kg) significantly enhanced the pharmacological effects of both CP55,940 in C57BL/6J mice and AEA in fatty acid amide hydrolase (FAAH) knockout mice, as well as significantly increasing the potency of AEA in the drug discrimination assay. However, when given alone, ZCZ011 did not produce catalepsy, thermal antinociception, hypothermia or changes in locomotor activity. Importantly, ZCZ011 significantly reversed allodynia nociceptive responding to a normally non-noxious stimulus) induced by mechanical (von Frey filaments) or cold (acetone) stimulation in the CCI model. These anti-allodynic effects were comparable in magnitude to those produced by the FAAH inhibitor PF-3845, and were completely antagonized by rimonabant, indicating a CB1 receptor mechanism of action.

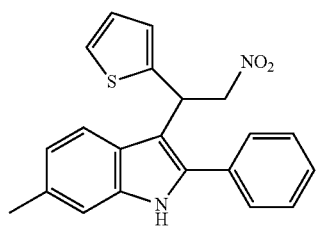

ZCZ011

CB1 PAMs, with an in vitro profile similar to that of ZCZ011, may produce an in vivo therapeutic benefit similar to that of ZCZ011. As described below, the nitro group is disfavoured in drugs; thus, the inventors have developed a novel series of therapeutic compounds, which show advantages over existing CB1 PAMs.

Requirement for Nitro Group Replacement

The nitro group is only rarely seen in drugs and, rightly or not, is often regarded as being a non-drug-like moiety by the pharmaceutical industry; finding suitable replacements for it has proven to be an ongoing challenge to medicinal chemists, with pyridine or carboxylate the most common isosteres for an aromatic nitro, but very little discussion of replacements for an aliphatic nitro (see e.g. Meanwell, 2013). The limited similarity of nitro group binding to carboxylic acid binding, in spite of the near perfect isosterism, is discussed in Kelly and Kim, 1994. Nitro groups rarely play a role in hydrogen bonding and more commonly act to fine-tune the physicochemical properties of other groups (Muegge et al., 2001). In biologically-active compounds, when they do have an effect on pharmacological properties, nitro groups are most commonly found as aromatic substituents, where their electron-withdrawing properties may polarise the ring, giving optimal interaction with electron-rich moieties within the biological target. An aromatic nitro is a well-documented toxic liability because of the potential for formation of an aryl nitrenium ion, which can bind to DNA (see Rydzewski, 2008). There is little information on toxicological issues associated with aliphatic nitro groups, and that which is available generally relates to short-chain alkyl nitro compounds, which may not be representative of the impact of a nitro group when present on a larger structure. Because of its strong electron-withdrawing nature, its presence facilitates many chemical reactions; thus it is often found in screening collections, but has to be replaced from the hits identified if they are to be developed as drugs. It has even been informally suggested that replacement is frequently not possible because of the multiple binding modes and receptor interactions possible with a nitro group, and thus should not even be present in screening collections or laboratory tool compounds; thus it is usually not regarded as being a pharmacophore and is often pre-filtered from compound libraries (see e.g. Baell and Holloway, 2010). Marketed drugs which do contain a nitro group include chloramphenicol, metronidazole and ranitidine.

In addition to the stigma associated with nitro groups in general, F-0870-based compounds have been shown to be metabolically unstable, with biological half-lives of <10 minutes in rat liver microsomes (see Table 3). It is clear that, in spite of the ease of access to positive allosteric modulators based on F-0870, replacement of the nitro group is a step in the development of such compounds as therapeutic agents.

Replacement of the Nitro Group with a Suitable Bioisostere

Thakur and Kulkarni, 2013, makes broad claims to the below structure, in which Z may be $NO_2$ or CN and $R_1$ may be a range of substituents, including halogen, alkyl or alkoxy. However, it does not exemplify derivatives or suggest synthetic routes which would permit the synthesis of derivatives in which Z=ON; nor does it exemplify derivatives or suggest synthetic routes to derivatives in which $R_1$ is a group other than H.

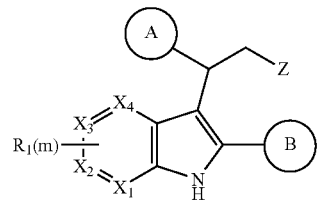

The reaction of an indole with nitrostyrene has been widely reported in the literature and there are a range of methods available for this simple condensation, facilitated both by the electron-withdrawing characteristics of the nitro group, but also potentially by the stability of a cyclic intermediate, exclusive to the nitro group (see Noland and Lange, 1959). Methods for the reaction between 2-phenylindole and nitrostyrene are discussed in Babu et al., 2008 (tertiarybutylammonium bromide catalyst); Gu et al., 2012 (glycerol catalyst), Bandini et al., 2002 (indium tribromide catalyst), Praveen et al., 2009 (gold chloride catalyst), Kumar et al., 2008 (β-cyclodextrin catalyst), Habib et al., 2010 (solvent-free), and indeed, the reaction of 2-phenylindole with nitrostyrene can also be achieved using the water catalysed or N-bromosuccinimide-catalysed methods described for other indoles in Habib et al., 2008 and Kuo et al., 2009 respectively.

However, methods for the replacement of the nitro group with another substituent, such as claims for Z=CN in Thakur and Kulkarni, 2013, are not generally available in the literature; the above methods do not give the desired product for reactions in which the nitro starting material has been replaced with a nitrile, bis-nitrile or trifluoromethyl-bearing starting material.

An exception to this is replacement of the nitro group with a carboxylic acid, which is achieved by reaction of an indole with e.g. diethylbenzylidene malonate, in the presence of a suitable copper catalyst. Removal of one of the ester groups can be achieved with sodium chloride in DMSO to give the mono-ester derivative, and hydrolysis of the remaining ester in basic conditions yields the carboxylic acid derivative. This reaction is again facilitated by the strong electron-withdrawing characteristics of the two carboxylate groups in the reactant and is not generally applicable to reactions with any other starting materials. The synthesis of the diester, using a copper triflate catalyst, is described by Guo et al., 2010; the carboxylic acid derivative below can then be prepared from the diester, using the method described for the unsubstituted indoles in Zhuang et al., 2001. However, in our hands, the $CO_2H$, $CO_2Et$, $CONHNH_2$, $CONH_2$ and CONHMe derivatives were inactive as a $CB_1$ PAM (see Table 2), in spite of having similar electronic distribution to the nitro derivative; thus demonstrating that replacement of the nitro group is not a facile process, and that selection of a suitable bioisostere for the nitro is not obvious.

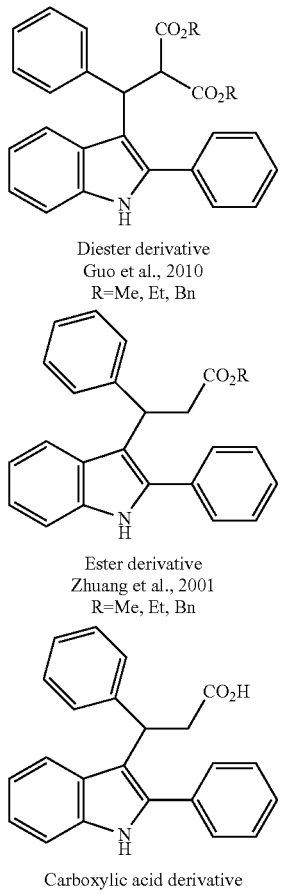

Diester derivative
Guo et al., 2010
R=Me, Et, Bn

Ester derivative
Zhuang et al., 2001
R=Me, Et, Bn

Carboxylic acid derivative

Amino derivatives of F-0870 are easily accessible via reduction of the nitro group. A number of related amine-containing 3-(1-arylethyl)-indoles have been described. In our hands, neither the unsubstituted amine, nor compounds in which the amine was substituted with —$SO_2Me$, —$SO_2Ph$ or —$CONH_2$, were active as $CB_1$ PAMs (see Table 2), in spite of this having a similar electronic distribution to the nitro group.

| CAS Registry Number or other identifier | |
|---|---|
| $R_1$ = H, $R_2$ = H: 102441-39-4<br>$R_1$, $R_2$ = Me: 102747-56-8<br>$R_1$ = H, $R_2$ = $CONH_2$: 102888-70-0<br>$R_1$ = H, $R_2$ = $CO_2Et$: 102892-39-7<br>$R_1$ = H, $R_2$ = COPh: 103269-26-7<br>$R_1$, $R_2$ = $C_2H_4OH$: 103211-56-9<br>$R_1$ = H, $R_2$ = $SO_2Ph$-p-$NO_2$: Reaxys Registry Number: 9734118 | 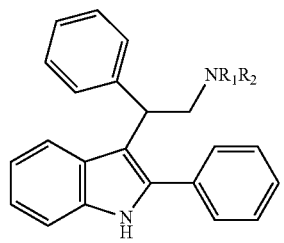 |
| 102951-88-2 | 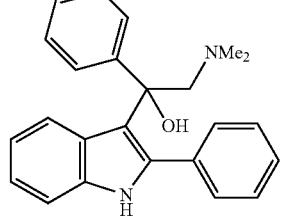 |

In general, the hindered nature of 2-phenylindoles, makes additional substitution at the 3-position very difficult and thus condensation reactions, to form 3-substituted derivatives, which would be facile with either unsubstituted or 2-methylindoles, do not yield the desired products with 2-phenylindoles. Thus, while an unsubstituted- or 2-methylindole will react with 2-benzylidenemalononitrile in the presence of a copper catalyst, to give the structures shown in Qu et al., in our hands, the reaction did not yield the desired product when 2-phenylindole was used as the starting material and such a product has not previously been reported.

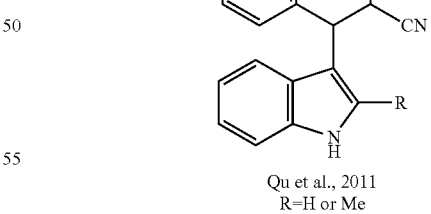

Qu et al., 2011
R=H or Me

In principle, it should be possible to generate the required 3-substituted indole derivative, and then brominate at the 2-position, facilitating addition of the 2-phenyl group by Suzuki coupling. However, in our hands either bromination did not occur, or the resultant 2-bromo derivative was unstable, and thus synthesis of the target compounds (e.g., where R' phenyl from the above examples) was not possible using existing methodology.

Other related derivatives described previously include:
| CAS Registry Number or other identifier | |
|---|---|
| 135578-20-0 | 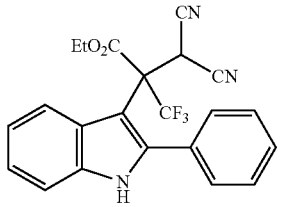 [SMILES: CCOC(=O)C(c1c(-c2ccccc2)[nH]c2ccccc12)(C(C#N)C#N)C(F)(F)F] |
| $R_1$ = H, $R_2$ = OH: Reaxys Registry Number: 7048825<br>$R_1$ = OH, $R_2$ = H: Reaxys Registry Number: 7049254 | 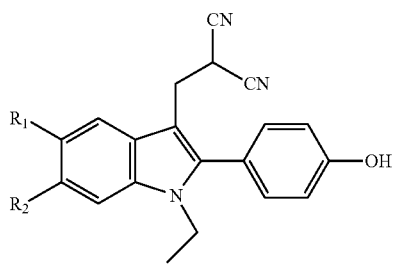 |
| 371969-40-3 | 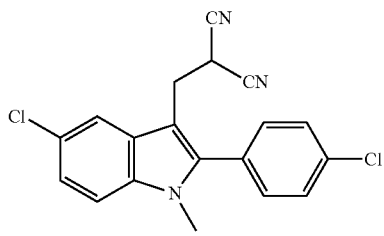 [SMILES: Cn1c(-c2ccc(Cl)cc2)c(CC(C#N)C#N)c2cc(Cl)ccc21] |
| 1111212-77-1 | 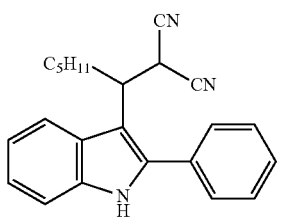 |
| 135578-19-7 | 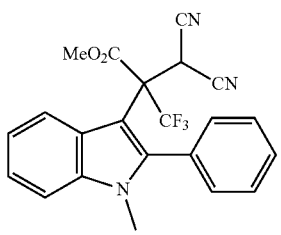 [SMILES: COC(=O)C(c1c(-c2ccccc2)n(C)c2ccccc12)(C(C#N)C#N)C(F)(F)F] |
| R = H: Reaxys Registry Number: 9857128<br>R = Cl: 1234579-42-0<br>R = Me: 1234579-43-1<br>R = OMe: 1284227-98-0 | 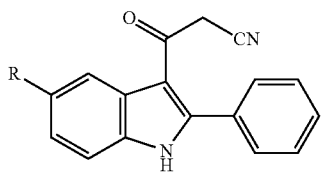 |
| 23999-49-7 | 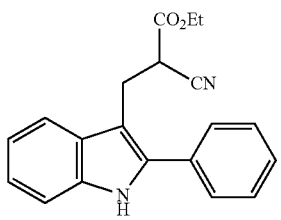 [SMILES: CCOC(=O)C(C#N)Cc1c(-c2ccccc2)[nH]c2ccccc12] |

-continued

| CAS Registry Number or other identifier | |
|---|---|
| 102892-42-2 | 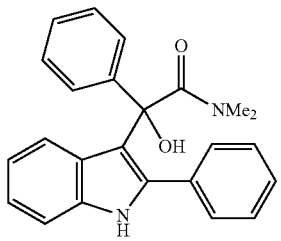 [SMILES: CN(C)C(=O)C(O)(c1ccccc1)c1c(-c2ccccc2)[nH]c2ccccc12] |
| 1459775-52-0 | 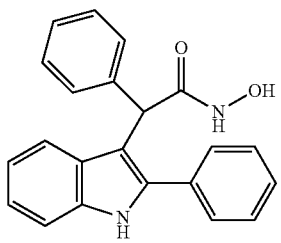 [SMILES: O=C(NO)C(c1ccccc1)c1c(-c2ccccc2)[nH]c2ccccc12] |

The lack of existing synthetic methods, or the lack of transferability of existing methods, demonstrates that the synthesis of target bioisosteres of the nitro group is not an obvious step, even to one of skill in the art of synthetic chemistry. Thus, methods for the generation of F-0870 PAM derivatives in which the nitro is replaced by a suitable active bioisostere, a non-nitro-PAM (NN-PAM) have not previously been described.

SUMMARY

The inventors have developed a series of compounds which have retained the pharmacological activity and potency of F-0870 but which, in lacking the nitro group, maintain drug-like properties.

The present disclosure relates to compounds of the Formula (I) which are cannabinoid type 1 receptor modulators, and their use in the treatment of diseases in which modulation of the receptor is beneficial. In particular, the present disclosure relates to 2,3,6-substituted indoles which are non-nitro positive allosteric modulators (NN-PAMs) of the cannabinoid type 1 receptor.

In one embodiment of the disclosure, there is included a compound of the Formula (I)

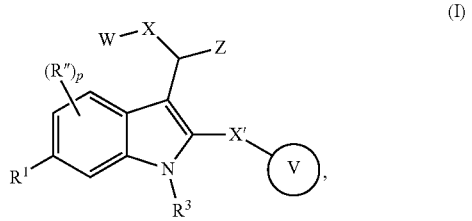

wherein,
W is $(C_1-C_{10})$-alkyl, $(C_3-C_{10})$-cycloalkyl, $(C_3-C_{10})$-heterocycloalkyl, $(C_6-C_{10})$-aryl, or $(C_5-C_{10})$-heteroaryl, each of which is optionally substituted with one or more of halo, —$CF_3$, —$OCF_3$, —CN, —$NO_2$, —R, —OR, —SR, —$NR_2$, —$NR'_2$, —C(=O)R, —C(=O)OR, —NRC(=O)R, —C(=O)$NR_2$, —C(=O)$NR'_2$, —S(=O)$_2NR_2$, —S(=O)$_2NR'_2$, —NRS(=O)$_2$R, —S(=O)$_2$R or —S(=O)$CF_3$, wherein R is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl, and R' is independently or simultaneously H, azetidino, pyrrolidino, piperidino, piperazino, morpholino, azepano, or diazepano;

X and X' are independently or simultaneously $(C_0-C_4)$-alkylene, optionally substituted with one or more of halo, —$CF_3$, OH, $OCF_3$, or —O—$(C_1-C_4)$alkyl;

Z is —$CH_2CN$, —$CH(CN)_2$, —$CH_2CF_3$, or —C(=O)$CF_3$;

Ring V is $(C_3-C_{10})$-cycloalkyl, $(C_3-C_{10})$-heterocycloalkyl, $(C_6-C_{10})$-aryl, or $(C_5-C_{10})$-heteroaryl, each of which is optionally substituted with one or more of the optional substituents defined in the variable W;

$R^1$ is halo, —$CF_3$, —$OCF_3$, —CN, —$NO_2$, —$R^2$, —$OR^2$, —SR, —$N(R^2)_2$, —$(NR^{2'})_2$, —C(=O)$R^2$, —C(=O)$OR^2$, —$NR^2$C(=O)$R^2$, —C(=O)N$(R^2)_2$, —C(=O)N$(R^{2'})_2$, —S(=O)$_2$N$(R^2)_2$, —S(=O)$_2$N$(R^{2'})_2$, —$NR^2$S(=O)$_2R^2$, —S(=O)$_2R^2$ or —S(=O)$CF_3$, wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl, and $R^{2'}$ is independently or simultaneously H, azetidino, pyrrolidino, piperidino, piperazino, morpholino, azepano, or diazepano;

$R^3$ is H or $(C_1-C_6)$alkyl;

R" is halo, —$CF_3$, —$OCF_3$, —CN, —$NO_2$, —$R^4$, —$OR^4$, —SR, —$N(R^4)_2$, —$(NR^{4'})_2$, —C(=O)$R^4$, —C(=O)$OR^4$, —$NR^4$C(=O)$R^4$, —C(=O)N$(R^4)_2$, —C(=O)N$(R^{4'})_2$, —(=O)$_2$N$(R^4)_2$, —S(=O)$_2$N$(R^{4'})_2$, —$NR^4$S(=O)$_2R^4$, —S(=O)$_2R^4$ or —S(=O)$CF_3$, wherein $R^4$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl, and $R^{4'}$ is independently or simultaneously H, azetidino, pyrrolidino, piperidino, piperazino, morpholino, azepano, or diazepano;

p is the integer 0, 1, 2 or 3, and pharmaceutically acceptable salts, stereoisomers, and/or solvates thereof.

In one embodiment, the compounds of the Formula (I) are positive allosteric modulators (PAMs) of the cannabinoid type 1 receptor. In another embodiment and in one object of the disclosure, the compounds of the Formula (I) are useful for the treatment of diseases or conditions in which modulation of the cannabinoid type 1 receptor is beneficial. In another embodiment, the disease or condition is pain, multiple sclerosis, depression, an eating disorder, a cardiovascular disease, non-alcoholic fatty liver disease associated with metabolic syndrome, addiction or a symptom of addiction, a bone disorder, cancer, an inflammatory or autoimmune disease, asthma, a psychiatric disorder, epilepsy, glaucoma, retinopathy, nausea or vomiting associated with cancer chemotherapy, a neurodegenerative disorder, or memory impairment.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DESCRIPTION OF VARIOUS EMBODIMENTS (I) Definitions

The term "$(C_1\text{-}C_p)$_alkyl" as used herein means straight and/or branched chain, saturated alkyl moieties containing from one to "p" carbon atoms and includes (depending on the identity of p) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical.

The term "$(C_2\text{-}C_p)$_alkenyl" as used herein means straight and/or branched chain, unsaturated alkyl moieties containing from one to "p" carbon atoms and includes at least one carbon-carbon double bond and includes (depending on the identity of p) ethenyl, 1-propenyl, isopropenyl, 1-butenyl, 2-butenyl, t-butenyl, 1-pentenyl, 2-methyl-1-pentenyl, 3-methyl-1-pentenyl, 4-methyl-1-pentenyl, 1-hexenyl, 2-hexenyl and the like, where the variable p is an integer representing the largest number of carbon atoms in the alkenyl radical.

The term "$(C_2\text{-}C_p)$_alkynyl" as used herein means straight and/or branched chain, unsaturated alkyl moieties containing from one to "p" carbon atoms and includes at least one carbon-carbon triple bond (and optionally including double bonds) and includes (depending on the identity of p) ethynyl, 1-propynyl, isopropynyl, 1-butynyl, 2-butynyl, 1-pentynyl, 3-methyl-1-pentynyl, 4-methyl-1-pentynyl, 1-hexynyl, 2-hexynyl and the like, where the variable p is an integer representing the largest number of carbon atoms in the alkynyl radical.

The term "$C_{3\text{-}p}$cycloalkyl" as used herein means a monocyclic, bicyclic or tricyclic saturated carbocyclic group containing from three to "p'" carbon atoms and includes (depending on the identity of p) cyclopropyl, cyclobutyl, cyclopentyl, cyclohexyl and the like, where the variable p' is an integer representing the largest number of carbon atoms in the cycloalkyl radical. The term cycloalkyl also includes all of the fully saturated and partially unsaturated derivatives of the below-mentioned aryl groups The term "heteroaryl" as used herein refers to aromatic cyclic or polycyclic ring systems having at least one heteroatom chosen from N, O and S and at least one aromatic ring. Examples of heteroaryl groups include, without limitation, furyl, thienyl, pyridyl, pyrazinyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl and quinazolinyl, among others.

The term "heterocyclylalkyl" as used herein includes non-aromatic rings or ring systems that contain at least one ring having at least one heteroatom (such as nitrogen, oxygen or sulfur). For example, the heterocyclyl groups include all of the fully saturated and partially unsaturated derivatives of the above-mentioned heteroaryl groups. Examples of heterocyclic groups include, without limitation, piperidinyl, tetrahydropyranyl, pyrrolidinyl, tetrahydrofuranyl, morpholinyl, thiomorpholinyl, piperidinyl, piperazinyl, thiazolidinyl, isothiazolidinyl, and imidazolidinyl.

The term "aryl" as used herein refers to cyclic groups that contain at least one aromatic ring, for example a single ring (e.g. phenyl) or multiple condensed rings (e.g. naphthyl). In an embodiment of the present disclosure, the aryl group contains 6, 9 or 10 atoms such as phenyl, naphthyl, indanyl, anthracenyl, 1,2-dihydronaphthyl, 1,2,3,4-tetrahydronaphthyl, fluorenyl, indanyl, indenyl and the like The suffix "ene" added on to any of the above groups means that the group is divalent, i.e. inserted between two other groups.

The term "halo" as used herein refers to a halogen atom and includes fluorine (F), chlorine (Cl), bromine (Br) and iodine (I).

The term "pharmaceutically acceptable salt" refers, for example, to a salt that retains the desired biological activity of a compound of the present disclosure and does not impart undesired toxicological effects thereto; and may refer to an acid addition salt or a base addition salt.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the present disclosure, the compounds may have an asymmetric center. These compounds exist as enantiomers. Where compounds possess more than one asymmetric center, they may exist as diastereomers. It is to be understood that all such isomers and mixtures thereof in any proportion are encompassed within the scope of the present disclosure, and are known, generally, as stereosiomers. It is to be further understood that while the stereochemistry of the compounds may be as shown in any given compound listed herein, such compounds may also contain certain amounts (e.g. less than 20%, suitably less than 10%, more suitably less than 5%) of compounds of the disclosure having alternate stereochemistry. For example, compounds of the disclosure that are shown without any stereochemical designations are understood to be racemic mixtures (i.e. contain an equal amount of each possible enantiomer or diastereomer). However, it is to be understood that all enantiomers and diastereomers are included within the scope of the present disclosure, including mixtures thereof in any proportion.

The term "effective amount" or "therapeutically effective amount" or "pharmaceutically effective amount" as used herein means an amount effective, at dosages and for periods of time necessary to achieve the desired result. For example in the context of treating a subject with a disease or condition in which modulation of the cannabinoid type 1 receptor would be beneficial, such as pain, an effective amount is an amount that, for example, provides some alleviation, mitigation and/or decrease in the amount of pain experienced by a subject.

Effective amounts may vary according to factors such as the disease state, age, sex and/or weight of the subject. The amount of a given compound that will correspond to such an amount will vary depending upon various factors, such as the given drug or compound, the pharmaceutical Formulation, the route of administration, the type of condition, disease or disorder, the identity of the subject being treated, combination treatment, and the like, but can nevertheless be routinely determined by one skilled in the art.

As used herein, a "subject" refers to all members of the animal kingdom including mammals, and suitably refers to humans. A member of the animal kingdom includes, without limitation, a mammal (such as a human, primate, swine, sheep, cow, equine, horse, camel, canine, dog, feline, cat, tiger, leopard, civet, mink, stone marten, ferret, house pet, livestock, rabbit, mouse, rat, guinea pig or other rodent, seal, whale and the like), fish, amphibian, reptile, and bird (such as water fowl, migratory bird, quail, duck, goose, poultry, or chicken). In an embodiment of the present disclosure, the subject is in need of a compound or composition of the disclosure.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

As used herein, the term "prodrug" refers to a substance that is prepared in an inactive form that is converted to an active form (i.e., drug) within the body or cells thereof by the action of, for example, endogenous enzymes or other chemicals and/or conditions. Prodrug derivatives of the compounds of Formula (I) or pharmaceutically acceptable salts or solvates thereof, can be prepared by methods known to those of ordinary skill in the art.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

(II) Compounds of the Disclosure

The present disclosure relates to compounds of the Formula (I) which are cannabinoid type 1 receptor modulators, and their use in the treatment of diseases in which modulation of the receptor is beneficial. In particular, the present disclosure relates to 2,3,6-substituted indoles which are non-nitro positive allosteric modulators (NN-PAMs) of the cannabinoid type 1 receptor.

In one embodiment of the disclosure, there is included a compound of the Formula (I)

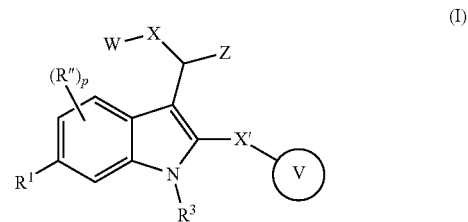

wherein,

W is $(C_1\text{-}C_{10})$-alkyl, $(C_3\text{-}C_{10})$-cycloalkyl, $(C_3\text{-}C_{10})$-heterocycloalkyl, $(C_6\text{-}C_{10})$-aryl, or $(C_5\text{-}C_{10})$-heteroaryl, each of which is optionally substituted with one or more of halo, —$CF_3$, —$OCF_3$, —CN, —$NO_2$, —R, —OR, —SR, —$NR_2$, —$NR'_2$, —C(=O)R, —C(=O)OR, —NRC(=O)R, —C(=O)$NR_2$, —C(=O)$NR'_2$, —S(=O)$_2NR_2$, —S(=O)$_2NR'_2$, —NRS(=O)$_2$R, —S(=O)$_2$R or —S(=O)$CF_3$, wherein R is independently or simultaneously H, $(C_1\text{-}C_6)$-alkyl, $(C_2\text{-}C_6)$-alkenyl, $(C_2\text{-}C_6)$-alkynyl, $(C_3\text{-}C_6)$-cycloalkyl, phenyl or benzyl, and R' is independently or simultaneously H, azetidino, pyrrolidino, piperidino, piperazino, morpholino, azepano, or diazepano;

X and X' are independently or simultaneously $(C_0\text{-}C_4)$-alkylene, optionally substituted with one or more of halo, —$CF_3$, OH, $OCF_3$, or —O—$(C_1\text{-}C_4)$alkyl;

Z is —$CH_2CN$, —$CH(CN)_2$, —$CH_2CF_3$, or —C(=O)$CF_3$;

Ring V is $(C_3\text{-}C_{10})$-cycloalkyl, $(C_3\text{-}C_{10})$-heterocycloalkyl, $(C_6\text{-}C_{10})$-aryl, or $(C_5\text{-}C_{10})$-heteroaryl, each of which is optionally substituted with one or more of the optional substituents defined in the variable W;

$R^1$ is halo, —$CF_3$, —$OCF_3$, —CN, —$NO_2$, —$R^2$, —$OR^2$, —SR, —$N(R^2)_2$, —$(NR^{2'})_2$, —C(=O)$R^2$, —C(=O)$OR^2$, —$NR^2C(=O)R^2$, —C(=O)$N(R^2)_2$, —C(=O)$N(R^{2'})_2$, —S(=O)$_2N(R^2)_2$, —S(=O)$_2N(R^{2'})_2$, —$NR^2S(=O)_2R^2$, —S(=O)$_2R^2$ or —S(=O)$CF_3$, wherein $R^2$ is independently or simultaneously H, $(C_1\text{-}C_6)$-alkyl, $(C_2\text{-}C_6)$-alkenyl, $(C_2\text{-}C_6)$-alkynyl, $(C_3\text{-}C_6)$-cycloalkyl, phenyl or benzyl, and $R^{2'}$ is independently or simultaneously H, azetidino, pyrrolidino, piperidino, piperazino, morpholino, azepano, or diazepano;

$R^3$ is H or $(C_1\text{-}C_6)$alkyl;

R" is halo, —$CF_3$, —$OCF_3$, —CN, —$NO_2$, —$R^4$, —$OR^4$, —SR, —$N(R^4)_2$, —$(NR^{4'})_2$, —C(=O)$R^4$, —C(=O)$OR^4$, —$NR^4C(=O)R^4$, —C(=O)$N(R^4)_2$, —C(=O)$N(R^{4'})_2$, —S(=O)$_2N(R^4)_2$, —S(=O)$_2N(R^{4'})_2$, —$NR^4S(=O)_2R^4$, —S(=O)$_2R^4$ or —S(=O)$CF_3$, wherein $R^4$ is independently or simultaneously H, $(C_1\text{-}C_6)$-alkyl, $(C_2\text{-}C_6)$-alkenyl, $(C_2\text{-}C_6)$-alkynyl, $(C_3\text{-}C_6)$-cycloalkyl, phenyl or benzyl, and $R^{4'}$ is independently or simultaneously H, azetidino, pyrrolidino, piperidino, piperazino, morpholino, azepano, or diazepano;

p is the integer 0, 1, 2 or 3, and pharmaceutically acceptable salts, stereoisomers, and/or solvates thereof.

In one embodiment, W is $(C_1-C_6)$-alkyl, $(C_3-C_6)$-cycloalkyl, $(C_3-C_6)$-heterocycloalkyl, $(C_6)$-aryl, or $(C_5-C_6)$-heteroaryl. In another embodiment, W is $(C_1-C_4)$-alkyl, $(C_5-C_6)$-cycloalkyl, $(C_5-C_6)$-heterocycloalkyl, phenyl or $(C_5-C_6)$-heteroaryl. In one embodiment, W is isopropyl, cyclopropyl, piperidinyl, tetrahydropyranyl, phenyl, thiophenyl, furanyl, pyridinyl, pyrimidinyl or pyrazinyl. In another embodiment of the disclosure, W is phenyl, furanyl, cyclopropyl, or thiophenyl. In a further embodiment of the disclosure, the optional substituents on W are one or more of halo, —$CF_3$, —$OCF_3$, —CN, —R, or —OR.

In another embodiment of the disclosure, X and X' are independently or simultaneously $(C_0-C_2)$-alkylene. In a further embodiment, X and X' are independently or simultaneously $(C_0-C_1)$-alkylene.

In another embodiment, Z is —$CH(CN)_2$, —$CH_2CF_3$, or —$C(=O)CF_3$. In one embodiment, Z is —$CH(CN)_2$. In another embodiment, Z is —$CH_2CF_3$. In another embodiment, Z is —$C(=O)CF_3$.

In another embodiment, Ring V is $(C_3-C_6)$-cycloalkyl, $(C_3-C_6)$-heterocycloalkyl, $(C_6)$-aryl, or $(C_5-C_6)$-heteroaryl. In another embodiment, Ring V is $(C_5-C_6)$-cycloalkyl, $(C_5-C_6)$-heterocycloalkyl, phenyl or $(C_5-C_6)$-heteroaryl. In a further embodiment, Ring V is cyclopropyl, cyclopentyl, piperidinyl, tetrahydropyranyl, phenyl, thiophenyl, furanyl, pyridinyl, pyrimidinyl or pyrazinyl. In an embodiment, Ring V is phenyl or cyclopentyl.

In a further embodiment of the disclosure, the optional substituents on Ring V are one or more of halo, —$CF_3$, —$OCF_3$, —CN, —R, or —OR.

In another embodiment of the disclosure, $R^1$ is halo, —$CF_3$, —$OCF_3$, —CN, —$NO_2$, —$R^2$, —$OR^2$, —SR, or —$N(R^2)_2$, wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl. In a further embodiment, $R^1$ is halo, —$CF_3$, —$OCF_3$, —CN, —$NO_2$, —$R^2$ or —$OR^2$, wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl. In another embodiment, $R^1$ is halo, —$CF_3$, —$OCF_3$, —CN, or —$R^2$ wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl. In a further embodiment, $R^1$ is halo, —$CF_3$, or —$R^2$ wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl. In another embodiment, $R^1$ is halo, —$CF_3$, or —$R^2$ wherein $R^2$ is independently or simultaneously H, $(C_1-C_3)$-alkyl, $(C_2-C_3)$-alkenyl, $(C_2-C_3)$-alkynyl, or $(C_3-C_6)$-cycloalkyl. In a further embodiment, $R^1$ is Cl, —$CF_3$, or —$R^2$ wherein $R^2$ is independently or simultaneously H or methyl. In one embodiment, $R^1$ is Cl, $CF_3$, or methyl.

In another embodiment, R" is halo, —$CF_3$, —$OCF_3$, —CN, —$NO_2$, —$R^4$, —$OR^4$, —SR, -or $N(R^4)_2$, wherein $R^4$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl. In another embodiment, R" is $CF_3$, —$OCF_3$, —CN, —$NO_2$, —$R^4$, or —$OR^4$, wherein $R^4$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl. In another embodiment, R" is halo, —$CF_3$, —$OCF_3$, —CN, or —$R^4$ wherein $R^4$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl. In another embodiment, R" is halo, —$CF_3$, —$OCF_3$, —CN, or —$R^4$ wherein $R^4$ is independently or simultaneously H, $(C_1-C_3)$-alkyl, $(C_2-C_3)$-alkenyl, or $(C_2-C_3)$-alkynyl.

In one embodiment of the disclosure, wherein p is 0 or 1. In another embodiment, p is 0.

In one embodiment, $R^3$ is H or $(C_1-C_3)$-alkyl. In a further embodiment, $R^3$ is H or methyl.

In one embodiment of the disclosure, the compound of the Formula (I) is

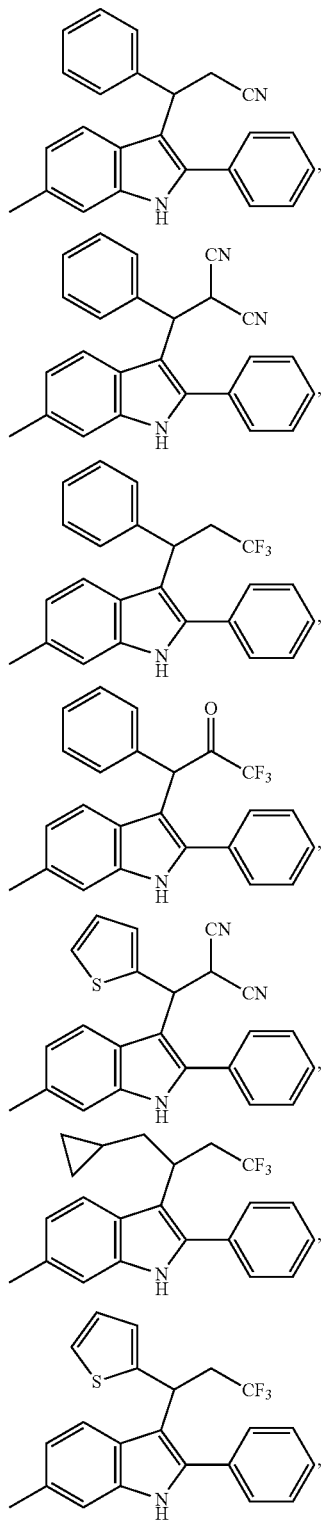

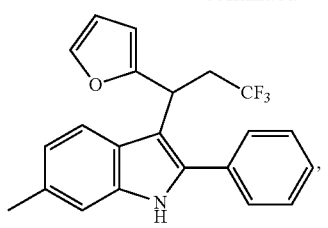
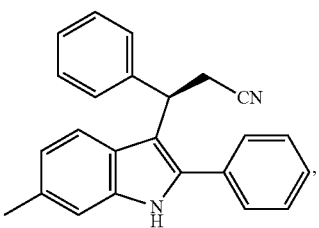
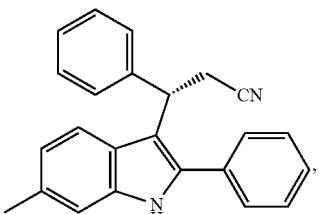
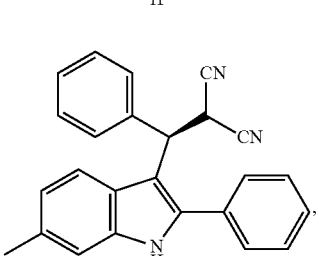
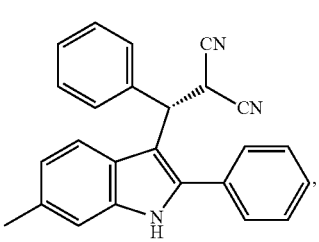
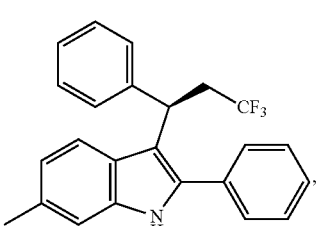
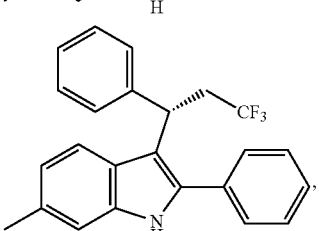
, or
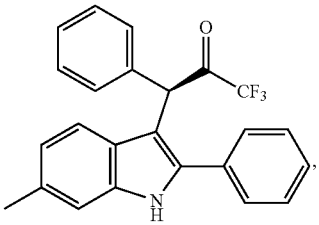
In another embodiment of the disclosure, the compound of the Formula (I) is

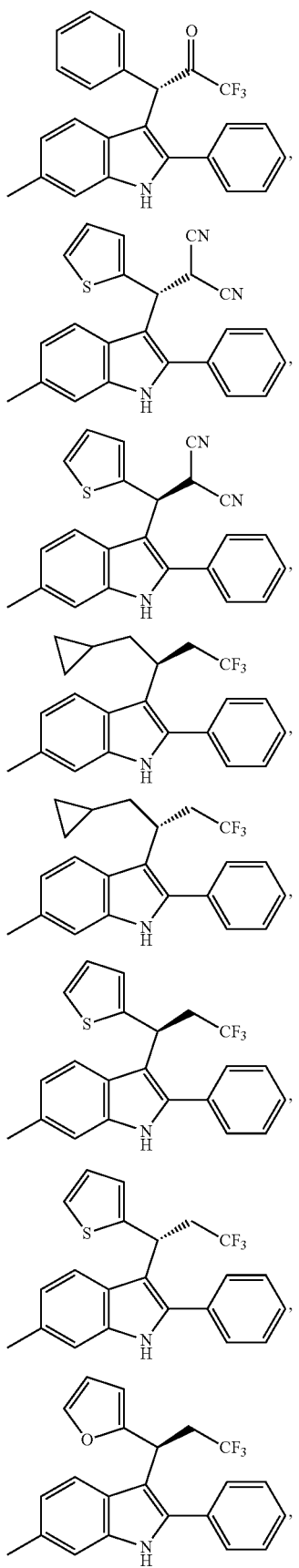
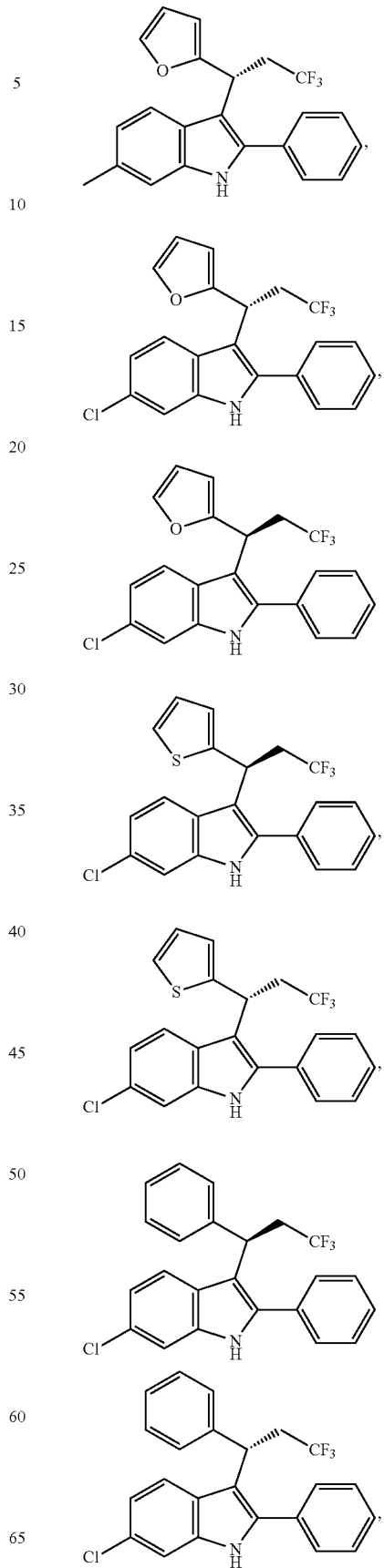

-continued

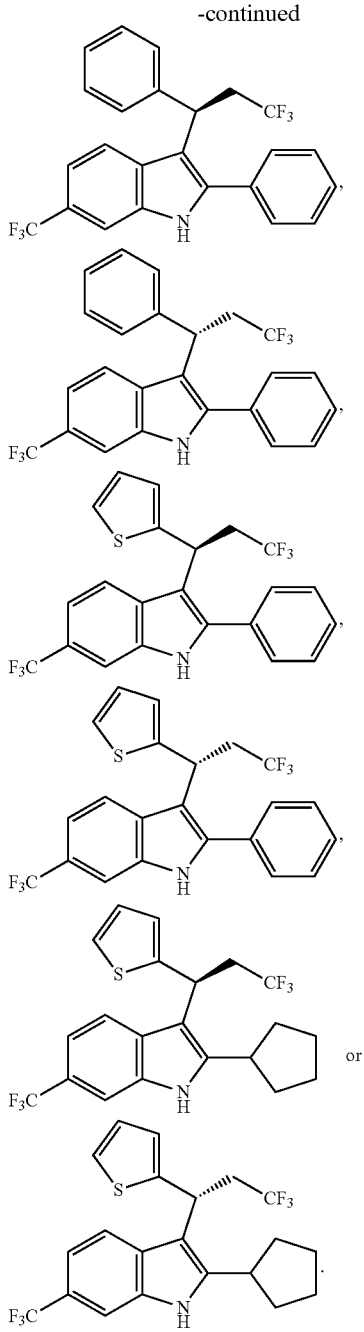

In one embodiment of the disclosure, the compound of the Formula (I) is a compound of the Formula (II)

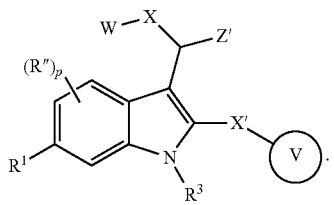

wherein,
Z' is —CH$_2$CN; and wherein the variables W, X, X', Ring V, R$^1$, R$^3$, R" and p are as defined above in each embodiment.

In one embodiment, the compound of the Formula (II) is

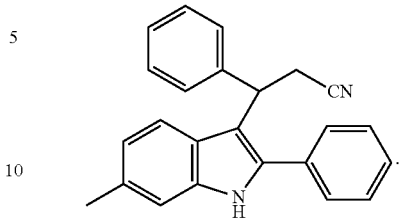

In another embodiment, the compound of the Formula (II) is

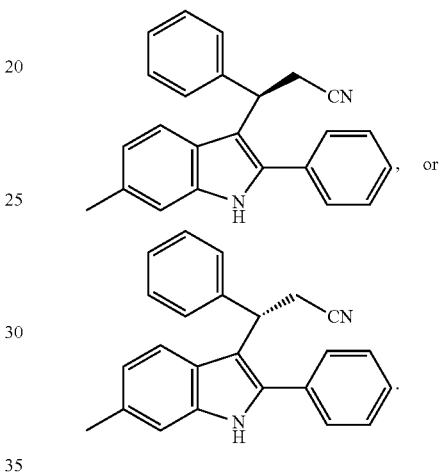

In one embodiment of the disclosure, the compound of the Formula (I) is a compound of the Formula (III)

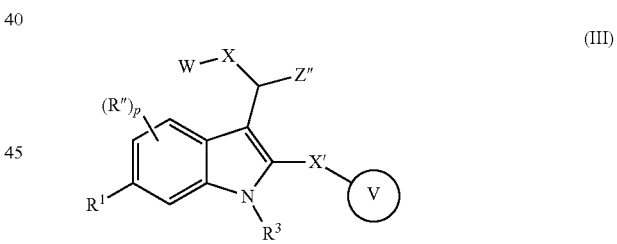

wherein,
Z" is —CH(CN)$_2$, —CH$_2$CF$_3$, or —C(=O)CF$_3$, and wherein the variables W, X, X', Ring V, R$^1$, R$^3$, R" and p are as defined above in each embodiment.

In one embodiment, the compound of the Formula (III) is

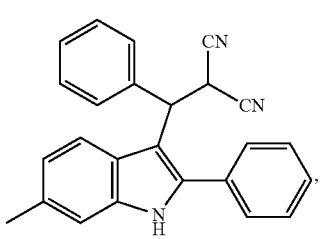

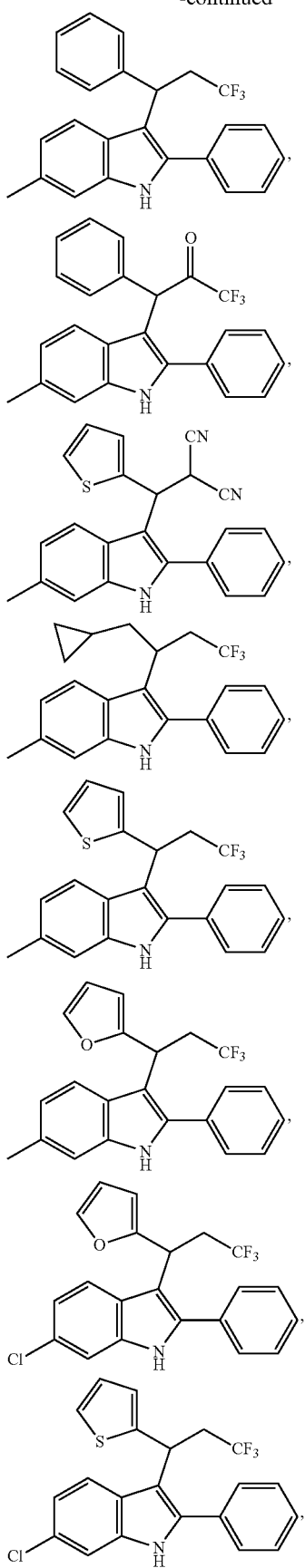
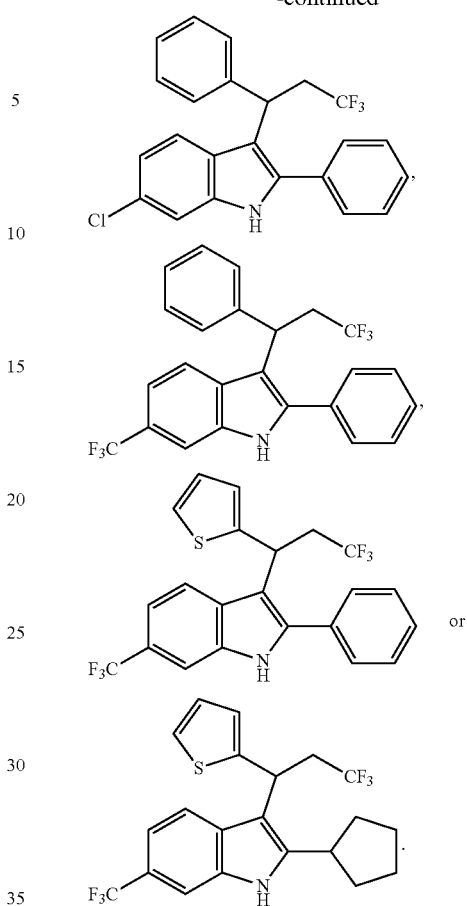
In another embodiment, the compound of the Formula (III) is
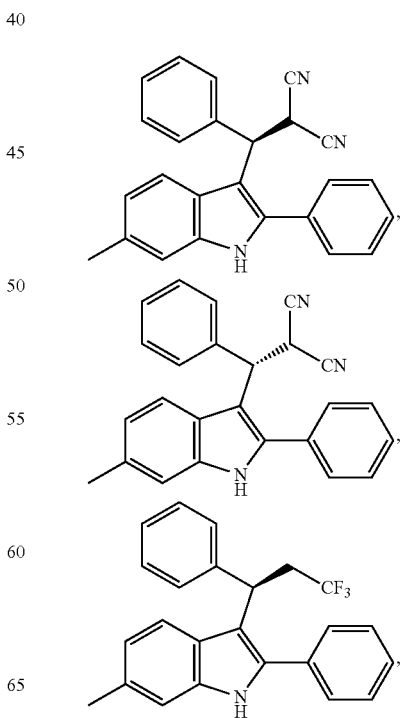

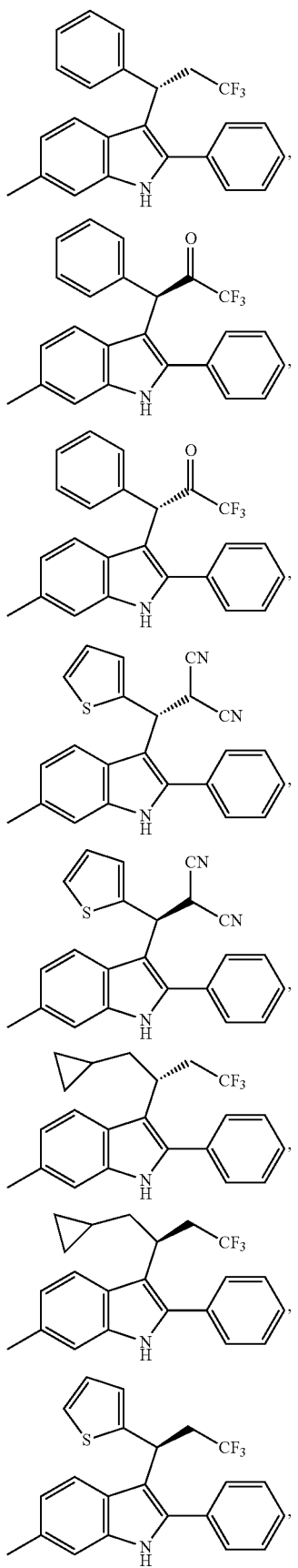
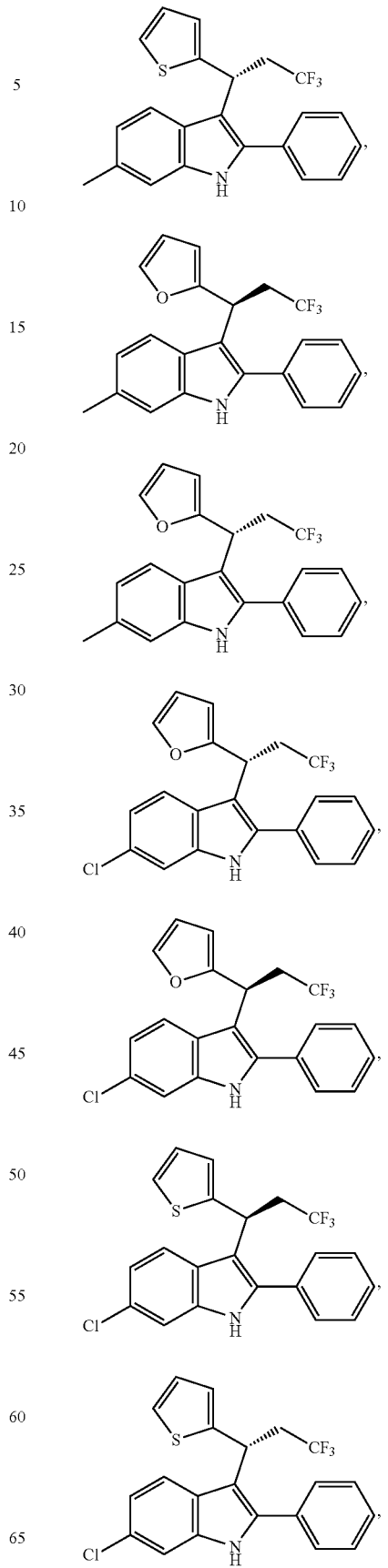

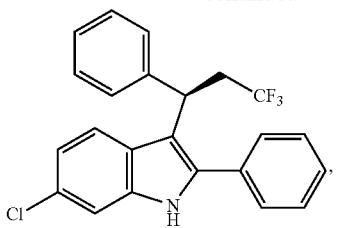
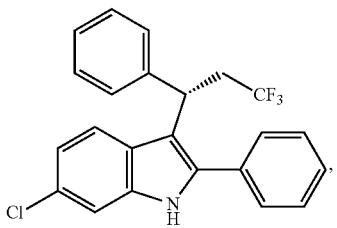
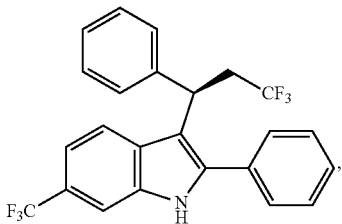
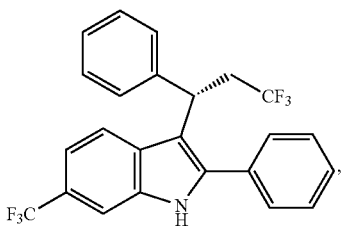
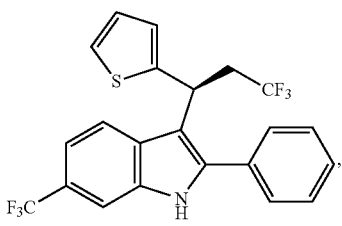
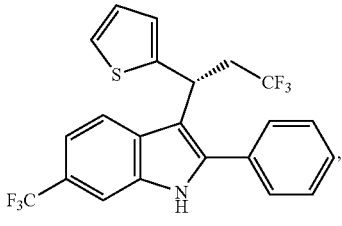
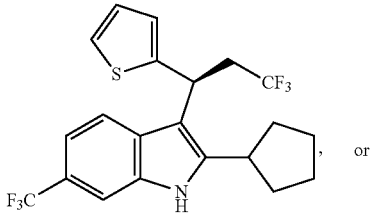

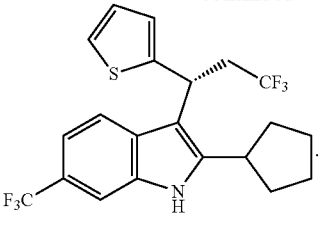 [SMILES: FC(F)(F)CC(c1cccs1)c1c(C2CCCC2)[nH]c2cc(C(F)(F)F)ccc12]

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

In another embodiment, the compounds of the Formula (I) may be prepared, purified, and/or handled as a corresponding salt of the compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19. For example, if the compound of Formula (I) is anionic, or has a functional group which may be anionic (e.g., —COON may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound of Formula (I) is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

In another embodiment, the compounds of the Formula (I) may be prepared, purified, and/or handled as a corresponding solvate of the compound. If the solvent is water, the solvate may be conveniently referred to as a hydrate, for example, a hemi-hydrate, a mono-hydrate, a di-hydrate, a tri-hydrate, etc. Typical procedures for making and identifying suitable hydrates and solvates are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Hydrates and solvates can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.). For the avoidance of doubt, it is understood that the phrase "pharmaceutically acceptable salts and solvates thereof" and the phrase "pharmaceutically acceptable salt or solvate thereof" embrace pharmaceutically acceptable solvates (e.g., hydrates) of the compounds, pharmaceutically acceptable salts of the compounds, as well as pharmaceutically acceptable solvates (e.g., hydrates) of pharmaceutically acceptable salts of the compounds.

In another embodiment, the compound of the Formula (I) may be prepared, purified, and/or handled as a compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality. For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc). For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH—CH$_3$); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.). For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide. For example, a thiol group may be protected as a thioether (—SR), for example, as: a benzyl thioether; an acetamidomethyl ether (—S—CH$_2$NHC(=O)CH$_3$).

In another embodiment, the compound of the Formula (I) may be prepared, purified, and/or handled in the form of a prodrug. Typically, the prodrug is inactive, or less active than the desired active compound, but may provide advantageous handling, administration, or metabolic properties. For example, active compounds which have a hydroxyl or carboxylic acid group may be converted to prodrugs which are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

(III) Compositions

The present disclosure also includes pharmaceutical compositions comprising a compound of the Formula (I), as defined above, or pharmaceutically acceptable salts, solvates, and prodrugs thereof, and a pharmaceutically acceptable carrier or diluent. The compounds are suitably formulated into pharmaceutical compositions for administration to subjects, preferably humans in a biologically compatible form suitable for administration in vivo.

The compositions containing the compounds of Formula (I), can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

In one embodiment, the NN-PAM compounds of the Formula (I) may be administered alone. In another embodiment, the compounds of the Formula (I) may be administered in a pharmaceutical Formulation (e.g., composition, preparation, medicament) comprising at least one NN-PAM compound of the Formula (I), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present disclosure further provides pharmaceutical compositions, as defined above, and methods of making a pharmaceutical composition comprising admixing at least one NN-PAM compound of the Formula (I), as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005. The formulations may be prepared by any methods well known in the art of pharmacy. Such methods include the step of bringing into association the compound with a carrier which constitutes one or more accessory ingredients. In general, the Formulations are prepared by uniformly and intimately bringing into association the compound with carriers (e.g., liquid carriers, finely divided solid carrier, etc.), and then shaping the product, if necessary. The formulation may be prepared to provide for rapid or slow release; immediate, delayed, timed, or sustained release; or a combination thereof.

In another embodiment, formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

In another embodiment, formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

In another embodiment, the compound of the Formula (I) may be dissolved in, suspended in, or admixed with one or more other pharmaceutically acceptable ingredients. The compound may be presented in a liposome or other microparticulate which is designed to target the compound, for example, to blood components or one or more organs.

In another embodiment, formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

In a further embodiment, formulations suitable for buccal administration include mouthwashes, losenges, pastilles, as well as patches, adhesive plasters, depots, and reservoirs. Losenges typically comprise the compound in a flavoured basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

In another embodiment, formulations suitable for sublingual administration include tablets, losenges, pastilles, capsules, and pills.

In a further embodiment, formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

In one embodiment, tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be Formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound of the Formula (I) and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray Formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example, from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

In one embodiment, it will be appreciated by one of skill in the art that appropriate dosages of the compounds of the Formula (I), and compositions comprising the compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular NN-PAM compound, the route of administration, the time of administration, the rate of excretion of the NN-PAM compound, the duration of the treatment, other drugs, compounds, and/or materials used in combination, the severity of the condition, and the species, sex, age, weight, condition, general health, and prior medical history of the patient. The amount of NN-PAM compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the NN-PAM compound of the Formula (I) is in the range of about 50 µg to about 20 mg (more typically about 100 µg to about 10 mg) per kilogram body weight of the subject per day. Where the compound is a salt, an ester, an amide, a prodrug, or the like, the amount administered is calculated on the basis of the parent compound and so the actual weight to be used is increased proportionately In one embodiment, the compounds of the Formula (I) described herein may also be used in combination therapies, e.g., in conjunction with other agents, for example, anti-anginal agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets. It is understood that a particular combination would be at the discretion of the physician who would select dosages using his common general knowledge and dosing regimens known to a skilled practitioner.

In one embodiment, the compositions comprising a compound of the Formula (I) and another active agent may be administered simultaneously or sequentially, and may be administered in individually varying dose schedules and via different routes. For example, when administered sequentially, the compositions can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s). The compositions (i.e., the compound of the Formula (I), plus one or more other agents) may be formulated together in a single dosage form, or alternatively, the individual agents may be formulated separately and presented together in the form of a kit, optionally with instructions for their use.

In one embodiment, other active agents which have shown efficacy in combination with cannabinoid agonists may also be used in combination therapy with a NN-PAM compound of the Formula (I) as described herein. Examples of such drugs include: drugs for the treatment of a range of disorders, including: anxiety and depression, epilepsy, glaucoma, and cancer or cancer-induced vomiting. Thus, in one embodiment, compounds of the Formula (I) may also be used as adjunctive therapy in these and other disorders, allowing for more effective therapy and/or fewer side effects due to lower doses required of each drug.

In one embodiment, analgesics may be used in the treatment of pain, and as such may be used in combination with an NN-PAM compound of the Formula (I) to give an additive therapeutic benefit. Examples of such analgesic drugs include opioids (e.g., codeine morphine, oxycodone, tramadol, pethidine and tapentadol); NSAIDs and COX-2 inhibitors (e.g., naproxen, indomethacin, diclofenac, ibuprofen, aspirin, paracetamol and celecoxib); tricyclic antidepressants (e.g., imipramine, amitriptyline and dibenzepine); potassium channel openers (e.g., flupirtine); atypical or adjuvant analgesics (e.g., duloxetine, amitriptyline, pregabalin and gabapentin); and combinations of the above drug classes and agents.

In another embodiment, anti-depressants may be used in the treatment of depression, and as such may be used in combination with an NN-PAM compound of the Formula (I) to give an additive therapeutic benefit. Examples of such anti-depressants include: serotonin-specific reuptake inhibitors (SSRIs) (e.g., fluoxetine, paroxetine, sertraline); serotonin-norepinephrine reuptake inhibitors (SNRIs) (e.g., venlafaxine, duloxetine, milnacipran); tricyclic antidepressants (e.g., imipramine, amitriptyline and dibenzepine); monoamine oxidase inhibitors (e.g., isocarboxazide, phenelzine, moclobemide).

In another embodiment, anxiolytics may be used in the treatment of anxiety, and as such may be used in combination with an NN-PAM compound of the Formula (I) to give an additive therapeutic benefit. Examples of such anxiolytics include: benzodiazepine sedatives (e.g., diazepam, lorazepam, clonazepam); monoamine oxidase inhibitors (e.g., isocarboxazide, phenelzine, moclobemide); antipsychotics (e.g., quetiapine); serotonin-specific reuptake inhibitors (SSRIs) (e.g., fluoxetine, paroxetine, sertraline); serotonin-norepinephrine reuptake inhibitors (SNRIs) (e.g., venlafaxine, duloxetine, milnacipran); tricyclic antidepressants (e.g., imipramine, amitriptyline and dibenzepine) and anticonvulsants (e.g., pregabalin).

The present disclosure also includes a kit comprising (a) an compound of the Formula (I) as described herein, or a composition comprising an compound as described herein, e.g., preferably provided in a suitable container and/or with suitable packaging; and (b) instructions for use, e.g., written instructions on how to administer the compound or composition. In one embodiment, the kit further comprises one or more (e.g., 1, 2, 3, 4) additional therapeutic agents, as described herein.

The written instructions may also include a list of indications for which the active ingredient is a suitable treatment.

(IV) Processes for the Preparation of Compounds of the Formula (I)

Methods for the chemical synthesis of non-nitro indole-PAM ("NN-PAM") compounds of the Formula (I) (as described herein) are described herein. These and/or other well-known methods may be modified and/or adapted in known ways in order to facilitate the synthesis of additional NN-PAM compounds (as described herein).

In one embodiment, a mono-nitrile NN-PAM, containing a 2-phenylindole group, can be prepared by construction of the required molecular framework prior to cyclisation and indole formation. In the first step a suitable arylketone is deprotonated with a suitable base, and then reacted with a suitable aryl acrylonitrile in a suitable solvent to give the required 3,5-di-substituted 5-oxo-pentanenitrile For example acetophenone is deprotonated with potassium tertiary-butoxide and reacted with cinnamonitrile in THF to give 5-oxo-3,5-diphenylpentanenitrile. The 5-oxo-pentanenitrile can then be condensed with a suitable arylhydrazine in the presence of an acid catalyst, to give the desired 3,5-di-substituted 5-(arylhydrazono)pentanenitrile. For example, 5-oxo-3,5-diphenylpentanenitrile is condensed with m-tolylhydrazine in ethanol with a catalytic amount of acetic acid, to give 3,5-diphenyl-5-(2-m-tolylhydrazono) pentanenitrile. Finally the 3,5-di-substituted 5-(arylhydrazono)pentanenitrile is cyclised to give the desired indole, in the presence of a suitable Lewis acid catalyst. For example the catalyst is zinc chloride and the final product is 3-(6-methyl-2-phenyl-1H-indol-3-yl)-3-phenylpropanenitrile. Different aryl substituents on the final product can be introduced by varying the substituents on the arylketone, the aryl acrylonitrile and the arylhydrazine.

An example of such a method is shown in the scheme 1.

Scheme 1

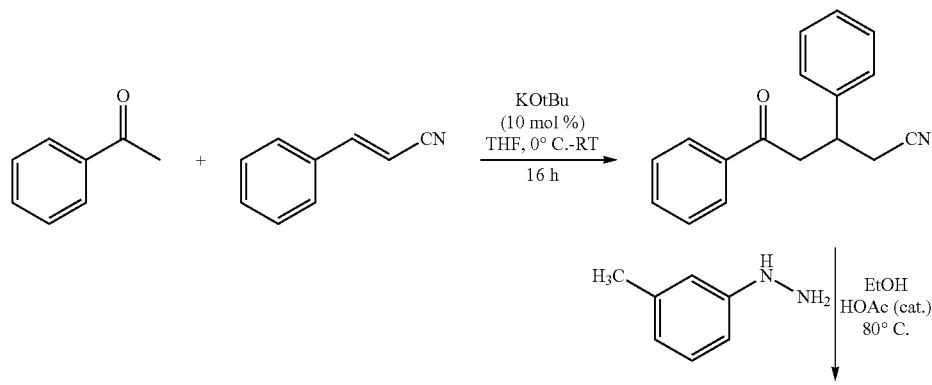

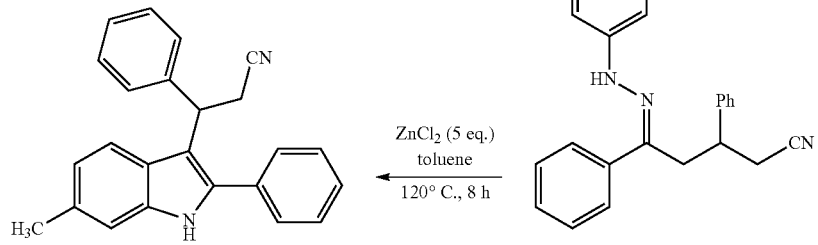

In another embodiment, a bis-nitrile NN-PAM, containing a 2-phenylindole group, can be prepared by generation of the lithium cyanocuprate salt from the protected 3-bromoindole, and reaction with the required aryl malononitrile. For example, the required 2-phenylindole is N-protected as a methoxymethylether by deprotonation with sodium hydride and reaction with chloromethyl methyl ether in THF. The protected indole is brominated with N-bromosuccinimide in dichloromethane. The 3-bromoindole formed is then reacted with butyllithium at −78° C. and reacted with, for example, 2-(thiophen-2-ylmethylene)malononitrile, 2-benzylidenemalononitrile or 2-(pyridin-2-ylmethylene)malononitrile and then deprotected under acidic conditions, to give the desired malononitrile derivative.

An example of such a method is shown in the scheme 2.

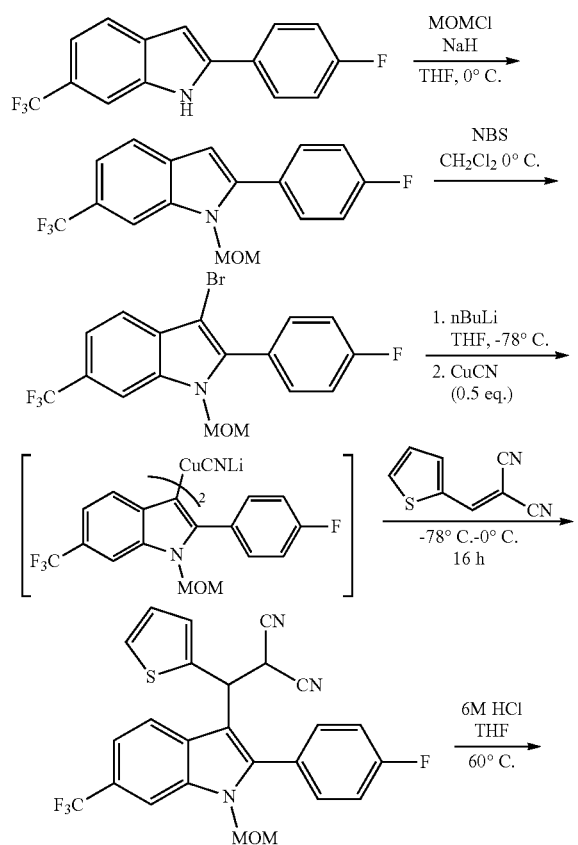

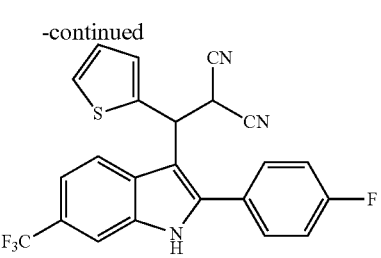

In another embodiment, a trifluoromethyl NN-PAM, containing a 2-phenylindole group, is prepared by generation of an 2-arylacetaldehyde at the 3-position of a suitably protected and substituted indole, and reaction with a nucleophilic fluorinating species. The secondary alcohol formed can then be converted to the ketone or can be esterified and removed under appropriate conditions, to give the 3,3,3-trifluoro-1-arylpropyl derivative.

For example, the required 2-phenylindole is reacted with styrene oxide in the presence of a suitable Lewis acid catalyst, for example indium tribromide, to introduce a 2-phenylethanol at the indole 3-position. The alcohol is temporarily protected with a suitable group, for example as a silyl ether, by reaction with tert-butyldimethysiliyl chloride in the presence of imidazole, prior to N-protection with a MOM group, using chloromethyl methyl ether in THF, as described in scheme 2. Hydrolysis with dilute HCl gives the deprotected alcohol, which can then be oxidised to the required aldehyde, using dimethylphthalate in DCM. The trifluoromethyl group can then be introduced by reaction of this aldehyde with trimethyl(trifluoromethyl)silane in the presence of a caesium fluoride catalyst. Hydrolysis with dilute HCl gives the secondary alcohol which is then used for subsequent reaction.

An example of such a method is shown in the scheme 3.

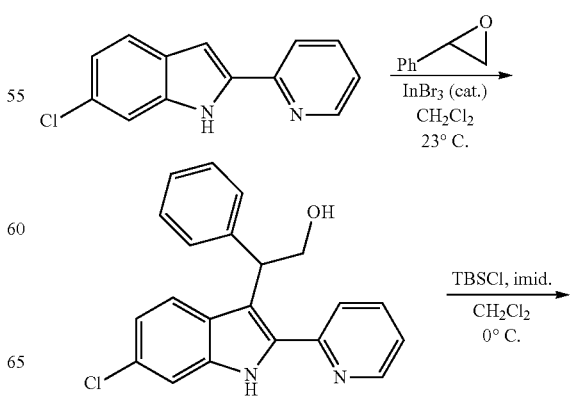

49

-continued

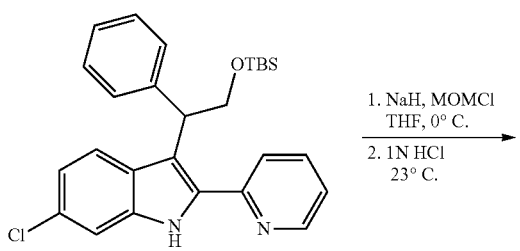

1. NaH, MOMCl
THF, 0° C.
2. 1N HCl
23° C.

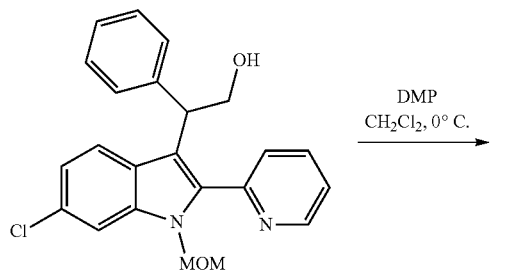

DMP
CH₂Cl₂, 0° C.

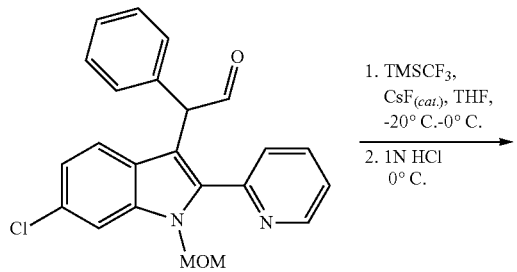

1. TMSCF₃,
CsF(cat.), THF,
−20° C.-0° C.
2. 1N HCl
0° C.

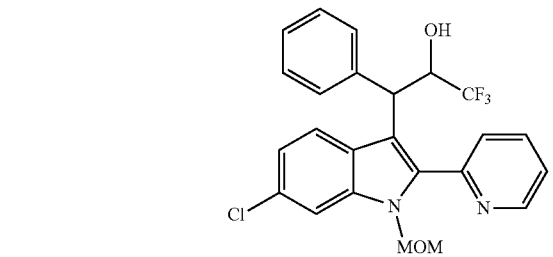

In order to prepare the desired 3-(3,3,3-trifluoro-1-phenylpropyl)indole, the secondary alcohol from scheme 3 can then be deprotonated, for example with n-butyllithium and esterified, for example with O-phenyl carbonochloridothioate, to give a carbothioate, which can then be removed by radical reaction with tributyltin hydride and triethylborane in the presence of air. Finally the MOM protecting group is removed under acid hydrolysis.

An example of such a method is shown in the scheme 4.

Scheme 4

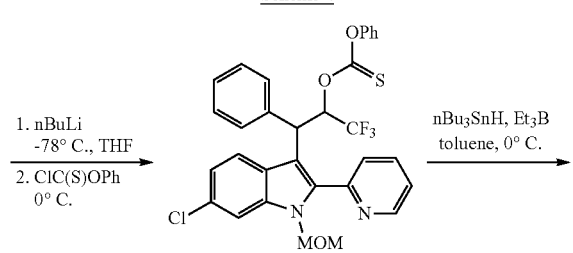

1. nBuLi
−78° C., THF
2. ClC(S)OPh
0° C.

nBu₃SnH, Et₃B
toluene, 0° C.

50

-continued

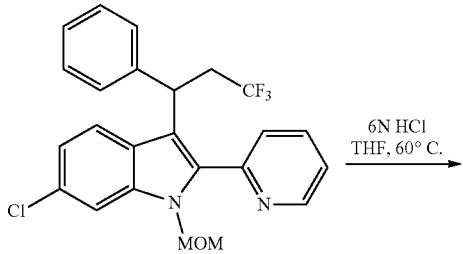

6N HCl
THF, 60° C.

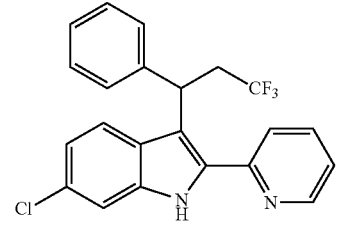

Alternatively, in another embodiment, in order to prepare the desired 3-(1,1,1-trifluoro-3-phenylpropan-2-one)indole, the secondary alcohol from Scheme 3 can be oxidised to the ketone, using dimethylphthalate, and the MOM group removed under acid hydrolysis. An example of such a method is shown in the scheme 5.

Scheme 5

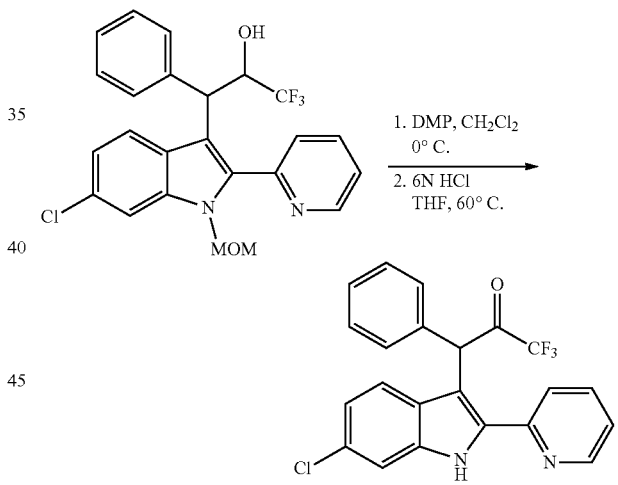

1. DMP, CH₂Cl₂
0° C.
2. 6N HCl
THF, 60° C.

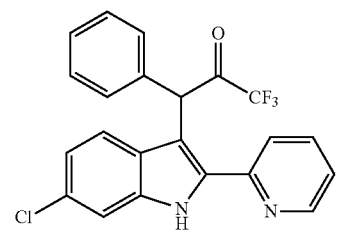

In another embodiment, a wide range of aryl, heteroaryl, alkyl and cycloalkyl groups can be introduced onto the moiety at the indole 3-position, e.g., via formation of a 3-(1-bromopropyl) or 3-(1-tosylpropyl) derivative and subsequent reaction with e.g., a suitable alkylmagnesium bromide or chloride or an aryl or heteroaryl lithium reagent.

For example the N-MOM-protected 3-bromoindole shown in scheme 2 can serve as the starting point for such a synthesis. Initially this is reacted with butyllithium to form the lithium salt, from which a Grignard reagent is then prepared, by reaction with magnesium bromide ethyl etherate, and subsequently reacted with diethyl oxalate, to give the 3-(ethyl-2-oxoacetate) derivative. This is reduced with a suitable reducing agent, for example, with sodium borohydride, to give the 3-(ethyl 2-hydroxy-2-acetate) derivative. The alcohol is protected with a suitable silyl protecting group, for example using triisopropylsilyl trifluoromethanesulfonate and a suitable base, for example, 2,6-lutitine in dichloromethane. The carboxylate is reduced to the aldehyde, for example with lithium triethylborohydride, from which the trifluoromethyl group can now be introduced, for example with trimethyl(trifluoromethyl)silane in the presence of a caesium fluoride catalyst, as shown in scheme 3. The secondary alcohol can then be removed, after formation of the carbothioate, as shown in scheme 3, and the silyl protecting group removed with a suitable source of fluoride, for example tetrabutylammonium fluorine, to give the free alcohol. The alcohol may then be converted into a suitable leaving group, for example a tosyl group, via reaction with toluenesulfonyl chloride, or to a bromo group, via reaction with bromine in the presence of triphenyl phosphine, using the Appel Reaction. The leaving group is then displaced by reaction with a Grignard reagent, for example a Grignard reagent formed from 2-bromofuran, and finally the N-methoxymethylether can be removed under acid hydrolysis, to give, for example, the desired 3-(trifluoromethyl-1-(heteroaryl)propyl)indole.

An example of such a method is shown in the scheme 6.

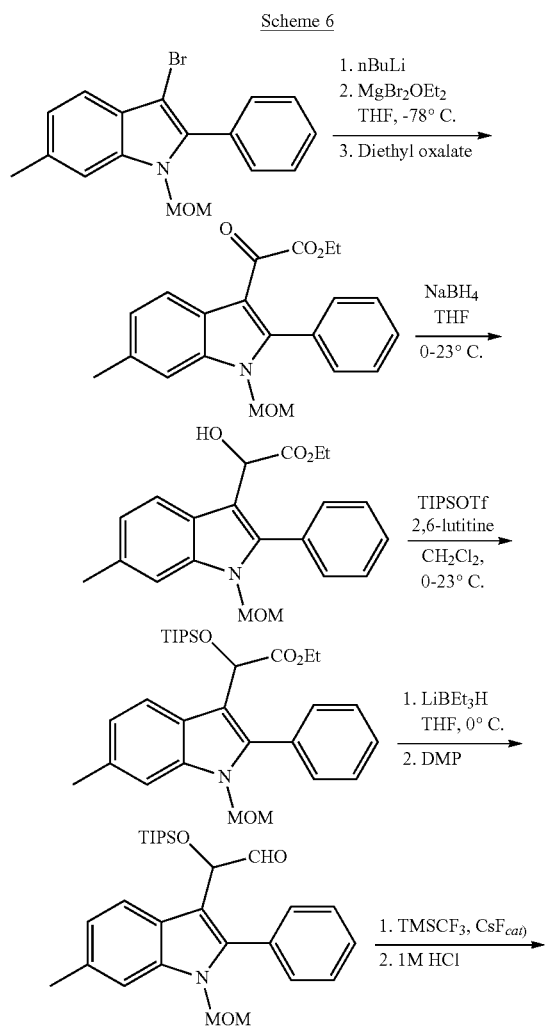

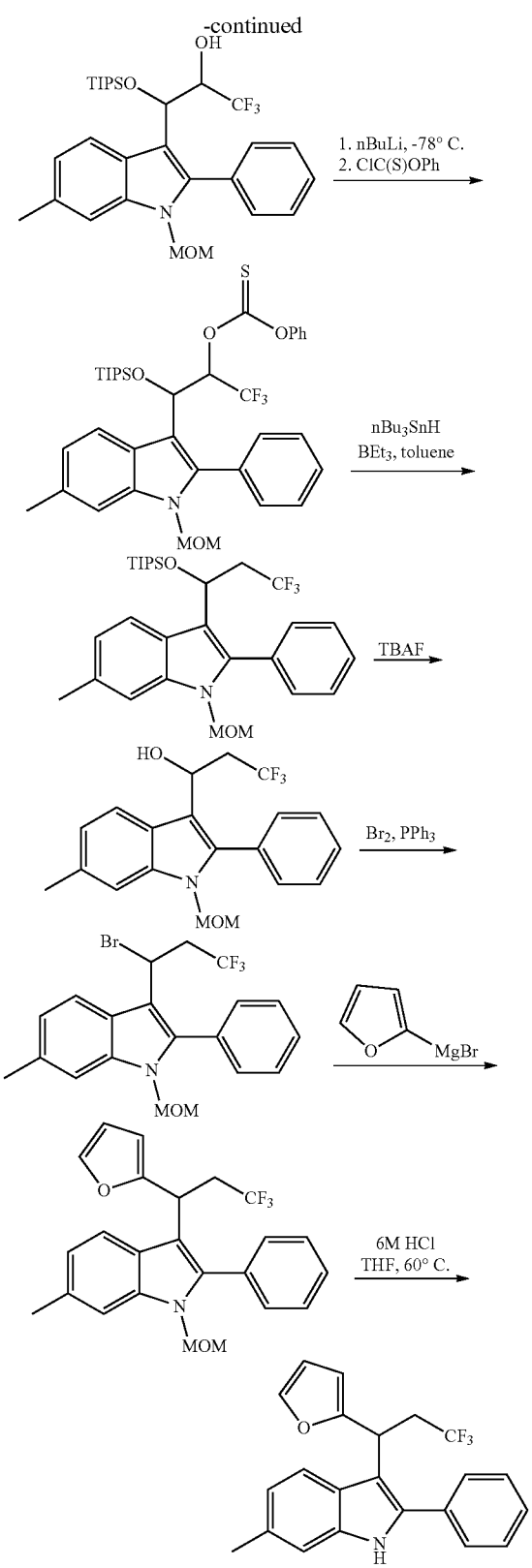

Appropriately-substituted indole starting materials can be prepared from a substituted 2-nitroaniline by the Sandmeyer reaction. For example, the nitroaniline is reacted with acidified sodium nitrite and reacted with potassium iodide, to give a 2-iodoaniline, which can then be cross-coupled with a suitably-substituted acetylene, using the Sonogashira reaction. For example ethynylbenzene, to give a 2-nitro-1-(phenylethynyl)benzene; ethynylcyclohexane, to give a 1-(cyclohexylethynyl)-2-nitrobenzene; or ethynylcyclohexane to give a 1-(cyclopentylethynyl)-2-nitrobenzene. Reduction of the nitro group, for example with $SnCl_2$, gives the amine which, in the presence of a suitable catalyst, for example $ZnBr_2$ in refluxing toluene, can be cyclised to give the desired indole. The resultant indole can then be used in the reactions shown in schemes 2, 3 and 6, giving access to derivatives with a range of substituents at the indole -2, -4, -5, -6 and -7 positions.

An example of such a method is shown in the scheme 7.

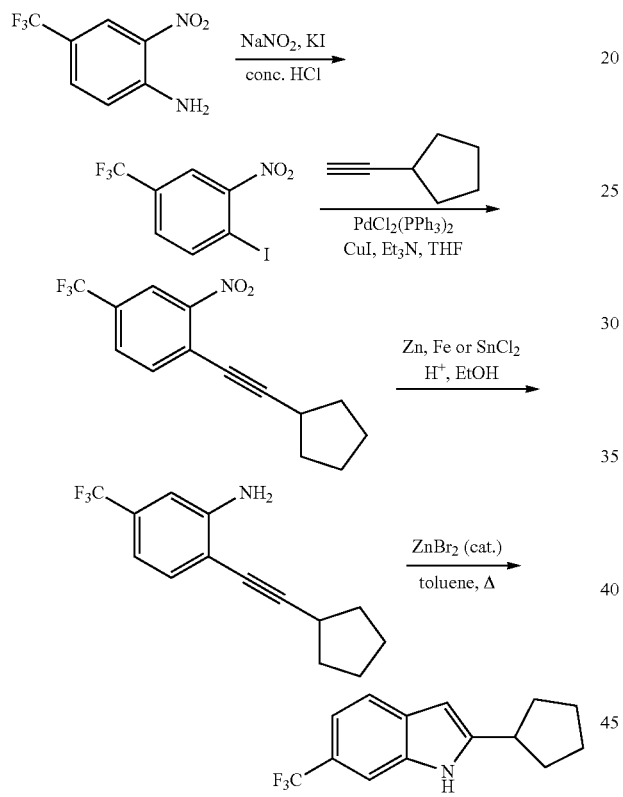

Alkyl and cycloalkyl groups can be introduced onto the moiety at the indole 3-position via conjugate addition of α,β-unsaturated ester with organocopper reagents. The N-MOM-protected 3-(ethyl-2-oxoacetate) indole serves as the starting point to access the 3-indolyl acrylate, which subsequently reacts with in situ generated cycloalkylcopper reagent to give 3-indolylcyclopropylpropanoate. The carboxylate is fully reduced to primary alcohol followed by re-oxidation to the corresponding aldehyde. The trifluoromethyl group is introduced by reaction of the aldehyde with trimethyl(trifluoromethyl)silane in the presence of a caesium fluoride catalyst as shown in scheme 3. The secondary alcohol is converted to the corresponding thiocarbonate followed by Barton-McCombie deoxygenation reaction with tributyltin hydride and triethylborane under air. Removal of the N-methoxymethyl ether under acidic conditions to give the desired 3-(1-cycloalkyl-4,4,4-trifluorobutan-2-yl)indole.

An example of such a method is shown in the scheme 8.

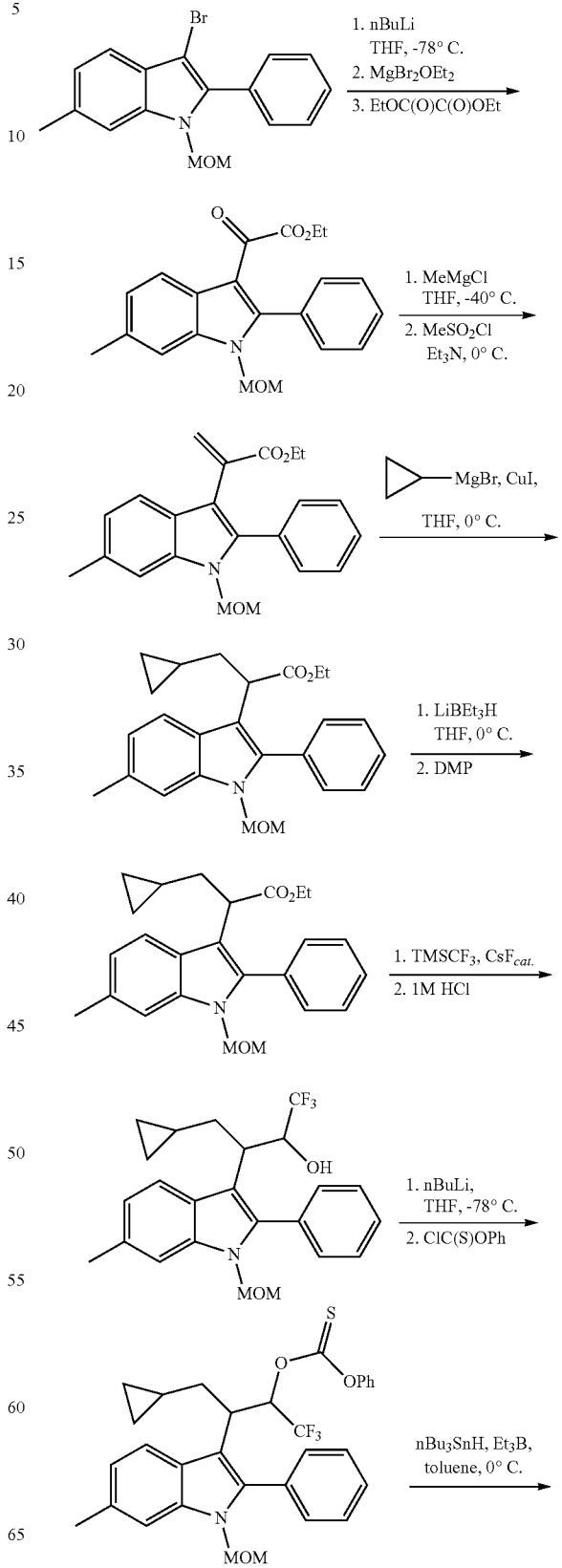

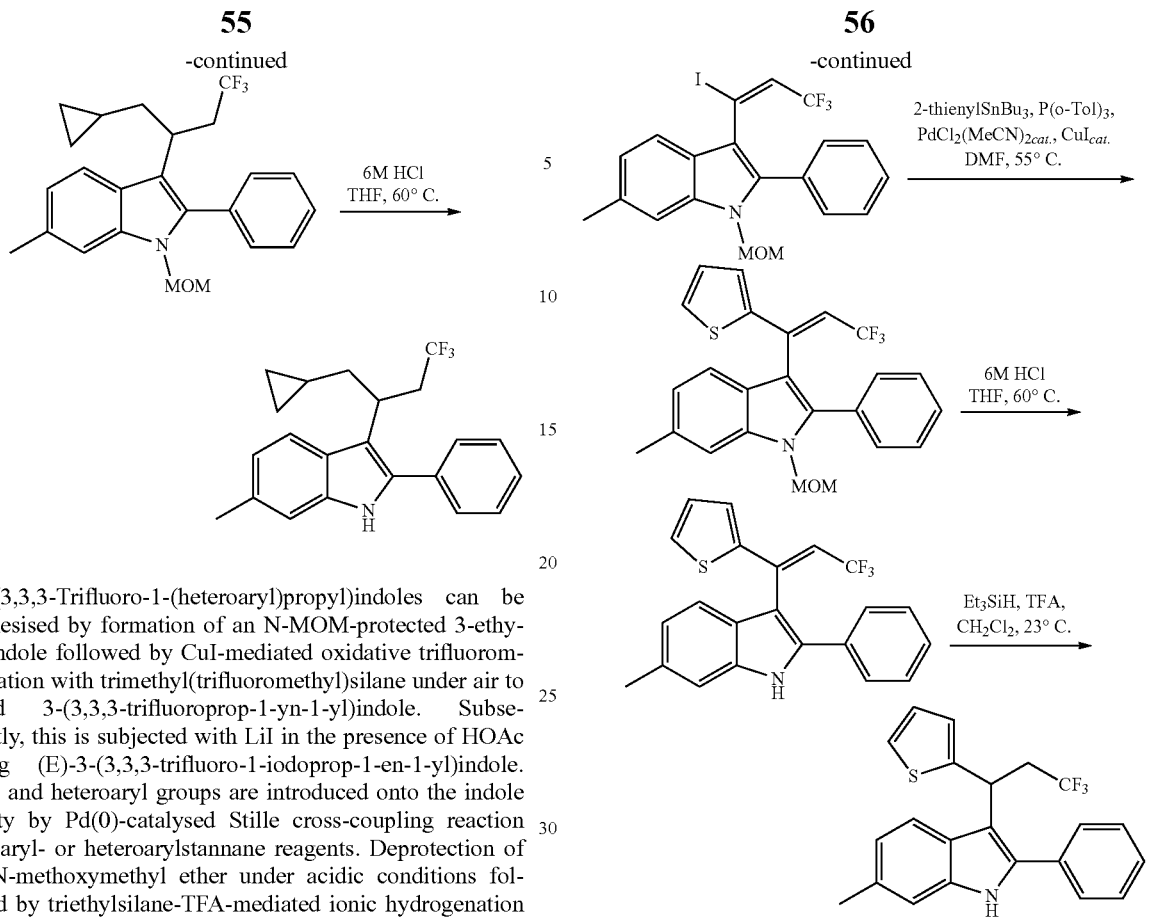

3-(3,3,3-Trifluoro-1-(heteroaryl)propyl)indoles can be synthesised by formation of an N-MOM-protected 3-ethynyl-indole followed by CuI-mediated oxidative trifluoromethylation with trimethyl(trifluoromethyl)silane under air to afford 3-(3,3,3-trifluoroprop-1-yn-1-yl)indole. Subsequently, this is subjected with LiI in the presence of HOAc giving (E)-3-(3,3,3-trifluoro-1-iodoprop-1-en-1-yl)indole. Aryl- and heteroaryl groups are introduced onto the indole moiety by Pd(0)-catalysed Stille cross-coupling reaction with aryl- or heteroarylstannane reagents. Deprotection of the N-methoxymethyl ether under acidic conditions followed by triethylsilane-TFA-mediated ionic hydrogenation give the desired molecules.

An example of such a method is shown in the scheme 9

Scheme 9

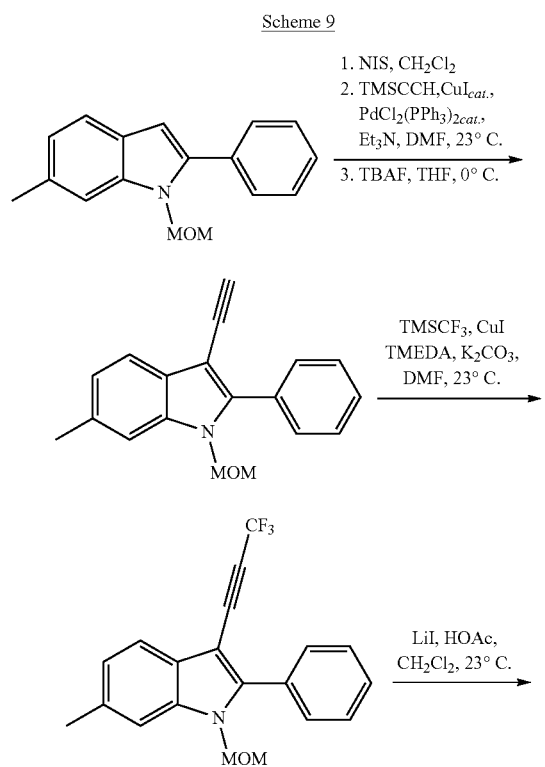

(V) Methods of Medical Treatment and Uses of the Compounds of the Formula (I)

In one embodiment, the compounds of the Formula (I) enhance cannabinoid type 1 receptor signaling. In another embodiment, the compounds of the Formula (I) activate the cannabinoid type 1 receptor, in vitro or in vivo.

In another embodiment of the disclosure, there is also included a method for the treatment of a disease or condition in which modulation of the cannabinoid type 1 receptor is beneficial, comprising administering to a patient in need thereof an effective amount of a compound of the Formula (I) as defined herein. In one embodiment, there is also included a method for the treatment of a disease or condition which is ameliorated by the enhancement of cannabinoid receptor signaling, comprising administering to a patient in need thereof an effective amount of a compound of the Formula (I) as defined herein.

In another embodiment, there is also included a use of a compound of the Formula (I), optionally for the preparation of a medicament, wherein the compound or medicament is for the treatment of a disease or condition in which modulation of the cannabinoid type 1 receptor is beneficial. In another embodiment, there is also included a use of a compound of the Formula (I), optionally for the preparation of a medicament, wherein the compound or medicament is for the treatment of a disease or condition which is ameliorated by the enhancement of cannabinoid receptor signaling.

In one embodiment, the disease or condition is one in which inappropriate cannabinoid type 1 receptor activity is involved.

In one embodiment, the disease or condition is pain, multiple sclerosis, depression, an eating disorder, a cardiovascular disease, non-alcoholic fatty liver disease associated with metabolic syndrome, addiction or a symptom of addiction, a bone disorder, cancer, an inflammatory or autoimmune disease, asthma, a psychiatric disorder, epilepsy, glaucoma, retinopathy, nausea or vomiting associated with cancer chemotherapy, a neurodegenerative disorder, or memory impairment.

In another embodiment, the pain is neuropathic pain, inflammatory pain, pain associated with multiple sclerosis, pain of undefined origin, pain associated with cancer or cancer chemotherapy, pain associated with diabetic neuropathy, or pain associated with surgery.

In a further embodiment, the disease or condition is multiple sclerosis or spasticity associated with multiple sclerosis.

In another embodiment, the eating disorder is cachexia or anorexia associated with cancer chemotherapy or cachexia or anorexia associated with HIV/AIDs.

In another embodiment, the cardiovascular disease is hypertension, congestive heart failure, cardiac hypertrophy, peripheral artery disease, atherosclerosis, stroke, kidney disease, myocardial infarction, steatohepatitis, myocardial reperfusion injury, or cardiotoxicity associated with chemotherapy.

In a further embodiment, the addiction or symptom of addiction is smoking addiction and/or smoking withdrawal, alcohol addiction and/or alcohol withdrawal, or drug addiction and/or drug withdrawal.

In one embodiment, the treatment is smoking cessation therapy.

In one embodiment, the bone disease osteoporosis, Paget's disease, joint destruction, bone loss (associated with rheumatoid arthritis, osteoporosis, cancer-associated bone disease, or Paget's disease of bone), neoplasia of bones, aseptic loosening of prosthetic implants, or bone related cancer.

In a further embodiment, the cancer is breast cancer.

In another embodiment, the inflammatory or autoimmune disease is rheumatoid arthritis, inflammatory bowel disease, psoriatic arthritis, chronic obstructive pulmonary disease, ankylosing spondylitis, an immune response leading to organ or graft rejection following transplant, or psoriasis.

In one embodiment, the psychiatric disorder is anxiety (panic disorder, social anxiety disorder, past-traumatic stress disorder), mania or schizophrenia.

In a further embodiment, the neurodegenerative disorder is Parkinson's disease, Alzheimer's disease, dementia, Huntington's disease, or amyotrophic lateral sclerosis.

In another embodiment of the disclosure, the compounds of the Formula (I) described herein may also be used as part of an in vitro assay, for example, in order to determine whether a candidate host is likely to benefit from treatment with the compound in question.

In another embodiment, the compounds of the Formula (I) may also be used as a standard, for example, in an assay, in order to identify other compounds, other CB1 activators, etc.

The NN-PAM compound or pharmaceutical composition comprising the NN-PAM compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one embodiment, the route of administration is oral (e.g., by ingestion).

In one embodiment, the route of administration is parenteral (e.g., by injection).

EXAMPLES

The following examples are provided solely to illustrate the present disclosure and are not intended to limit the scope of the disclosure, as described herein.

Chemical Synthesis

Synthesis 1—5-Oxo-3,5-diphenylpentanenitrile (1)

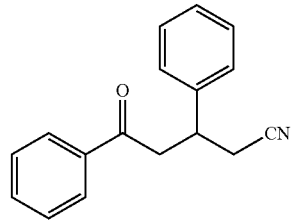 [SMILES: N#CCC(CC(=O)c1ccccc1)c1ccccc1]

To a solution of acetophenone (1.12 g, 9.32 mmol) in THF (5 mL) was added cinnamonitrile (1.0 g, 7.74 mmol) and KOtBu (87 mg, 0.775 mmol) at 0° C. The resulting mixture was stirred at 0° C. and allowed to warm to 23° C. for 16 h before it was quenched with a saturated solution of NH$_4$Cl (10 mL) and diluted with CH$_2$Cl$_2$ (10 mL). The layers were separated, and the aqueous layer was extracted with CH$_2$Cl (4×5 mL). The combined organic layers were dried over Na$_2$SO$_4$ and concentrated in vacuo. The residue was purified by flash column chromatography (silica gel, hexanes:EtOAc 5:1) to give compound 1 (1.39 g, 72%) as a pale yellow oil.
$^1$H NMR (400 MHz, CDCl$_3$) δ=8.01-7.95 (m, 2H), 7.64-7.58 (m, 1H), 7.53-7.46 (m, 2H), 7.42-7.34 (m, 4H), 7.34-7.29 (m, 1H), 3.85-3.71 (m, 1H), 3.56 (dd, J=17.8, 7.0 Hz, 1H), 3.49 (dd, J=17.8, 7.0 Hz, 1H), 2.88 (dd, J=16.2, 5.6 Hz, 1H), 2.83 (dd, J=16.2, 5.6 Hz, 1H); $^{13}$C NMR (101 MHz, CDCl$_3$) δ=197.3, 141.3, 136.5, 133.6, 129.1, 128.8, 128.1, 127.7, 127.2, 118.2, 42.8, 36.8, 24.4. m/z (ESI) 250.1 [M+H]$^+$ Synthesis 2—3-Phenyl-3-(2-phenyl-1H-indol-3-yl)propanenitrile (2, ABD1102)

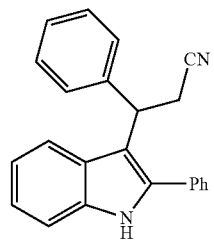 [SMILES: N#CCC(c1ccccc1)c1c(-c2ccccc2)[nH]c2ccccc12]

Method A: To a solution of compound 1 (390 mg, 1.56 mmol) in EtOH (10 mL) was added phenylhydrazine (170 mg, 1.57 mmol) and HOAc (9.6 mg, 9.8 μL, 0.16 mmol). The mixture was heated to 85° C. for 4 h prior to evaporation of the solvent in vacuo to give the corresponding hydrazone, which was used without further purification.

To a solution of the hydrazone in toluene (10 mL) was added $ZnBr_2$ (1.8 g, 8.0 mmol). The resulting mixture was heated to 120° C. for 8 h before it was cooled to 23° C. and quenched with a saturated solution of $NH_4Cl$ (10 mL) and then diluted with $CH_2Cl_2$ (10 mL). The layers were separated, and the aqueous layer was extracted with $CH_2Cl_2$ (4×5 mL). The combined organic layers were dried over $Na_2SO_4$ and concentrated in vacuo. The residue was purified by flash column chromatography (silica gel, hexanes:EtOAc 5:1) to give compound 2 (432 mg, 86%) as a dark orange solid.

$^1$H NMR (400 MHz, $CDCl_3$) δ=8.23 (br s, 1H), 7.57-7.52 (m, 2H), 7.52-7.37 (m, 7H), 7.35 (t, J=7.5 Hz, 2H), 7.31-7.14 (m, 3H), 7.09 (t, J=7.6 Hz, 1H), 4.84 (t, J=8.0 Hz, 1H), 3.30 (dd, J=13.6, 5.0 Hz, 1H), 3.25 (dd, J=13.6, 5.0 Hz, 1H); $^{13}$C NMR (101 MHz, $CDCl_3$) δ=141.6, 136.7, 136.2, 132.4, 129.0, 128.98, 128.8, 128.6, 127.3, 127.0, 126.8, 122.5, 120.1, 120.1, 119.0, 111.8, 111.4, 38.7, 23.7. m/z (ESI) 323.2 $[M+H]^+$

Synthesis 3—3-(6-Methyl-2-phenyl-1H-indol-3-yl)-3-phenylpropanenitrile (3, ABD1132)

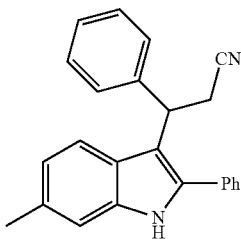 [SMILES: Cc1ccc2c(C(CC#N)c3ccccc3)c(-c3ccccc3)[nH]c2c1]

Using a method analogous to Method A, with 5-oxo-3,5-diphenylpentanenitrile (320 mg, 1.28 mmol), 3-methylphenylhydrazine hydrochloride (204 mg, 1.29 mmol) and HOAc (8 μL, 0.13 mmol). The resulting hydrazone was re-dissolved in toluene (10 mL) and $ZnBr_2$ (1.44 g, 6.4 mmol) was employed. Purification by flash column chromatography (silica gel, hexanes:EtOAc 5:1) gave compound 3 (294 mg, 68%) as a dark red solid.

$^1$H NMR (400 MHz, $CDCl_3$) δ=8.20 (brs, 1H), 7.54-7.50 (m, 2H), 7.50-7.38 (m, 5H), 7.38-7.32 (m, 3H), 7.32-7.25 (m, 1H), 7.22 (s, 1H), 6.96 (dd, J=8.2, 1.0 Hz, 1H), 4.83 (t, J=8.0 Hz, 1H), 3.29 (dd, J=13.6, 4.9 Hz, 1H), 3.24 (dd, J=13.6, 4.9 Hz, 1H), 2.50 (s, 3H); $^{13}$C NMR (101 MHz, $CDCl_3$) δ=141.7, 136.8, 136.1, 132.5, 132.32, 128.9, 128.8, 128.4, 127.3, 127.0, 124.7, 121.8, 119.7, 119.1, 111.6, 111.5, 38.8, 23.8, 21.7. m/z (ESI) 337.2 $[M+H]^+$ Synthesis 4—3-Bromo-1-(methoxymethyl)-2-phenyl-1H-indole (4)

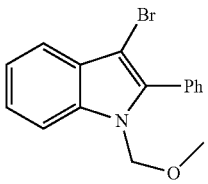 [SMILES: COCn1c(-c2ccccc2)c(Br)c2ccccc21]

Method B: To a solution of 2-phenylindole (661 mg, 3.42 mmol) in DMF (3 mL) was added NaH (141.3 mg, 5.81 mmol, 60% in mineral oil) at 0° C. After stirring at 0° C. for 30 min, chloromethyl methyl ether (413 mg, 390 μL, 5.13 mmol) was added. The resulting reaction mixture was stirred at that temperature and allowed to warm to 23° C. for 3 h before it was quenched with a saturated solution of $NH_4Cl$ (5 mL) and diluted with EtOAc (50 mL). The layers were separated, and the organic layer was extracted with $H_2O$ (4×10 mL). The combined organic layers were dried over $Na_2SO_4$ and concentrated in vacuo to give the corresponding MOM-protected indole, which was used without further purification.

A solution of the crude product in $CH_2Cl_2$ (10 mL) was cooled to 0° C. and N-bromosuccinimide (621 mg, 3.49 mmol) was added. The resulting solution was stirred 0° C. for 1 h prior to quenching with a solution of saturated $Na_2SO_3$ (10 mL) and then diluted with $CH_2Cl_2$ (10 mL). The layers were separated, and the aqueous layer was extracted with $CH_2Cl_2$ (4×5 mL). The combined organic layers were dried over $Na_2SO_4$ and concentrated in vacuo. The residue was purified by flash column chromatography (silica gel, hexanes:EtOAc 8:1) to give compound 4 (995 mg, 92% for 2 steps).

$^1$H NMR (400 MHz, $CDCl_3$) δ=7.66 (ddd, J=7.7, 1.3, 0.7 Hz, 1H), 7.63-7.57 (m, 2H), 7.57-7.48 (m, 4H), 7.39-7.33 (m, 1H), 7.33-7.29 (m, 1H), 5.39 (s, 2H), 3.23 (s, 3H).

Synthesis 5—2-((1-(Methoxymethyl)-2-phenyl-1H-indol-3-yl)(phenyl)methyl)malononitrile (5)

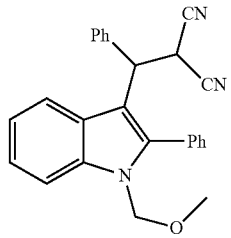 [SMILES: COCn1c(-c2ccccc2)c(C(c2ccccc2)C(C#N)C#N)c2ccccc21]

Method C: To a solution of compound 4 (600 mg, 1.90 mmol) in THF (10 mL) was added a solution of nBuLi (870 μL, 2.09 mmol, 2.4 M in hexanes) at −78° C. The resulting mixture was stirred for 30 min at −78° C. prior to adding CuCN (93.1 mg, 1.04 mmol) and then allowed to warm to −40° C. over 1 h. After which time, the reaction mixture was cooled to −78° C. and a solution of 2-benzylidenemalononitrile (147 mg, 0.95 mmol) in THF (2 mL) was added. The mixture was stirred for 1 h at −78° C. and allowed to warm to 23° C. for 15 h prior to quenching with a saturated solution of $NH_4Cl$ (10 mL). The layers were separated, and the aqueous layer was extracted with $CH_2Cl_2$ (4×5 mL). The combined organic layers were dried over $Na_2SO_4$ and concentrated in vacuo. The residue was purified by flash column chromatography (silica gel, hexanes:EtOAc 6:1) to give compound 5 (247 mg, 66%) as a white solid.

$^1$H NMR (400 MHz, $CDCl_3$) δ=7.70-7.68 (m, 1H), 7.64-7.52 (m, 6H), 7.43 (d, J=8.0 Hz, 1H), 7.40-7.27 (m, 5H), 7.06 (d, J=8.1 Hz, 1H), 5.24 (ABq, J=11.1 Hz, 2H), 4.74 (d,

J=11.2 Hz, 1H), 4.68 (d, J=11.2 Hz, 1H), 3.18 (s, 3H); $^{13}$C NMR (101 MHz, CDCl$_3$) δ=138.2, 137.8, 136.2, 131.4, 129.2, 129.3, 129.0, 128.2, 127.9, 126.1, 122.8, 120.7, 119.5, 112.7, 112.4, 111.9, 108.6, 74.7, 55.8, 44.7, 28.5. m/z (ESI) 392.2 [M+H]$^+$

Synthesis 6—2-(Phenyl(2-phenyl-1H-indol-3-yl)methyl)malononitrile (6, ABD1133)

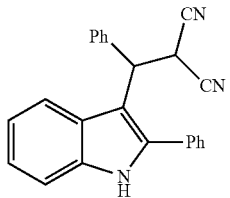 [SMILES: N#CC(C#N)C(c1ccccc1)c1c(-c2ccccc2)[nH]c2ccccc12]

Method D: To a solution of compound 5 (220 mg, 0.56 mmol) in THF (5 mL) was added 6 M HCl (0.5 mL). The mixture was stirred at 60° C. for 16 h prior to quenching with a saturated solution of NaHCO$_3$ (10 mL) and diluting with CH$_2$Cl$_2$ (10 mL). The layers were separated, and the aqueous layer was extracted with CH$_2$Cl$_2$ (4×5 mL). The combined organic layers were dried over Na$_2$SO$_4$ and concentrated in vacuo. The residue was purified by flash column chromatography (silica gel, hexanes:EtOAc 4:1) to give compound 6 (152 mg, 78%) as a white solid.

$^1$H NMR (400 MHz, CDCl$_3$) δ=8.35 (brs, 1H), 7.60 (d, J=7.8 Hz, 1H), 7.56-7.48 (m, 7H), 7.46-7.33 (m, 4H), 7.28 (td, J=7.6, 1.0 Hz, 1H), 7.19 (td, J=7.6, 1.0 Hz, 1H), 5.03 (d, J=10.6 Hz, 1H), 4.76 (d, J=10.6 Hz, 1H); $^{13}$C NMR (101 MHz, CDCl$_3$) δ=138.0, 137.7, 136.1, 131.6, 129.2, 129.2, 129.2, 128.3, 127.8, 126.0, 122.9, 120.8, 119.5, 112.6, 112.3, 111.9, 108.5, 44.7, 28.4. m/z (ESI) 348.1 [M+H]$^+$ Synthesis 7—3-Bromo-1-(methoxymethyl)-6-methyl-2-phenyl-1H-indole (7)

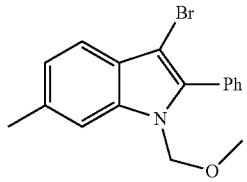

Using a method analogous to Method B, with 6-methyl-2-phenylindole (406 mg, 1.96 mmol), NaH (135 mg, 3.34 mmol, 60% in mineral oil) and chloromethyl methyl ether (237 mg, 224 μL, 2.94 mmol). The solvent was evaporated in vacuo to give a crude product, which was exposed to N-bromosuccinimide (356 mg, 2.00 mmol) in CH$_2$Cl$_2$ (5 mL). Purification by flash column chromatography (silica gel, hexanes:EtOAc 8:1) gave compound 7 (550 mg, 85% for 2 steps).

$^1$H NMR (400 MHz, CDCl$_3$) δ=7.75-7.48 (m, 7H), 7.19 (d, J=8.6 Hz, 1H), 5.38 (s, 2H), 3.26 (s, 3H), 2.62 (s, 3H); $^{13}$C NMR (101 MHz, CDCl$_3$) δ=137.5, 136.0, 133.7, 131.0, 130.9, 130.3, 128.9, 128.6, 128.5, 125.7, 123.3, 119.2, 110.5, 92.6, 75.1, 55.9, 22.1.

Synthesis 8—2-((1-(Methoxymethyl)-6-methyl-2-phenyl-1H-indol-3-yl)(phenyl)methyl)malononitrile (8)

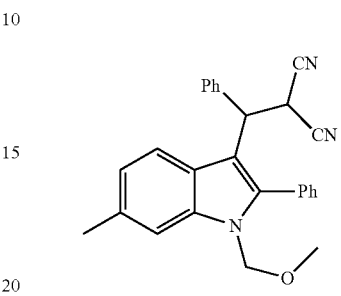

Using a method analogous to Method C, with compound 7 (307 mg, 0.93 mmol), nBuLi (426 μL, 1.02 mmol, 2.40 M in hexanes), CuCN (45.8 mg, 0.51 mmol) and 2-benzylidenemalononitrile (71 mg, 0.46 mmol). Purification by flash column chromatography (silica gel, hexanes:EtOAc 6:1) gave compound 8 (101 mg, 54%) as a white solid.

$^1$H NMR (400 MHz, CDCl$_3$) δ=7.72-7.66 (m, 1H), 7.64-7.52 (m, 5H), 7.46 (d, J=8.1 Hz, 1H), 7.42-7.29 (m, 5H), 7.06 (dd, J=8.2, 0.9 Hz, 1H), 5.27 (ABq, J=11.2 Hz, 2H), 4.75 (d, J=11.3 Hz, 1H), 4.71 (d, J=11.3 Hz, 1H), 3.15 (s, 3H), 2.53 (s, 3H); $^{13}$C NMR (101 MHz, CDCl$_3$) δ=139.8, 137.6, 137.4, 133.1, 130.1, 130.0, 129.5, 129.1, 129.0, 128.8, 128.1, 127.5, 124.7, 123.2, 123.0, 119.0, 112.6, 112.4, 111.1, 110.2, 74.7, 55.8, 44.8, 27.9, 21.8. m/z (ESI) 406.2 [M+H]$^+$

Synthesis 9—2-((6-Methyl-2-phenyl-1H-indol-3-yl)(phenyl)methyl)malononitrile (9, ABD1133)

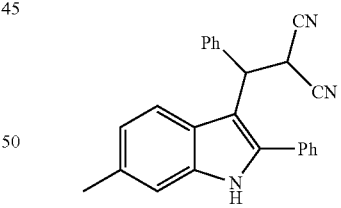

Using a method analogous to Method D, with compound 8 (90 mg, 0.22 mmol). Purification by flash column chromatography (silica gel, hexanes:EtOAc 4:1) gave compound 9 (60 mg, 75%) as a white solid.

$^1$H NMR (400 MHz, CDCl$_3$) δ=8.20 (brs, 1H), 7.70-7.65 (m, 1H), 7.59-7.57 (m, 5H), 7.46 (d, J=7.8 Hz, 1H), 7.44-7.31 (m, 5H), 7.02 (dd, J=8.1, 1.1 Hz, 1H), 4.99 (d, J=10.8 Hz, 1H), 4.73 (d, J=10.8 Hz, 1H), 2.50 (s, 3H); $^{13}$C NMR (101 MHz, CDCl$_3$) δ=137.8, 137.3, 136.6, 132.9, 131.7, 130.0, 129.7, 129.14, 129.11, 129.05, 129.02, 128.2, 127.8, 124.0, 122.5, 119.2, 112.6, 112.3, 111.7, 108.4, 44.7, 28.4, 21.6. m/z (ESI) 362.2 [M+H]$^+$ Synthesis 10—2-((1-(Methoxymethyl)-6-methyl-2-phenyl-1H-indol-3-yl)(thiophen-2-yl)methyl)malononitrile (10)

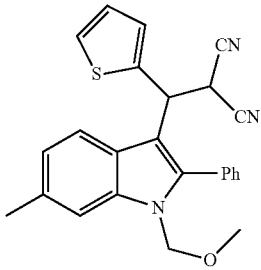 [SMILES: COCn1c(-c2ccccc2)c(C(c2cccs2)C(C#N)C#N)c2ccc(C)cc21]

Using a method analogous to Method C, with compound 7 (420 mg, 1.27 mmol), nBuLi (583 μL, 1.40 mmol, 2.40 M in hexanes), CuCN (63.0 mg, 0.70 mmol) and 2-(2-thienylmethylene)malononitrile (102.5 mg, 0.64 mmol). Purification by flash column chromatography (silica gel, hexanes:EtOAc 5:1) gave compound 10 (152 mg, 58%).

$^1$H NMR (400 MHz, CDCl$_3$) δ=7.74-7.52 (m, 4H), 7.50 (d, J=8.2 Hz, 1H), 7.46-7.36 (m, 2H), 7.29-7.26 (m, 1H), 7.18 (d, J=3.6 Hz, 1H), 7.07 (d, J=8.2 Hz, 1H), 7.01 (dd, J=4.5, 3.6 Hz, 1H), 5.30 (s, 2H), 4.95 (d, J=10.4 Hz, 1H), 4.65 (d, J=10.4 Hz, 1H), 3.16 (s, 3H), 2.54 (s, 3H); $^{13}$C NMR (101 MHz, CDCl$_3$) δ=141.0, 140.0, 137.7, 133.3, 130.0, 129.8, 129.6, 129.1, 128.9, 127.1, 126.1, 126.0, 122.9, 122.7, 119.3, 119.2, 112.4, 111.9, 111.2, 110.0, 74.7, 55.8 40.8, 29.2, 21.9. m/z (ESI) 412.1 [M+H]$^+$

Synthesis 11—2-((6-Methyl-2-phenyl-1H-indol-3-yl)(thiophen-2-yl)methyl)malononitrile (11, ABD1155)

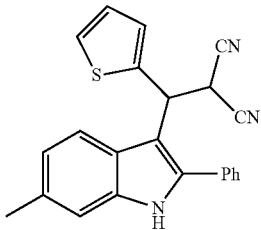 [SMILES: Cc1ccc2c(C(c3cccs3)C(C#N)C#N)c(-c3ccccc3)[nH]c2c1]

Using a method analogous to Method D, with compound 10 (136 mg, 0.33 mmol). Purification by flash column chromatography (silica gel, hexanes:EtOAc 5:1) gave compound 11 (82 mg, 68%) as a white solid.

$^1$H NMR (400 MHz, CDCl$_3$) δ=8.23 (brs, 1H), 7.55-7.46 (m, 6H), 7.31 (dd, J=5.1, 1.2 Hz, 1H), 7.29-7.24 (m, 2H), 7.07-7.01 (m, 2H), 5.23 (d, J=10.4 Hz, 1H), 4.70 (d, J=10.4 Hz, 1H), 2.50 (s, 3H); $^{13}$C NMR (101 MHz, CDCl$_3$) δ=141.2, 137.4, 136.7, 133.1, 131.5, 129.2, 129.1, 127.2, 126.5, 126.2, 123.3, 122.5, 119.3, 112.5, 111.8, 111.7, 108.2, 40.7, 29.5, 21.7. m/z (ESI) 368.1 [M+H]$^+$ Synthesis 12—2-Phenyl-2-(2-phenyl-1H-indol-3-yl)ethan-1-ol (12)

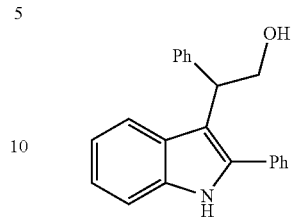

Method E: To a solution of 2-phenylindole (500 mg, 2.59 mmol) in CH$_2$Cl$_2$ (10 mL), was added 2-phenyloxirane (200 μL, 210.6 mg, 1.75 mmol) and InBr$_3$ (6 mg, 0.017 mmol) at 23° C. The resulting red solution was stirred at ° C. for 16 h before it was quenched with a saturated solution of NH$_4$Cl (10 mL) and diluted with CH$_2$Cl$_2$ (10 mL). The layers were separated, and the aqueous layer was extracted with CH$_2$Cl$_2$ (4×5 mL). The combined organic layers were dried over Na$_2$SO$_4$ and concentrated in vacuo. The residue was purified by flash column chromatography (silica gel, hexanes:EtOAc 3:1) to give compound 12 (450 mg, 82%) as a pale yellow oil.

$^1$H NMR (400 MHz, CDCl$_3$) δ=8.30 (brs, 1H), 7.62 (d, J=8.4 Hz, 1H), 7.59-7.51 (m, 2H), 7.49-7.36 (m, 6H), 7.35-7.28 (m, 2H), 7.27-7.21 (m, 2H), 7.11 (t, J=7.6 Hz, 1H), 4.69 (dd, J=9.0, 6.6 Hz, 1H), 4.44 (dd, J=10.6, 9.0 Hz, 1H), 4.34 (dd, J=10.6, 6.6 Hz, 1H); $^{13}$C NMR (101 MHz, CDCl$_3$) δ=141.8, 137.7, 136.3, 132.7, 128.8, 128.5, 128.34, 128.27, 128.0, 127.6, 126.4, 122.4, 120.8, 120.0, 111.2, 110.9, 65.5, 45.2. m/z (ESI) 336.1 [M+Na]$^+$ Synthesis 13—2-(1-(Methoxymethyl)-2-phenyl-1H-indol-3-yl)-2-phenylacetaldehyde (13)

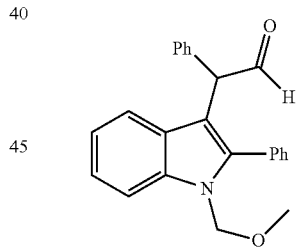

Method F: To a solution of compound 12 (450 mg, 1.44 mmol) in CH$_2$Cl$_2$ (5 mL), was added imidazole (196 mg, 2.88 mmol) and tert-butyldimethylsilyl chloride (271 mg, 1.80 mmol) at 0° C. The resulting mixture was stirred ° C. and allowed to warm to 23° C. for 6 h before it was quenched with a saturated solution of NaHCO$_3$ (5 mL) and diluted with CH$_2$Cl$_2$ (10 mL). The layers were separated, and the aqueous layer was extracted with CH$_2$Cl$_2$ (4×5 mL). The combined organic layers were dried over Na$_2$SO$_4$ and concentrated in vacuo. The residue was re-dissolved in DMF (2 mL) and added NaH (88 mg, 2.17 mmol, 60% in mineral oil) at 0° C. After stirring at ° C. for 30 min, chloromethyl methyl ether (145 mg, 137 μL, 1.80 mmol) was added. The resulting reaction mixture was stirred at ° C. and allowed to warm to 23° C. for 3 h before it was quenched with a saturated solution of NH$_4$Cl (5 mL) and diluted with EtOAc (50 mL). The layers were separated, and the organic layer was extracted with H₂O (4×10 mL). The combined organic layers were dried over Na₂SO₄ and concentrated in vacuo. The resulting crude product was exposed to MeOH—CH₂Cl₂ (5 mL, 1:10, v/v) and p-toluenesulfonic acid monohydrate (28 mg, 0.147 mmol) was added at 23° C. The resulting mixture was stirred for 4 h prior to quenching with a saturated solution of NaHCO₃ (5 mL) and diluted with CH₂Cl₂ (10 mL). The layers were separated, and the aqueous layer was extracted with CH₂Cl₂ (4×5 mL). The combined organic layers were dried over Na₂SO₄ and concentrated in vacuo. The residue was passed through a short plug of silica gel (EtOAc) and concentrated in vacuo prior to use.

To a solution of the crude alcohol in CH₂Cl₂ (5 mL) was added Dess-Martin periodinane (762 mg, 1.80 mmol) at 23° C. The reaction mixture was stirred for 16 h before it was quenched with a saturated solution of Na₂SO₃ (5 mL). The resulting mixture was extracted with CH₂Cl₂ (3×10 mL), combined organic layers were dried over Na₂SO₄ and concentrated in vacuo. The residue was purified by flash column chromatography (silica gel, hexanes:EtOAc 9:1→5:1) to give compound 13 (316 mg, 62% for 4 steps).

¹H NMR (400 MHz, CDCl₃) δ=10.04 (d, J=2.3 Hz, 1H), 7.64 (d, J=7.6 Hz, 1H), 7.55-7.44 (m, 5H), 7.42 (d, J=7.6 Hz, 1H), 7.39-7.30 (m, 4H), 7.29-7.24 (m, 2H), 7.19 (t, J=7.6 Hz, 1H), 5.41 (s, 2H), 5.03 (d, J=2.3 Hz, 1H), 3.29 (s, 3H); ¹³C NMR (101 MHz, CDCl₃) δ=198.7, 140.9, 137.3, 136.7, 131.0, 130.4, 129.1, 128.73, 128.69, 128.6, 127.21, 127.17, 122.9, 121.1, 120.5, 110.6, 108.4, 74.9, 56.1, 56.0. m/z (ESI) 378.1 [M+Na]⁺

Synthesis 14—1,1,1-Trifluoro-3-(1-(methoxymethyl)-2-phenyl-1H-indol-3-yl)-3-phenylpropan-2-ol (14)

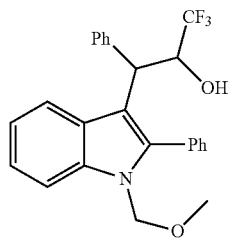 [SMILES: COCn1c(-c2ccccc2)c(C(c2ccccc2)C(O)C(F)(F)F)c2ccccc21]

Method G: To a solution of compound 13 (266 mg, 0.748 mmol) in THF (5 mL) was added CsF (23 mg, 0.151 mmol) and trimethyl(trifluoromethyl)silane (160 mg, 166 μL, 1.123 mmol) at 0° C. The resulting mixture was stirred The resulting mixture was stirred at 0° C. for 3 h before addition of 1 M HCl (1 mL) and the mixture then stirred at 23° C. for a further 1 h. After which, the reaction mixture was diluted with CH₂Cl₂ (10 mL) and H₂O (10 mL). The layers were separated, and the aqueous layer was extracted with CH₂Cl₂ (4×5 mL). The combined organic layers were dried over Na₂SO₄ and concentrated in vacuo. The residue was passed through a short plug of silica gel (EtOAc) and concentrated in vacuo to give compound 14 (245 mg, 86%; ca. 7:1 mixture of inseparable diastereoisomers determined by ¹H NMR) as a pale yellow oil. The spectroscopic data of the major diastereomer is reported.

¹H NMR (400 MHz, CDCl₃) δ=7.99 (d, J=7.8 Hz, 1H), 7.64-7.43 (m, 5H), 7.38-7.31 (m, 4H), 7.30-7.13 (m, 4H), 5.25 (ABq, J=10.6 Hz, 2H), 5.06-4.96 (m, 1H), 4.46 (d, J=7.7 Hz, 1H), 3.12 (s, 3H); ¹⁹F NMR (376 MHz, CDCl₃) δ=−76.26 (d, J=6.8 Hz, 3F).

Synthesis 15—O-Phenyl O-(1,1,1-trifluoro-3-(1-(methoxymethyl)-2-phenyl-1H-indol-3-yl)-3-phenyl-propan-2-yl) carbonothioate (15)

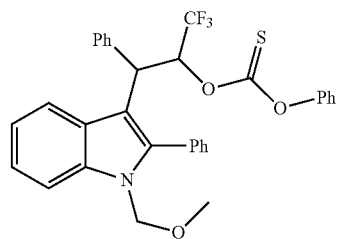 [SMILES: COCn1c(-c2ccccc2)c(C(c2ccccc2)C(OC(=S)Oc2ccccc2)C(F)(F)F)c2ccccc21]

Method H: To a solution of compound 14 (200 mg, 0.47 mmol) in THF (5 mL), was added nBuLi (370 μL, 0.59 mmol, 1.6 M in hexanes) at −78° C. The resulting solution was stirred at 78° C. for 30 min before a solution of O-phenyl chlorothionoformate (100 μL, 125 mg, 0.723 mmol) in THF (1 mL) was added. The resulting mixture was allowed to warm to 0° C. and stirred for 3 h before it was quenched with a saturated solution of NH₄Cl (10 mL) and diluted with CH₂Cl₂ (10 mL). The layers were separated, and the aqueous layer was extracted with CH₂Cl₂ (4×5 mL). The combined organic layers were dried over Na₂SO₄ and concentrated in vacuo. The residue was purified by flash column chromatography (silica gel, hexanes:EtOAc 10:1→5:1) to give compound 15 (243 mg, 92%; mixture of inseparable diastereoisomers) as a yellow oil.

¹H NMR (400 MHz, CDCl₃) δ=8.16 (d, J=7.4 Hz, 1H), 7.61-7.49 (m, 5H), 7.46-7.40 (m, 3H), 7.39-7.32 (m, 5H), 7.30-7.23 (m, 3H), 7.10 (dq J=11.0, 6.6 Hz, 1H), 6.82-6.77 (m, 2H), 5.28 (s, 2H), 4.68 (d, J=11.0 Hz, 1H), 3.12 (s, 3H); ¹⁹F NMR (376 MHz, CDCl₃) δ=−78.87 (d, J=6.6 Hz, 3F).

Synthesis 16—1-(Methoxymethyl)-2-phenyl-3-(3,3,3-trifluoro-1-phenylpropyl)-1H-indole (16)

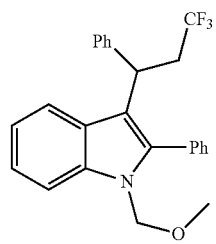 [SMILES: COCn1c(-c2ccccc2)c(C(CC(F)(F)F)c2ccccc2)c2ccccc21]

Method I: To a solution of compound 15 (105 mg, 0.187 mmol) in toluene (5 mL), was added tri-n-butyltin hydride (109 mg, 100 μL, 0.374 mmol) and Et₃B (95 μL, 0.095 mmol, 1.0 M in hexanes) at 0° C. under an atmosphere of air (1 atm). The resulting solution was stirred at 0° C. for 3 h before the solvent was concentrated in vacuo. Purification by flash column chromatography (silica gel, hexanes:EtOAc 10:1) gave compound 16 (27 mg, 35%) as a pale yellow oil.

¹H NMR (400 MHz, CDCl₃) δ=7.61 (d, J=8.1 Hz, 1H), 7.55 (d, J=8.5 Hz, 1H), 7.52-7.47 (m, 3H), 7.44-7.34 (m,

2H), 7.32-7.23 (m, 5H), 7.21-7.14 (m, 2H), 5.29 (ABq, J=11.1 Hz, 2H), 4.49 (dd, J=9.1, 5.2 Hz, 1H), 3.22-3.08 (m+s, 4H), 3.07-2.91 (m, 1H); ¹⁹F NMR (376 MHz, CDCl₃) δ=−64.22 (t, J=10.7 Hz, 3F).

Synthesis 17—2-Phenyl-3-(3,3,3-trifluoro-1-phenyl-propyl)-1H-indole (17, ABD1137)

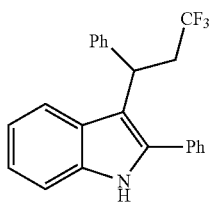 [SMILES: FC(F)(F)CC(c1ccccc1)c1c(-c2ccccc2)[nH]c2ccccc12]

Method J: To a solution of compound 16 (20 mg, 0.049 mmol) in THF (3 mL), was added 6 M HCl (0.2 mL). The mixture was stirred at 60° C. for 16 h prior to quenching with a saturated solution of NaHCO₃ (5 mL) and diluted with CH₂Cl₂ (10 mL). The layers were separated, and the aqueous layer was extracted with CH₂Cl₂ (4×5 mL). The combined organic layers were dried over Na₂SO₄ and concentrated in vacuo. The residue was purified by flash column chromatography (silica gel, hexanes:EtOAc 5:1) to give compound 17 (11 mg, 58%) as a white solid.

¹H NMR (400 MHz, CDCl₃) δ=8.11 (brs, 1H), 7.58 (d, J=8.0 Hz, 1H), 7.52-7.41 (m, 5H), 7.40-7.35 (m, 2H), 7.34-7.27 (m, 3H), 7.25-7.19 (m, 2H), 7.13 (ddd, J=8.1, 7.1, 1.0 Hz, 1H), 4.79 (dd, J=8.8, 5.3 Hz, 1H), 3.25-3.12 (m, 1H), 3.12-2.99 (m, 1H); ¹⁹F NMR (376 MHz, CDCl₃) δ=−64.39 (t, J=10.8 Hz, 3F). m/z (ESI) 366.2 [M+H]⁺

Synthesis 18—2-(6-Methyl-2-phenyl-1H-indol-3-yl)-2-phenylethan-1-ol (18)

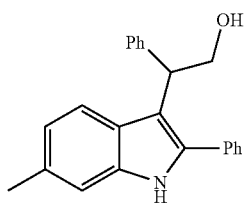 [SMILES: Cc1ccc2c(C(CO)c3ccccc3)c(-c3ccccc3)[nH]c2c1]

Using a method analogous to Method E, with 6-methyl-2-phenylindole (450 mg, 2.17 mmol), 2-phenyloxirane (165 µL, 174.0 mg, 1.45 mmol) and InBr₃ (5.3 mg, 0.015 mmol). Purification by flash column chromatography (silica gel, hexanes:EtOAc 3:1) gave compound 18 (379 mg, 80%) as a pale yellow oil.

¹H NMR (400 MHz, CDCl₃) δ=8.21 (brs, 1H), 7.57-7.48 (m, 3H), 7.47-7.36 (m, 5H), 7.35-7.27 (m, 2H), 7.26-7.20 (m, 2H), 6.94 (d, J=8.1 Hz, 1H), 4.68 (dd, J=8.5, 7.6 Hz, 1H), 4.42 (dd, J=10.2, 9.2 Hz, 1H), 4.37-4.26 (m, 1H), 2.51 (s, 3H); ¹³C NMR (101 MHz, CDCl₃) δ=141.9, 137.1, 136.8, 132.8, 132.3, 128.8, 128.7, 128.5, 128.1, 128.0, 126.4, 125.4, 121.8, 120.5, 111.22, 110.7, 65.6, 45.2, 21.7. m/z (ESI) 328.2 [M+H]⁺

Synthesis 19—2-(1-(Methoxymethyl)-6-methyl-2-phenyl-1H-indol-3-yl)-2-phenylacetaldehyde (19)

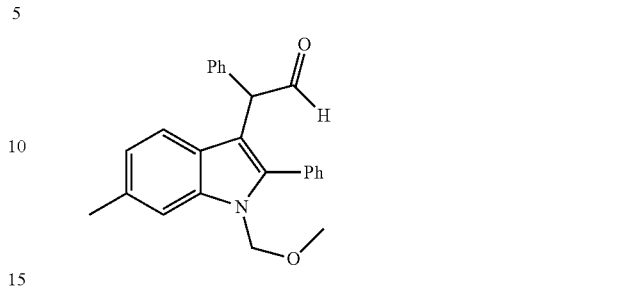

Using a method analogous to Method F, with compound 18 (370 mg, 1.13 mmol), imidazole (154 mg, 2.26 mmol), tert-butyldimethylsilyl chloride (213 mg, 1.41 mmol), NaH (69 mg, 1.70 mmol, 60% in mineral oil), chloromethyl methyl ether (114 mg, 107 µL, 1.42 mmol) and p-toluene-sulfonic acid monohydrate (21 mg, 0.11 mmol). After the residue was passed through a short plug of silica gel (EtOAc) and concentrated in vacuo, the resulting crude alcohol was exposed to Dess-Martin periodinane (600 mg, 1.41 mmol) at 23° C. for 16 h. Purification by flash column chromatography (silica gel, hexanes:EtOAc 10:1→6:1) gave compound 19 (230 mg, 55% for 4 steps).

¹H NMR (400 MHz, CDCl₃) δ=10.06 (d, J=2.1 Hz, 1H), 7.62-7.58 (m, 2H), 7.53-7.44 (m, 4H), 7.42-7.40 (m, 1H), 7.37-7.29 (m, 3H), 7.29-7.24 (m, 2H), 7.16 (t, J=7.6 Hz, 1H), 5.38 (s, 2H), 5.00 (d, J=2.1 Hz, 1H), 3.29 (s, 3H), 2.52 (s, 3H); ¹³C NMR (101 MHz, CDCl₃) δ=198.2, 140.8, 137.5, 136.6, 131.1, 130.3, 129.1, 128.8, 128.69, 128.6, 127.2, 127.0, 122.8, 121.0, 120.3, 110.7, 108.3, 74.6, 56.2, 56.0, 21.9. m/z (ESI) 392.2 [M+Na]⁺

Synthesis 20—1,1,1-Trifluoro-3-(1-(methoxymethyl)-6-methyl-2-phenyl-1H-indol-3-yl)-3-phenyl-propan-2-ol (20)

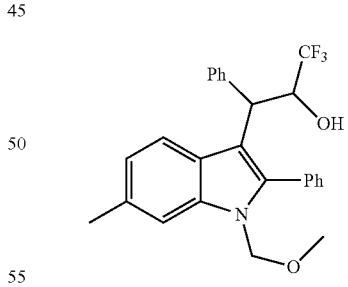

Using a method analogous to Method G, with compound 19 (160 mg, 0.433 mmol), CsF (13 mg, 0.087 mmol) and trimethyl(trifluoromethyl)silane (93 mg, 97 µL, 0.656 mmol). The residue was passed through a short plug of silica gel (EtOAc) and concentrated in vacuo to give compound 20 (152 mg, 80%; ca. 8:1 mixture of inseparable diastereoisomers determined by ¹H NMR).

¹H NMR (400 MHz, CDCl₃) δ=8.02 (d, J=7.6 Hz, 1H), 7.62-7.40 (m, 4H), 7.35-7.31 (m, 4H), 7.30-7.13 (m, 4H), 5.24 (ABq, J=10.4 Hz, 2H), 5.04-4.94 (m, 1H), 4.48 (d,

J=7.5 Hz, 1H), 3.13 (s, 3H), 2.51 (s, 3H); ¹⁹F NMR (376 MHz, CDCl₃) δ=−76.34 (d, J=6.8 Hz, 3F).

Synthesis 21—O-phenyl O-(1,1,1-trifluoro-3-(1-(methoxymethyl)-6-methyl-2-phenyl-1H-indol-3-yl)-3-phenylpropan-2-yl) carbonothioate (21)

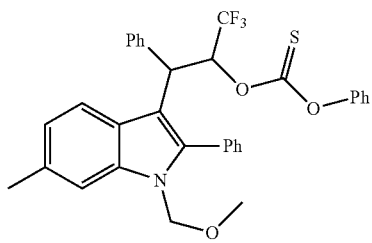 [SMILES: COCn1c(-c2ccccc2)c(C(c2ccccc2)C(OC(=S)Oc2ccccc2)C(F)(F)F)c2ccc(C)cc21]

Using a method analogous to Method H, with compound 20 (140 mg, 0.319 mmol), n-BuLi (166 μL, 0.398 mmol, 2.4 M in hexanes) and O-phenyl chlorothionoformate (66 μL, 82 mg, 0.477 mmol). Purification by flash column chromatography (silica gel, hexanes:EtOAc 10:1→5:1) gave compound 21 (154 mg, 84%; mixture of inseparable diastereoisomers) as a yellow oil.

¹H NMR (400 MHz, CDCl₃) δ=8.05 (d, J=8.2 Hz, 1H), 7.58-7.49 (m, 3H), 7.48-7.42 (m, 3H), 7.41-7.33 (m, 4H), 7.32-7.22 (m, 4H), 7.18 (d, J=8.7 Hz, 1H), 7.10 (dq, J=11.2, 6.2 Hz, 1H), 6.83-6.75 (m, 2H), 5.27 (s, 2H), 4.67 (d, J=11.2 Hz, 1H), 3.12 (s, 3H), 2.57 (s, 3H); ¹⁹F NMR (376 MHz, CDCl₃) δ=−72.90 (d, J=6.2 Hz, 3F).

Synthesis 22—1-(Methoxymethyl)-6-methyl-2-phenyl-3-(3,3,3-trifluoro-1-phenylpropyl)-1H-indole (22)

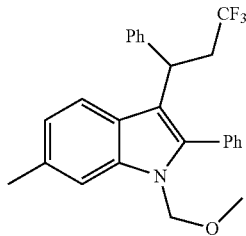

Using a method analogous to Method I, with compound 21 (88 mg, 0.153 mmol), tri-n-butyltin hydride (89 mg, 82 μL, 0.306 mmol) and BEt₃ (30 μL, 0.03 mmol, 1.0 M in hexanes). Purification by flash column chromatography (silica gel, hexanes:EtOAc 10:1) gave compound 22 (25 mg, 38%) as a pale yellow oil.

¹H NMR (400 MHz, CDCl₃) δ=7.54-7.45 (m, 4H), 7.43-7.32 (m, 3H), 7.30-7.23 (m, 4H), 7.21-7.15 (m, 1H), 7.02 (dd, J=8.3, 0.9 Hz, 1H), 5.26 (ABq, J=11.1 Hz, 2H), 4.46 (dd, J=9.0, 5.1 Hz, 1H), 3.21-3.08 (m+s, 4H), 3.05-2.90 (m, 1H), 2.53 (s, 3H); ¹⁹F NMR (376 MHz, CDCl₃) δ=−64.22 (t, J=10.8 Hz, 3F).

Synthesis 23—6-Methyl-2-phenyl-3-(3,3,3-trifluoro-1-phenylpropyl)-1H-indole (23, ABD1145)

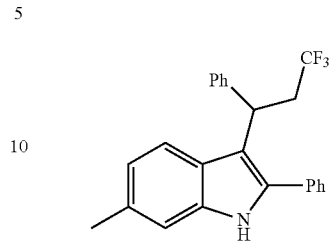

Using a method analogous to Method J, with compound 22 (25 mg, 0.059 mmol). Purification by flash column chromatography (silica gel, hexanes:EtOAc 5:1) gave compound 23 (13.6 mg, 61%) as a white solid.

¹H NMR (400 MHz, CDCl₃) δ=7.97 (brs, 1H), 7.51-7.45 (m, 5H), 7.44-7.41 (m, 1H), 7.40-7.36 (m, 2H), 7.33-7.27 (m, 2H), 7.24-7.20 (m, 2H), 6.97 (dd, J=8.2, 1.0 Hz, 1H), 4.76 (dd, J=8.6, 5.3 Hz, 1H), 3.28-3.13 (m, 1H), 3.13-2.97 (m, 1H), 2.49 (s, 3H); ¹⁹F NMR (376 MHz, CDCl₃) δ=−64.38 (t, J=10.7 Hz). m/z (ESI) 380.2 [M+H]⁺

Synthesis 24—1,1,1-Trifluoro-3-(1-(methoxymethyl)-2-phenyl-1H-indol-3-yl)-3-phenylpropan-2-one (24)

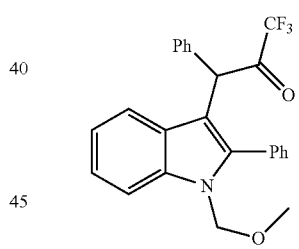

Method K: To a solution of compound 14 (24 mg, 0.056 mmol) in CH₂Cl₂ (2 mL) was added Dess-Martin periodinane (30 mg, 0.071 mmol) at 0° C. The reaction mixture was allowed to warm to 23° C. and stirred for 16 h before it was quenched with a saturated solution of Na₂SO₃ (2 mL). The resulting mixture was extracted with CH₂Cl₂ (3×5 mL), the combined organic layers were dried over Na₂SO₄ and concentrated in vacuo. The residue was purified by flash column chromatography (silica gel, hexanes:EtOAc 9:1) to give compound 24 (22 mg, 93%) as a white solid.

¹H NMR (400 MHz, CDCl₃) δ=7.60 (d, J=8.5 Hz, 1H), 7.55-7.47 (m, 4H), 7.37-7.30 (m, 6H), 7.23-7.16 (m, 3H), 5.59 (s, 1H), 5.37 (ABq, J=10.8 Hz, 2H), 3.21 (s, 3H); ¹⁹F NMR (376 MHz, CDCl₃) δ=−76.39 (s, 3F). m/z (ESI) 446.1 [M+Na]⁺

Synthesis 25—1,1,1-Trifluoro-3-phenyl-3-(2-phenyl-1H-indol-3-yl)propan-2-one (25, ABD1139)

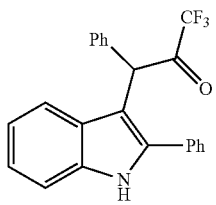 [SMILES: O=C(C(c1ccccc1)c1c(-c2ccccc2)[nH]c2ccccc12)C(F)(F)F]

Method L: To a solution of compound 24 (18 mg, 0.426 mmol) in THF (2 mL) was added 6 M HCl. (0.2 mL). The mixture was stirred at 60° C. for 16 h prior to quenching with a saturated solution of NaHCO$_3$ (5 mL) and diluted with CH$_2$Cl$_2$ (10 mL). The layers were separated, and the aqueous layer was extracted with CH$_2$Cl$_2$ (4×5 mL). The combined organic layers were dried over Na$_2$SO$_4$ and concentrated in vacuo. The residue was purified by flash column chromatography (silica gel, hexanes:EtOAc 6:1) to give compound 25 (14 mg, 87%) as a white solid.

$^1$H NMR (400 MHz, CDCl$_3$) δ=8.39 (brs, 1H), 7.51-7.42 (m, 5H), 7.39-7.33 (m, 3H), 7.31-7.24 (m, 5H), 7.14 (ddd, J=8.5, 7.4, 1.0 Hz, 1H), 5.88 (s, 1H); $^{19}$F NMR (376 MHz, CDCl$_3$) δ=−76.46 (s, 3F). m/z (ESI) 380.1 [M+H]$^+$ Synthesis 26—1,1,1-Trifluoro-3-(1-(methoxymethyl)-6-methyl-2-phenyl-1H-indol-3-yl)-3-phenyl-propan-2-one (26)

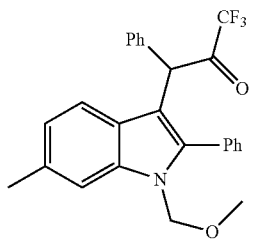

Using a method analogous to Method K, with compound 20 (36 mg, 0.082 mmol) and Dess-Martin periodinane (44 mg, 0.104 mmol). Purification by flash column chromatography (silica gel, hexanes:EtOAc 9:1) gave compound 26 (32 mg, 90%) as a white solid.

$^1$H NMR (400 MHz, CDCl$_3$) δ=7.58-7.46 (m, 3H), 7.44-7.36 (m, 4H), 7.35-7.29 (m, 3H), 7.23-7.18 (m, 2H), 7.04 (d, J=8.2 Hz, 1H), 5.57 (s, 1H), 5.35 (ABq, J=10.7 Hz, 2H), 3.21 (s, 3H), 2.54 (s, 3H); $^{19}$F NMR (376 MHz, CDCl$_3$) δ=−76.39 (s, 3F). m/z (ESI) 438.2 [M+H]$^+$

Synthesis 27—1,1,1-Trifluoro-3-(6-methyl-2-phenyl-1H-indol-3-yl)-3-phenylpropan-2-one (27, ABD1146)

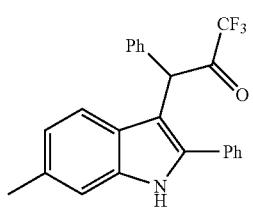 [SMILES: Cc1ccc2c(C(C(=O)C(F)(F)F)c3ccccc3)c(-c3ccccc3)[nH]c2c1]

Using a method analogous to Method L, with compound 26 (25 mg, 0.057 mmol). Purification by flash column chromatography (silica gel, hexanes:EtOAc 6:1) gave compound 27 (20 mg, 89%) as a white solid.

$^1$H NMR (400 MHz, CDCl$_3$) δ=8.26 (brs, 1H), 7.53-7.41 (m, 5H), 7.40-7.31 (m, 4H), 7.30-7.21 (m, 3H), 6.98 (dd, J=8.2, 1.1 Hz, 1H), 5.86 (s, 1H), 2.50 (s, 3H); $^{19}$F NMR (376 MHz, CDCl$_3$) δ=−76.46 (s, 3F). m/z (ESI) 394.1 [M+H]$^+$.

Synthesis 28—Ethyl 2-(1-(methoxymethyl)-6-methyl-2-phenyl-1H-indol-3-yl-2-oxoacetate (28)

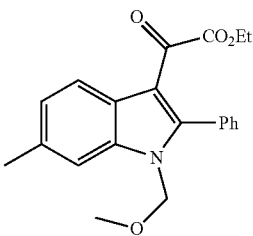 [SMILES: CCOC(=O)C(=O)c1c(-c2ccccc2)n(COC)c2cc(C)ccc12]

To a solution of compound 7 (450 mg, 1.36 mmol) in THF (10 mL) was added a solution of nBuLi (680 µL, 1.63 mmol, 2.4 M in hexanes) at −78° C. The resulting mixture was stirred for 30 min at −78° C. prior to adding MgBr$_2$.OEt$_2$ (530 mg, 2.05 mmol) and then allowed to warm to −40° C. over 1 h. After which time, the reaction mixture was cooled to −78° C. and diethyl oxalate (301 mg, 280 µL, 2.06 mmol) was added. The mixture was stirred for 1 h at −78° C. and allowed to warm to 23° C. for 15 h prior to quenching with a saturated solution of NH$_4$Cl (10 mL). The layers were separated, and the aqueous layer was extracted with CH$_2$Cl$_2$ (4×5 mL). The combined organic layers were dried over Na$_2$SO$_4$ and concentrated in vacuo. The residue was purified by flash column chromatography (silica gel, hexanes:EtOAc 5:1) to give compound 28 (383 mg, 80%) as a pale yellow oil.

$^1$H NMR (400 MHz, CDCl$_3$) δ=8.35 (t, J=8.2 Hz, 1H), 7.61-7.46 (m, 5H), 7.38 (s, 1H) 7.24 (d, J=8.0 Hz, 1H), 5.28 (s, 2H), 3.57 (q, J=7.2 Hz, 2H), 3.22 (s, 3H), 2.53 (s, 3H), 1.09 (t, J=7.2 Hz, 3H); $^{13}$C NMR (101 MHz, CDCl$_3$) δ=183.6, 164.8, 148.9, 137.1, 134.8, 131.4, 130.1, 129.0, 128.2, 125.6, 124.4, 122.1, 112.3, 110.7, 74.8, 61.3, 56.3, 21.9, 13.6. m/z (ESI) 352.2 [M+H$^+$].

Synthesis 29—Ethyl 2-(1-(methoxymethyl)-6-methyl-2-phenyl-1H-indol-3-yl)acrylate (29)

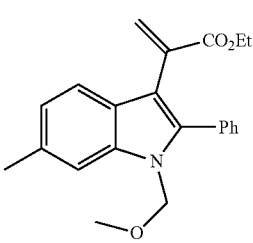 [SMILES: C=C(C(=O)OCC)c1c(-c2ccccc2)n(COC)c2cc(C)ccc12]

To a solution of compound 28 (370 mg, 1.05 mmol) in THF (10 mL) was added a solution of MeMgBr (360 µL, 1.08 mmol, 3.0 M in Et$_2$O) at −40° C. The resulting mixture was stirred for 1 h at 0° C. before it was quenched with a saturated solution of NH₄Cl (5 mL) and diluted with EtOAc (20 mL). The layers were separated, and the organic layer was extracted with H₂O (2×10 mL). The combined organic layers were dried over Na₂SO₄ and concentrated in vacuo to give the corresponding tertiary alcohol which was used without further purification.

To a solution of the crude product in CH₂Cl₂ (5 mL) was added Et₃N (266 mg, 367 μL, 2.63 mmol) and methanesulfonyl chloride (181 mg, 122 μL, 1.58 mmol) at 0° C. The resulting mixture was stirred for 3 h at 0° C. before it was quenched with a saturated solution of NH₄Cl (5 mL) and diluted with EtOAc (30 mL). The layers were separated, and the organic layer was extracted with H₂O (2×10 mL). The combined organic layers were dried over Na₂SO₄ and concentrated in vacuo. The residue was purified by flash column chromatography (silica gel, hexanes:EtOAc 8:1) to give compound 29 (310 mg, 84% for 2 steps) as a colourless oil.

¹H NMR (400 MHz, CDCl₃) δ=7.52 (d, J=8.2 Hz, 1H), 7.49-7.38 (m, 5H), 7.36 (s. 1H), 7.08 (dd, J=8.2, 1.0 Hz, 1H), 6.44 (d, J=1.8 Hz, 1H), 5.86 (d, J=1.8 Hz, 1H), 5.38 (s, 2H), 3.87 (q, J=7.1 Hz, 2H), 3.27 (s, 3H), 2.55 (s, 3H), 1.03 (t, J=7.1 Hz, 3H); ¹³C NMR (101 MHz, CDCl₃) δ=167.5, 138.4, 137. 5, 135.0, 132.7, 131.7, 130.6, 128.4, 128.2, 127.6, 125.6, 122.8, 119.2, 112.0, 110.3, 74.8, 60.7, 55.9, 21.9, 13.9. m/z (ESI) 350.2 [M+H⁺].

Synthesis 30—Ethyl 3-cyclopropyl-2-(1-(methoxymethyl)-6-methyl-2-phenyl-1H-indol-3-yl)propanoate (30)

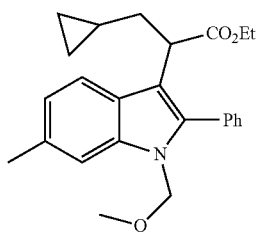 [SMILES: CCOC(=O)C(CC1CC1)c1c(-c2ccccc2)n(COC)c2cc(C)ccc12]

To a solution of cyclopropylmagnesium bromide (2.3 mL, 2.3 mmol, 1.0 M in 2-MeTHF) in THF (5 mL) was added CuI (220 mg, 1.15 mmol) at −78° C. The resulting mixture was stirred for 1 h at −30° C. After which time, the reaction mixture was cooled to −78° C. and a solution of compound 29 (210 mg, 0.6 mmol) in THF (2 mL) was added. The mixture was stirred for 30 min at −78° C. and allowed to warm to 0° C. for 3 h prior to quenching with a saturated solution of NH₄Cl (10 mL). The layers were separated, and the aqueous layer was extracted with CH₂Cl₂ (4×5 mL). The combined organic layers were dried over Na₂SO₄ and concentrated in vacuo. The residue was purified by flash column chromatography (silica gel, hexanes:EtOAc 10:1) to give compound 30 (225 mg, 96%).

¹H NMR (400 MHz, CDCl₃) δ=7.74 (d, J=8.1 Hz, 1H), 7.59-7.41 (m, 5H), 7.32 (s, 1H), 7.03 (dd, J=8.1, 1.0 Hz, 1H), 5.27 (s, 2H), 4.20-4.01 (m, 2H), 3.78 (dd, J=8.5, 6.9 Hz, 1H), 3.18 (s, 3H), 2.52 (s, 3H), 2.00 (ddd, J=14.7, 8.5, 6.4 Hz, 1H), 1.95-1.85 (m, 1H), 1.21 (t, J=7.1 Hz, 3H), 0.57-0.44 (m, 1H), 0.30-0.15 (m, 2H), −0.04-−0.17 (m, 2H); ¹³C NMR (101 MHz, CDCl₃) δ=174.4, 138.5, 137.5, 132.2, 131.30, 131.27, 128.5, 128.3, 124.6, 122.1, 120. 5, 112.1, 110.2, 74.7, 60.5, 55.6, 43.5, 36.4, 21.9, 14.2, 9.4, 4.4, 4.3. m/z (ESI) 392.2 [M+H⁺].

Synthesis 31—3-Cyclopropyl-2-(1-(methoxymethyl)-6-methyl-2-phenyl-1H-indol-3-yl)propanal (31)

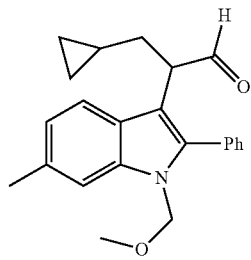 [SMILES: COCn1c(-c2ccccc2)c(C(C=O)CC2CC2)c2ccc(C)cc21]

To a solution of compound 30 (220 mg, 0.56 mmol) in THF was added lithium triethylborohydride (1.24 mL, 1.24 mmol, 1.0 M in THF) at 0° C. The resulting mixture was stirred for 1 h at 0° C. before it was quenched with a saturated solution of NH₄Cl (5 mL) and diluted with EtOAc (20 mL). The layers were separated, and the organic layer was extracted with H₂O (2×10 mL). The combined organic layers were dried over Na₂SO₄ and concentrated in vacuo to give the corresponding primary alcohol which was used without further purification.

To a solution of the crude alcohol in CH₂Cl₂ (10 mL) was added Dess-Martin periodinane (300 mg, 0.71 mmol) at 0° C. The reaction mixture was stirred for 6 h before it was quenched with a saturated solution of Na₂SO₃ (5 mL). The resulting mixture was extracted with CH₂Cl₂ (3×10 mL), combined organic layers were dried over Na₂SO₄ and concentrated in vacuo. The residue was purified by flash column chromatography (silica gel, hexanes:EtOAc 10:1→5:1) to give compound 31 (172 mg, 88% for 2 steps).

¹H NMR (400 MHz, CDCl₃) δ=9.80 (d, J=0.9 Hz, 1H), 7.58-7.42 (m, 6H), 7.35 (d, J=11.1 Hz, 1H), 7.04 (dd, J=8.1, 0.9 Hz, 1H), 5.31 (ABq, J=12.2 Hz, 2H), 3.82-3.71 (m, 1H), 3.21 (s, 3H), 2.54 (s, 3H), 2.01-1.83 (m, 2H), 0.68-0.54 (m, 1H), 0.37-0.24 (m, 2H), 0.01-−0.09 (m, 2H); ¹³C NMR (101 MHz, CDCl₃) δ=201.3, 139.7, 137.5, 132.8, 131.2, 131.0, 128.8, 128.5, 125.0, 122.5, 119.3, 110.5, 109.1, 74.7, 55.8, 51.3, 33.6, 21.9, 9.4, 4.8, 4.6. m/z (ESI) 348.2 [M+H⁺].

Synthesis 32—4-Cyclopropyl-1,1,1-trifluoro-3-(1-(rnethoxyrnethyl)-6-methyl-2-phenyl-1H-indol-3-yl)butan-2-ol (32)

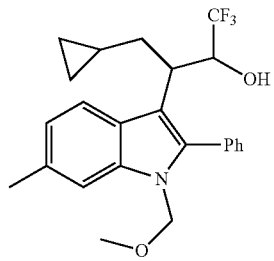 [SMILES: COCn1c(-c2ccccc2)c(C(CC2CC2)C(O)C(F)(F)F)c2ccc(C)cc21]

Using a method analogous to Method G, with compound 31 (110 mg, 0.32 mmol), CsF (10 mg, 0.066 mmol) and trimethyl(trifluoromethyl)silane (67 mg, 71 μL, 0.47 mmol). The residue was passed through a short plug of silica gel (EtOAc) and concentrated in vacuo to give compound 32

(115 mg, 87%; ca. 9:1 mixture of inseparable diastereoisomers determined by $^1$H NMR) as a pale yellow oil. The spectroscopic data of the major diastereomer is reported.

$^1$H NMR (400 MHz, CDCl$_3$) δ=7.70 (d, J=8.2 Hz, 1H), 7.57-7.40 (m, 5H), 7.37 (s, 1H), 7.05 (d, J=8.2 Hz, 1H), 5.27 (s, 2H), 4.49-4.25 (m, 1H), 3.24-3.18 (m, 1H), 3.12 (s, 3H), 2.55 (s, 3H), 2.41-2.26 (m, 1H), 1.60-1.47 (m, 1H), 0.59-0.44 (m, 1H), 0.34-0.21 (m, 2H), 0.07--0.14 (m, 2H); $^{19}$F NMR (376 MHz, CDCl$_3$) δ=−76.21 (d, J=7.1 Hz, 3F).

Synthesis 33—O-(4-Cyclopropyl-1,1,1-trifluoro-3-(1-(methoxymethyl)-6-methyl-2-phenyl-1H-indol-3-yl)butan-2-yl) O-phenyl carbonothioate (33)

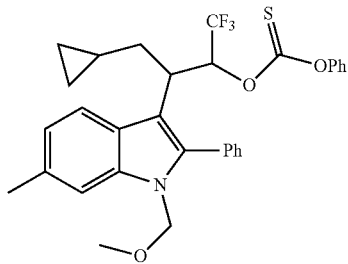 [SMILES: COCn1c(-c2ccccc2)c(C(CC2CC2)C(OC(=S)Oc2ccccc2)C(F)(F)F)c2ccc(C)cc21]

Using a method analogous to Method H, with compound 32 (110 mg, 0.26 mmol), nBuLi (130 μL, 0.31 mmol, 2.4 M in hexanes) and O-phenyl chlorothionoformate (55 μL, 68 mg, 0.40 mmol). Purification by flash column chromatography (silica gel, hexanes:EtOAc 10:1→5:1) gave compound 33 (132 mg, 92%; mixture of inseparable diastereoisomers) as a yellow oil.

$^1$H NMR (400 MHz, CDCl$_3$) δ=7.84 (d, J=8.0 Hz, 1H), 7.59-7.47 (m, 5H), 7.47-7.30 (m, 4H), 7.10 (dd, J=8.0, 0.9 Hz, 1H), 7.00 (d, J=7.7 Hz, 2H), 6.59-6.38 (m, 1H), 5.30 (s, 2H), 3.62-3.46 (m, 1H), 3.12 (s, 3H), 2.61-2.47 (s+m, 4H), 1.51-1.33 (m, 1H), 0.63-0.48 (m, 1H), 0.39-0.24 (m, 2H), 0.07--0.09 (m, 2H); $^{19}$F NMR (376 MHz, CDCl$_3$) δ=−72.80 (d, J=6.2 Hz, 3F).

Synthesis 34—3-(1-Cyclopropyl-4,4,4-trifluorobutan-2-yl)-1-(methoxymethyl)-6-methyl-2-phenyl-1H-indole (34)

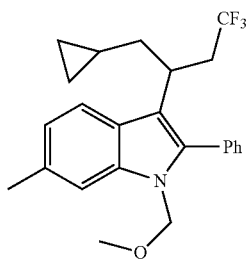 [SMILES: COCn1c(-c2ccccc2)c(C(CC2CC2)CC(F)(F)F)c2ccc(C)cc21]

Using a method analogous to Method I, with compound 33 (100 mg, 0.18 mmol), tri-n-butyltin hydride (79 mg, 73 μL, 0.27 mmol) and BEt$_3$ (18 μL, 0.018 mmol, 1.0 M in hexanes). Purification by flash column chromatography (silica gel, hexanes:EtOAc 10:1) gave compound 34 (58 mg, 79%) as a colourless oil.

$^1$H NMR (400 MHz, CDCl$_3$) δ=7.57 (d, J=8.1 Hz, 1H), 7.54-7.40 (m, 5H), 7.37 (s, 1H), 7.06 (d, J=8.1 Hz, 1H), 5.27 (ABq, J=11.8 Hz, 2H), 3.30-3.17 (m, 1H), 3.14 (s, 3H), 2.84-2.64 (m, 1H), 2.64-2.44 (s+m, 4H), 2.13 (ddd, J=13.7, 8.1, 5.5 Hz, 1H), 1.41 (ddd, J=13.7, 8.1, 5.5 Hz, 1H), 0.61-0.43 (m, 1H), 0.37-0.21 (m, 2H), 0.03--0.13 (m, 2H); $^{13}$C NMR (101 MHz, CDCl$_3$) δ=137.8, 137.7, 132.1, 131.5, 131.3, 128.5, 128.2, 127.0 (q, J=277.8 Hz), 124.2, 121.8, 119.4, 115.4, 110.7, 74.5, 55.5, 40.5, 38.8 (q, J=26.8 Hz), 31.6 (q, J=2.4 Hz), 21.9, 9.5, 4.7, 4.5; $^{19}$F NMR (376 MHz, CDCl$_3$) δ=−64.05 (t, J=11.1 Hz, 3F). m/z (ESI) 402.2 [M+H$^+$].

Synthesis 35—3-(1-Cyclopropyl-4,4,4-trifluorobutan-2-yl)-6-methyl-2-phenyl-1H-indole (35, ABD1156)

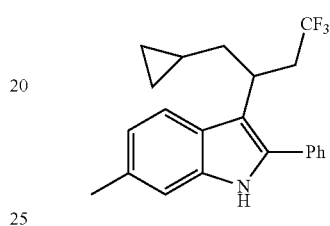

Using a method analogous to Method J, with compound 34 (40 mg, 0.1 mmol) Purification by flash column chromatography (silica gel, hexanes:EtOAc 5:1) gave compound 35 (29 mg, 82%) as a white solid.

$^1$H NMR (400 MHz, CDCl$_3$) δ=7.87 (br s, 1H), 7.64-7.56 (m, 3H), 7.56-7.48 (m, 2H), 7.48-7.41 (m, 1H), 7.23 (s, 1H), 7.02 (dd, J=8.1, 1.0 Hz, 1H), 3.80-3.38 (m, 1H), 2.88-2.74 (m, 1H), 2.73-2.58 (m, 1H), 2.53 (s, 3H), 2.24 (ddd, J=13.8, 8.5, 5.6, 1H), 1.49 (ddd, J=13.8, 8.5, 5.6 Hz 1H), 0.66-0.45 (m, 1H), 0.40-0.25 (m, 2H), 0.09--0.08 (m, 2H); $^{13}$C NMR (101 MHz, CDCl$_3$) δ=136.8, 135.0, 133.4, 131.9, 128.8, 128.7, 127.9, 127.1 (q, J=277.3 Hz), 124.7, 121.3, 119.6, 114.1, 111.3, 40.5, 38.9 (q, J=26.6 Hz), 31.4 (q, J=2.3 Hz), 21.7, 9.6, 4.7, 4.5; $^{19}$F NMR (376 MHz, CDCl$_3$) δ=−64.07 (t, J=11.1 Hz, 3F). m/z (ESI) 358.2 [M+H$^+$].

Synthesis 36—3-Ethynyl-1-(methoxymethyl)-6-methyl-2-phenyl-1H-indole (36)

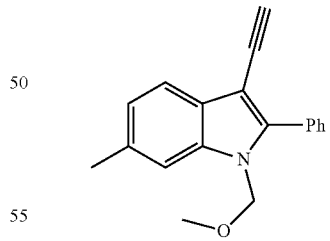

Method M: To a solution of 1-(methoxymethyl)-6-methyl-2-phenyl-1H-indole (575 mg, 2.29 mmol) in CH$_2$Cl$_2$ (10 mL) was added N-iodosuccinimide (525 mg, 2.33 mmol) at 0° C. The reaction mixture was stirred for 3 h before it was quenched with a saturated solution of Na$_2$SO$_3$ (5 mL) and diluted with H$_2$O (10 mL). The layers were separated, and the aqueous layer was extracted with CH$_2$Cl$_2$ (3×10 mL). The combined organic layers were dried over Na$_2$SO$_4$ and concentrated in vacuo to give the corresponding 3-iodo-indole which was used without further purification.

To a solution of the crude 3-iodo-indole in DMF (5 mL) was added trimethylsilylacetylene (337 mg, 475 μL, 3.43 mmol), PdCl$_2$(PPh$_3$)$_2$ (80 mg, 0.114 mmol), CuI (26 mg, 0.137 mmol) and Et$_3$N (695 mg, 957 μL, 6.87 mmol) at 23° C. The reaction mixture was stirred for 6 h at 23° C. before it was quenched with a saturated solution of NH$_4$Cl (10 mL) and diluted with EtOAc (50 mL). The layers were separated, and the organic layer was extracted with H$_2$O (3×10 mL). The combined organic layers were dried over Na$_2$SO$_4$ and concentrated in vacuo. The residue was passed through a short plug of silica gel (CH$_2$Cl$_2$) and concentrated in vacuo prior to use.

To a solution of the crude product was added a solution of tetra-n-butylammonium fluoride (2.8 mL, 2.8 mmol, 1.0 in THF) at 0° C. The reaction mixture was stirred for 2 h at 23° C. before it was it was quenched with a saturated solution of NH$_4$Cl (10 mL) and diluted with EtOAc (50 mL). The layers were separated, and the organic layer was extracted with H$_2$O (3×10 mL). The combined organic layers were dried over Na$_2$SO$_4$ and concentrated in vacuo. The residue was purified by flash column chromatography (silica gel, hexanes:EtOAc 5:1) to give compound 36 (566 mg, 90% for 3 steps).

$^1$H NMR (400 MHz, CDCl$_3$) δ=7.76-7.66 (m, 1H), 7.59-7.44 (m, 5H), 7.40-7.33 (m, 1H), 7.15 (d, J=8.0 Hz, 1H), 5.39 (s, 2H), 3.28 (s, 3H), 3.18 (s, 1H), 2.56 (s, 3H); $^{13}$C NMR (101 MHz, CDCl$_3$) δ=144.4, 137.1, 133.6, 131.2, 130.5, 130.3, 128.8, 128.5, 127.2, 123.4, 119.7, 110.5, 79.7, 78.00, 74.9, 56.0, 22.0. m/z (ESI) 276.1 [M+H$^+$].

Synthesis 37—1-(Methoxymethyl)-6-methyl-2-phenyl-3-(3,3,3-trifluoroprop-1-yn-1-yl)-1H-indole (37)

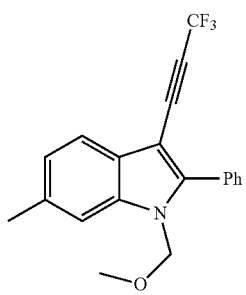 [SMILES: COCn1c(-c2ccccc2)c(C#CC(F)(F)F)c2ccc(C)cc21]

Method N: To a solution of N,N,N',N'-tetramethylethylenediamine (324 mg, 418 μL, 2.79 mmol) in DMF (5 mL) was added CuI (531 mg, 2.79 mmol) and K$_2$CO$_3$ (771 mg, 5.58 mmol) at 23° C. The resulting blue mixture was stirred vigorously at 23° C. under air (1 atm) for 20 min before trimethyl(trifluoromethyl)silane (529 mg, 550 μL, 3.72 mmol) was added and the resulting mixture was stirred for further 15 min under air. After which time, the deep green mixture was cooled to 0° C. prior to adding a mixture of compound 36 (512 mg, 1.86 mmol) and trimethyl(trifluoromethyl)silane (529 mg, 550 μL, 3.72 mmol) in DMF (2 mL). The reaction mixture was stirred at 0° C. for 30 min and allowed to warm to 23° C. for 6 h before it was quenched with a saturated solution of NH$_4$Cl (10 mL) and diluted with EtOAc (50 mL). The layers were separated, and the organic layer was extracted with H$_2$O (3×10 mL). The combined organic layers were dried over Na$_2$SO$_4$ and concentrated in vacuo. The residue was purified by flash column chromatography (silica gel, hexanes:EtOAc 4:1) to give compound 37 (556 mg, 87%) as a pale yellow oil.

$^1$H NMR (400 MHz, CDCl$_3$) δ=7.75-7.64 (m, 3H), 7.64-7.47 (m, 3H), 7.39 (s, 1H), 7.19 (d, J=8.0 Hz, 1H), 5.40 (s, 2H), 3.32 (s, 3H), 2.58 (s, 3H); $^{13}$C NMR (101 MHz, CDCl$_3$) δ=147.0 (q, J=1.7 Hz), 137.1, 134.3, 130.1, 129.50, 129.47, 128.8, 126.5, 124.1, 119.4, 115.5 (q, J=256.2 Hz), 110.9, 93.6 (q, J=2.5 Hz), 83.3 (q, J=6.2 Hz), 78.7 (q, J=52.2 Hz), 75.0, 56.1, 22.0; $^{19}$F NMR (376 MHz, CDCl$_3$) δ=−48.59 (s, 3F). m/z (ESI) 344.1 [M+H$^+$].

Synthesis 38—(E)-1-(Methoxymethyl)-6-methyl-2-phenyl-3-(3,3,3-trifluoro-1-iodoprop-1-en-1-yl)-1H-indole (38)

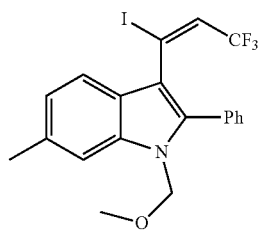 [SMILES: COCn1c(-c2ccccc2)c(/C(I)=C\C(F)(F)F)c2ccc(C)cc21]

Method O: To a solution of compound 37 (420 mg, 1.22 mmol) in CH$_2$Cl$_2$ (4 mL) was added LiI (180 mg, 1.35 mmol) and HOAc (1 mL) at 0° C. The resulting mixture was stirred at 23° C. for 16 h before it was quenched with a saturated solution of NaHCO$_3$ (10 mL) and diluted with CH$_2$Cl$_2$ (10 mL). The layers were separated, and the aqueous layer was extracted with CH$_2$Cl$_2$ (2×10 mL). The combined organic layers were dried over Na$_2$SO$_4$ and concentrated in vacuo. The residue was purified by flash column chromatography (silica gel, hexanes:EtOAc 10:1) to give compound 38 (558 mg, 97%) as a pale yellow solid.

$^1$H NMR (400 MHz, CDCl$_3$) δ=7.65-7.48 (m, 6H), 7.38 (s, 1H), 7.24-7.14 (m, 1H), 6.71 (q, J=7.1 Hz, 1H), 5.38 (s, 2H), 3.25 (s, 3H), 2.58 (s, 3H); $^{13}$C NMR (101 MHz, CDCl$_3$) δ=137.5, 137.0, 133.6, 132.0 (q, J=33.9 Hz), 130.4, 130.2, 129.0, 128.6, 124.0, 123.3, 121.3 (q, J=274.4 Hz), 119.4, 115.8, 110.6, 104.4 (q, J=6.2 Hz), 74.8, 55.9, 22.0; $^{19}$F NMR (376 MHz, CDCl$_3$) δ=−60.80 (d, J=7.1 Hz, 3F). m/z (ESI) 472.0 [M+H$^+$].

Synthesis 39—(E)-1-(Methoxymethyl)-6-methyl-2-phenyl-3-(3,3,3-trifluoro-1-(thiophen-2-yl)prop-1-en-1-yl)-1H-indole (39)

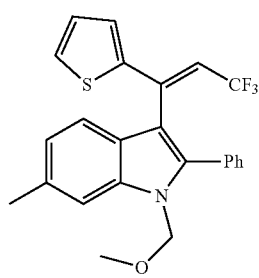 [SMILES: COCn1c(-c2ccccc2)c(/C(=C\C(F)(F)F)c2cccs2)c2ccc(C)cc21]

Method P: To a solution of compound 38 (146 mg, 0.31 mmol) in DMF (5 mL) was added tri-n-butyl(thiophen-2-yl)stannane (175 mg, 0.47 mmol), P(o-Tol)$_3$ (14 mg, 0.046 mmol), PdCl$_2$(MeCN)$_2$ (7.8 mg, 0.03 mmol) and CuI (9 mg, 0.046 mmol) at 23° C. The resulting mixture was stirred at 23° C. for 20 min before it was heated to 55° C. for 3 h. After which time, the reaction mixture was quenched with a saturated solution of NH₄Cl (10 mL) and diluted with Et₂O (50 mL). The layers were separated, and the organic layer was extracted with H₂O (3×10 mL). The combined organic layers were dried over Na₂SO₄ and concentrated in vacuo. The residue was purified by flash column chromatography (silica gel, hexanes:EtOAc 10:1) to give compound 39 (120 mg, 90%) as a colourless oil.

¹H NMR (400 MHz, CDCl₃) δ=7.50-7.31 (m, 7H), 7.27 (d, J=5.0 Hz, 1H), 7.06 (d, J=8.1 Hz, 1H), 6.98 (d, J=3.4 Hz, 1H), 6.91 (dd, J=4.9, 3.8 Hz, 1H), 6.31 (q, J=8.0 Hz, 1H), 5.46 (s, 2H), 3.24 (s, 3H), 2.57 (s, 3H); ¹³C NMR (101 MHz, CDCl₃) δ=144.3, 138.4 (q, J=5.5 Hz), 137.3, 132.9, 130.8, 130.3, 128.4, 128.3, 128.1, 127.7, 127.4, 126.2, 123.1 (q, J=270.6 Hz), 123.0, 115.1 (q, J=33.4 Hz), 119.4, 111.1, 110.5, 74.8, 55.6, 22.0; ¹⁹F NMR (376 MHz, CDCl₃) δ=−58.23 (d, J=8.0 Hz, 3F). m/z (ESI) 428.1 [M+H⁺].

Synthesis 40—6-Methyl-2-phenyl-3-(3,3,3-trifluoro-1-(thiophen-2-yl)propyl)-1H-indole (40, ABD1187)

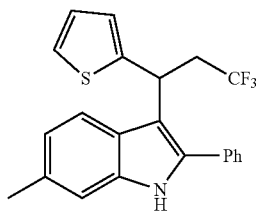 [SMILES: Cc1ccc2c(C(CC(F)(F)F)c3cccs3)c(-c3ccccc3)[nH]c2c1]

Method Q: To a solution of compound 39 (108 mg, 0.25 mmol) in THF (5 mL) was added 6 M HCl (0.5 mL). The mixture was stirred at 60° C. for 16 h prior to quenching with a saturated solution of NaHCO₃ (10 mL) and diluting with CH₂Cl₂ (10 mL). The layers were separated, and the aqueous layer was extracted with CH₂Cl₂ (4×5 mL). The combined organic layers were dried over Na₂SO₄ and concentrated in vacuo. The residue was passed through a short plug of silica gel (CH₂Cl₂) and concentrated in vacuo prior to use.

To a solution of the crude product in CH₂Cl₂ (5 mL) was added Et₃SiH (176 mg, 242 μL, 1.51 mmol) and trifluoroacetic acid (144 mg, 97 μL, 1.26 mmol) at 0° C. The resulting red solution was stirred at 23° C. for 16 h before it was quenched with a saturated solution of NaHCO₃ (10 mL) and diluting with CH₂Cl₂ (10 mL). The layers were separated, and the aqueous layer was extracted with CH₂Cl₂ (4×5 mL). The combined organic layers were dried over Na₂SO₄ and concentrated in vacuo. The residue was purified by flash column chromatography (silica gel, hexanes:EtOAc 10:1) to give compound 40 (64 mg, 66% for 2 steps) as a white solid.

¹H NMR (400 MHz, CDCl₃) δ=7.95 (br s, 1H), 7.62-7.36 (m, 6H), 7.23 (s, 1H), 7.20 (dd, J=4.2, 2.4 Hz, 1H), 7.04-6.91 (m, 3H), 4.97 (dd, J=9.2, 4.8 Hz, 1H), 3.30-3.16 (m, 1H), 3.16-3.00 (m, 1H), 2.53 (s, 3H); ¹³C NMR (101 MHz, CDCl₃) δ=148.0, 136.7, 135.4, 132.6, 132.3, 128.9 128.7, 128.3, 126.8, 126.3 (q, J=278.1 Hz), 124.5, 124.2, 124.1, 121.7, 119.9, 112.8, 111.3, 39.6 (q, J=27.1 Hz), 32.1 (q, J=3.2 Hz), 21.7; ¹⁹F NMR (376 MHz, CDCl₃) δ=−64.42 (t, J=10.7 Hz, 3F). m/z (ESI) 386.1 [M+H⁺].

Synthesis 41—(E)-1-(Methoxymethyl)-6-methyl-2-phenyl-3-(3,3,3-trifluoro-1-(furan-2-yl)prop-1-en-1-yl)-1H-indole (41)

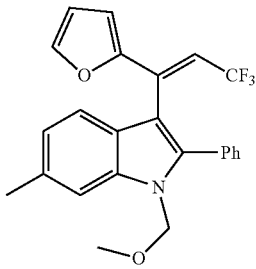

Using a method analogous to Method P, with compound 38 (60 mg, 0.127 mmol), tri-n-butyl(furan-2-yl)stannane (68 mg, 0.191 mmol), P(o-Tol)₃ (5.8 mg, 0.019 mmol), PdCl₂(MeCN)₂ (3.3 mg, 0.013 mmol) and CuI (3.6 mg, 0.019 mmol). Purification by flash column chromatography (silica gel, hexanes:EtOAc 10:1) gave compound 41 (48 mg, 92%) as a colourless oil.

¹H NMR (400 MHz, CDCl₃) δ=7.50-7.32 (m, 8H), 7.06 (dd, J=8.2, 0.6 Hz, 1H), 6.46 (q, J=8.4 Hz, 1H), 6.29 (dd, J=3.4, 1.8 Hz, 1H), 6.07 (d, J=3.4, 1H Hz), 5.43 (s, 2H), 3.23 (s, 3H), 2.56 (s, 3H); ¹³C NMR (101 MHz, CDCl₃) δ=152.7, 143.7, 138.4, 137.3, 133.1 (q, J=5.6 Hz), 132.9, 130.9, 130.2, 128.4, 128.3, 126.3, 123.5 (q, J=269.5 Hz), 122.9, 119.3, 114.2 (q, J=33.8 Hz), 113.5, 111.9, 110.4, 108.8, 74.8, 55.6, 22.0; ¹⁹F NMR (376 MHz, CDCl₃) δ=−58.01 (d, J=8.4 Hz, 3F). m/z (ESI) 412.2 [M+H⁺].

Synthesis 42—6-Methyl-2-phenyl-3-(3,3,3-trifluoro-1-(furan-2-yl)propyl)-1H-indole (42, ABD1188)

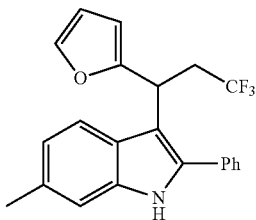 [SMILES: Cc1ccc2c(C(CC(F)(F)F)c3ccco3)c(-c3ccccc3)[nH]c2c1]

Using a method analogous to Method Q, with compound 41 (42 mg, 0.10 mmol), Et₃SiH (71 mg, 98 μL, 0.61 mmol) and trifluoroacetic acid (60 mg, 40 μL, 0.53 mmol). Purification by flash column chromatography (silica gel, hexanes:EtOAc 10:1) gave compound 42 (29 mg, 77% for 2 steps) as a white solid.

¹H NMR (400 MHz, CDCl₃) δ=8.00 (br s, 1H), 7.62-7.33 (m, 7H), 7.22 (s, 1H), 6.98 (d, J=8.1 Hz, 1H), 6.32 (dd, J=3.2, 1.6 Hz, 1H), 6.13 (d, J=3.2 Hz, 1H), 4.79 (dd, J=8.4, 5.8 Hz, 1H), 3.27-3.06 (m, 1H), 3.06-2.87 (m, 1H), 2.50 (s, 3H); ¹³C NMR (101 MHz, CDCl₃) δ=155.5, 141.6, 136.6, 135.4, 132.6, 132.2, 128.9, 128.7, 128.2, 126.2 (q, J=277.2 Hz), 124.7, 121.6, 119.8, 111.2, 110.8, 110.3, 106.2, 37.0 (q, J=27.4 Hz), 30.7 (q, J=2.8 Hz), 21.7; ¹⁹F NMR (376 MHz, CDCl₃) δ=−64.73 (t, J=10.5 Hz, 3F). m/z (ESI) 370.1 [M+H⁺].

Synthesis 43—6-Chloro-3-ethynyl-1-(methoxymethyl)-2-phenyl-1H-indole (43)

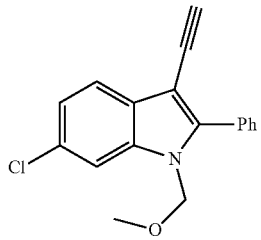 [SMILES: C#Cc1c(-c2ccccc2)n(COC)c2cc(Cl)ccc12]

Using a method analogous to Method M, with 6-chloro-1-(methoxymethyl)-2-phenyl-1H-indole (340 mg, 1.25 mmol), N-iodosuccinimide (287 mg, 1.28 mmol), trimethylsilylacetylene (185 mg, 261 μL, 1.87 mmol), PdCl$_2$(PPh$_3$)$_2$ (43 mg, 0.062 mmol), CuI (12 mg, 0.06 mmol), Et$_3$N (380 mg, 523 μL, 3.76 mmol) and tetra-n-butylammonium fluoride (1.5 mL, 1.5 mmol, 1.0 in THF). Purification by flash column chromatography (silica gel, hexanes:EtOAc 5:1) gave compound 43 (402 mg, 87% for 3 steps) as a colourless oil.

$^1$H NMR (400 MHz, CDCl$_3$) δ=7.75-7.66 (m, 3H), 7.60-7.44 (m, 4H), 7.28 (dd, J=8.4, 1.8 Hz, 1H), 5.35 (s, 2H), 3.28 (s, 3H), 3.19 (s, 1H); $^{13}$C NMR (101 MHz, CDCl$_3$) δ=145.5, 137.0, 130.3, 129.9, 129.4, 129.2, 128.6, 127. 9, 122.4, 120.9, 110.8, 97.4, 80.3, 75.1, 56.1. m/z (ESI) 296.1 [M+H$^+$].

Synthesis 44—6-Chloro-1-(methoxymethyl)-2-phenyl-3-(3,3,3-trifluoroprop-1-yn-1-yl)-1H-indole (44)

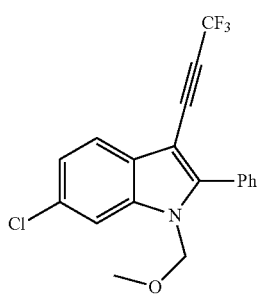 [SMILES: COCn1c(-c2ccccc2)c(C#CC(F)(F)F)c2ccc(Cl)cc21]

Using a method analogous to Method N, with compound 43 (350 mg, 1.18 mmol), N,N,N',N'-tetramethylethylenediamine (206 mg, 266 μL, 1.78 mmol), CuI (338 mg, 1.78 mmol), K$_2$CO$_3$ (491 mg, 3.55 mmol) and trimethyl(trifluoromethyl)silane (673 mg, 700 μL, 4.73 mmol). Purification by flash column chromatography (silica gel, hexanes:EtOAc 4:1) gave compound 44 (362 mg, 84%) as an orange solid.

$^1$H NMR (400 MHz, CDCl$_3$) δ=7.75-7.62 (m, 3H), 7.62-7.47 (m, 4H), 7.31 (dd, J=8.4, 1.7 Hz, 1H), 5.37 (s, 2H), 3.31 (s, 3H); $^{13}$C NMR (101 MHz, CDCl$_3$) δ=148.1, 137.0, 131.1, 131.0, 130.0, 129.9, 128.9, 127.2, 123.1, 120.7, 115.2 (q, J=256.6 Hz), 111.2, 93.9 (q, J=1.9 Hz), 82.2 (q, J=6.4 Hz), 79.1 (q, J=52.1 Hz), 75.2, 56.2; $^{19}$F NMR (376 MHz, CDCl$_3$) δ=−48.90 (s, 3F). m/z (ESI) 364.1 [M+H$^+$].

Synthesis 45—(E)-6-Chloro-1-(methoxymethyl)-2-phenyl-3-(3,3,3-trifluoro-1-iodoprop-1-en-1-yl)-1H-indole (45)

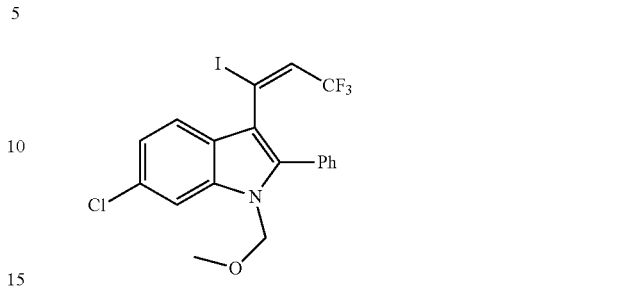

Using a method analogous to Method O, with compound 44 (275 mg, 0.76 mmol), LiI (122 mg, 0.92 mmol). Purification by flash column chromatography (silica gel, hexanes:EtOAc 10:1) gave compound 45 (353 mg, 95%) as pale yellow oil.

$^1$H NMR (400 MHz, CDCl$_3$) δ=7.63-7.50 (m, 7H), 7.30 (dd, J=8.4, 1.8 Hz, 1H), 6.71 (q, J=7.1 Hz, 1H), 5.33 (s, 2H), 3.24 (s, 3H); $^{13}$C NMR (101 MHz, CDCl$_3$) δ=138.6, 136.9, 130.1, 132.6 (q, J=34.2 Hz), 129.8, 129.5, 129.4, 128. 7, 124.5, 122.3, 121.2 (q, J=274.3 Hz), 120.5, 115.8, 103.0 (q, J=6.6 Hz), 110.8, 75.0, 56.0; $^{19}$F NMR (376 MHz, CDCl$_3$) δ=−60.82 (d, J=7.1 Hz, 3F). m/z (ESI) 492.0 [M+H$^+$].

Synthesis 46—(E)-6-Chloro-1-(methoxymethyl)-2-phenyl-3-(3,3,3-trifluoro-1-(furan-2-yl)prop-1-en-1-yl)-1H-indole (46)

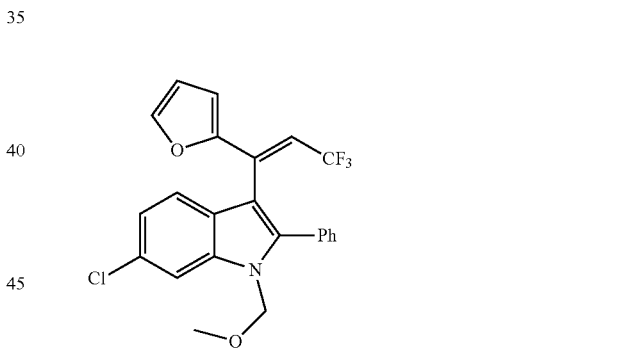

Using a method analogous to Method P, with compound 45 (116 mg, 0.236 mmol), tri-n-butyl(furan-2-yl)stannane (126 mg, 0.353 mmol), P(o-Tol)$_3$ (10.8 mg, 0.035 mmol), PdCl$_2$(MeCN)$_2$ (6.2 mg, 0.024 mmol) and CuI (6.7 mg, 0.035 mmol). Purification by flash column chromatography (silica gel, hexanes:EtOAc 10:1) gave compound 46 (95 mg, 93%) as a colourless oil.

$^1$H NMR (400 MHz, CDCl$_3$) δ=7.60 (d, J=1.7 Hz, 1H), 7.51-7.33 (m, 7H), 7.19 (dd, J=8.5, 1.8 Hz, 1H), 6.47 (q, J=8.3 Hz, 1H), 6.30 (dd, J=3.4, 1.8 Hz, 1H), 6.06 (d, J=3.3 Hz, 1H), 5.40 (s, 2H), 3.24 (s, 3H); $^{13}$C NMR (101 MHz, CDCl$_3$) δ=152.3, 144.0, 139.6, 137.3, 132.5 (q, J=5.8 Hz), 130.2, 130.1, 128.83, 128.80, 128.4, 126.9, 123.4 (q, J=270.0 Hz), 121.9, 120.5, 114.6 (q, J=33.8 Hz), 113.6, 112.0, 110.6, 108.9, 74.9, 55.8; $^{19}$F NMR (376 MHz, CDCl$_3$) δ=−58.00 (d, J=8.3 Hz, 3F). m/z (ESI) 432.1 [M+H$^+$].

Synthesis 47—6-Chloro-2-phenyl-3-(3,3,3-trifluoro-1-(furan-2-yl)propyl)-1H-indole (47, ABD1216)

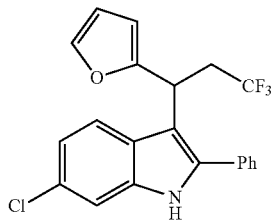 [SMILES: FC(F)(F)CC(c1ccco1)c1c(-c2ccccc2)[nH]c2cc(Cl)ccc12]

Using a method analogous to Method Q, with compound 46 (45 mg, 0.10 mmol), Et$_3$SiH (73 mg, 100 µL, 0.63 mmol) and trifluoroacetic acid (60 mg, 40 µL, 0.53 mmol). Purification by flash column chromatography (silica gel, hexanes:EtOAc 10:1) gave compound 47 (34 mg, 84% for 2 steps) as a white solid.

$^1$H NMR (400 MHz, CDCl$_3$) δ=8.08 (br s, 1H), 7.62-7.43 (m, 6H), 7.43-7.34 (m, 2H), 7.10 (dd, J=8.5, 1.9 Hz, 1H), 6.33 (dd, J=3.2, 1.9 Hz, 1H), 6.11 (dt, J=3.2, 0.9 Hz, 1H), 4.77 (dd, J=8.6, 5.5 Hz, 1H), 3.25-3.03 (m, 1H), 3.03-2.82 (m, 1H); $^{13}$C NMR (101 MHz, CDCl$_3$) δ=155.0, 141.7, 136.8, 136.5, 131.9, 129.0, 128.8, 128.7, 128.2, 126.2 (q, J=277.7 Hz), 125.5, 121.0, 120.6, 111.1, 111.0, 110.4, 106.3, 36.9 (q, J=27.4 Hz), 30.6 (q, J=3.3 Hz); $^{19}$F NMR (376 MHz, CDCl$_3$) δ=−64.70 (t, J=10.6 Hz, 3F). m/z (ESI) 390.1 [M+H$^+$].

Synthesis 48—(E)-6-Chloro-1-(methoxymethyl)-2-phenyl-3-(3,3,3-trifluoro-1-(thiophen-2-yl)prop-1-en-1-yl)-1H-indole (48)

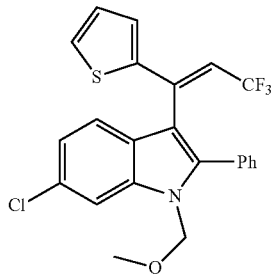 [SMILES: COCn1c(-c2ccccc2)c(/C(=C\C(F)(F)F)c2cccs2)c2ccc(Cl)cc21]

Using a method analogous to Method P, with compound 45 (75 mg, 0.153 mmol), tri-n-butyl(thiophen-2-yl)stannane (85 mg, 0.228 mmol), P(o-Tol)$_3$ (7 mg, 0.023 mmol), PdCl$_2$(MeCN)$_2$ (4.0 mg, 0.015 mmol) and CuI (4.4 mg, 0.023 mmol). Purification by flash column chromatography (silica gel, hexanes:EtOAc 10:1) gave compound 48 (60 mg, 88%) as a colourless oil.

$^1$H NMR (400 MHz, CDCl$_3$) δ=7.61 (s, 1H), 7.47-7.32 (m, 6H), 7.28 (d, J=5.9 Hz, 1H), 7.18 (dd, J=8.5, 1.7 Hz, 1H), 7.02-6.87 (m, 2H), 6.31 (q, J=8.0 Hz, 1H), 5.41 (s, 2H), 3.23 (s, 3H); $^{13}$C NMR (101 MHz, CDCl$_3$) δ=143.8, 139.6, 137.7 (q, J=5.6 Hz), 137.2, 130.2, 128.9, 128.8, 128.4, 128.1, 127.8, 127.7, 126.7, 122.9 (q, J=270.0 Hz), 122.0, 120.6, 115.5 (q, J=33.5 Hz), 111.1, 110.7, 75.0, 55.8; $^{19}$F NMR (376 MHz, CDCl$_3$) δ=−58.24 (d, J=8.0 Hz, 3F). m/z (ESI) 448.1 [M+H$^+$].

Synthesis 49—6-Chloro-2-phenyl-3-(3,3,3-trifluoro-1-(thiophen-2-yl)propyl)-1H-indole (49, ABD1217)

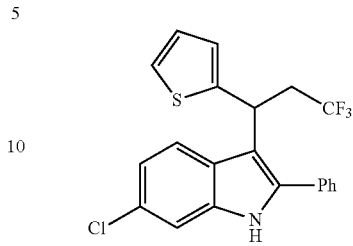

Using a method analogous to Method Q, with compound 48 (60 mg, 0.134 mmol), Et$_3$SiH (94 mg, 130 µL, 0.63 mmol) and trifluoroacetic acid (75 mg, 50 µL, 0.658 mmol). Purification by flash column chromatography (silica gel, hexanes:EtOAc 10:1) to give compound 49 (41 mg, 75% for 2 steps) as a white solid.

$^1$H NMR (400 MHz, CDCl$_3$) δ=8.09 (br s, 1H), 7.59-7.37 (m, 7H), 7.20 (d, J=4.7 Hz, 1H), 7.08 (dd, J=8.6, 1.6 Hz, 1H), 7.00-6.87 (m, 2H), 4.93 (dd, J=9.3, 4.7 Hz, 1H), 3.28-2.94 (m, 2H); $^{13}$C NMR (101 MHz, CDCl$_3$) δ=147.4, 136.8, 136.6, 131.9, 129.0, 128.7, 128.7, 128.23 126.8, 126.1 (q, J=278.3 Hz), 125.3, 124.3, 124.1, 120.9, 120.7, 112.9, 111.2, 39.3 (q, J=27.3 Hz), 31.9 (q, J=3.2 Hz); $^{19}$F NMR (376 MHz, CDCl$_3$) δ=−64.41 (t, J=10.3 Hz, 3F). m/z (ESI) 406.1 [M+H$^+$].

Synthesis 50—(Z)-6-Chloro-1-(methoxymethyl)-2-phenyl-3-(3,3,3-trifluoro-1-phenylprop-1-en-1-yl)-1H-indole (50)

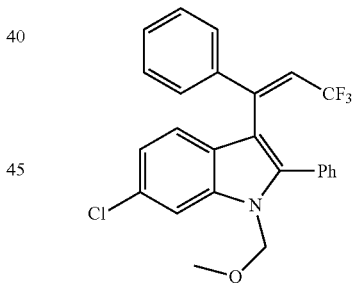

Using a method analogous to Method P, with compound 45 (130 mg, 0.264 mmol), tri-n-butyl(phenyl)stannane (146 mg, 0.397 mmol), P(o-Tol)$_3$ (12 mg, 0.039 mmol), PdCl$_2$(MeCN)$_2$ (7.0 mg, 0.027 mmol) and CuI (7.6 mg, 0.040 mmol). Purification by flash column chromatography (silica gel, hexanes:EtOAc 10:1) to give compound 50 (109 mg, 93%) as a pale yellow oil.

$^1$H NMR (400 MHz, CDCl$_3$) δ=7.59 (d, J=1.8 Hz, 1H), 7.36-7.26 (m, 7H), 7.26-7.20 (m, 4H), 7.16 (dd, J=8.5, 1.8 Hz, 1H), 6.26 (q, J=8.1 Hz, 1H), 5.38 (s, 2H), 3.23 (s, 3H); $^{13}$C NMR (101 MHz, CDCl$_3$) δ=144.5 (q, J=5.6 Hz), 139.8, 139.7, 137.3, 130.22, 130.19, 129.2, 128.8, 128.7, 128.6, 128.4, 128.3, 127.2, 127.0, 123.0 (q, J=270.7 Hz), 121.9, 120.7, 112.0, 117.9 (q, J=5.6 Hz), 110.6, 74.9, 55.8; $^{19}$F NMR (376 MHz, CDCl$_3$) δ=−59.00 (d, J=8.0 Hz, 3F). m/z (ESI) 442.1 [M+H$^+$].

Synthesis 51—6-Chloro-2-phenyl-3-(3,3,3-trifluoro-1-phenylpropyl)-1H-indole (51, ABD1218)

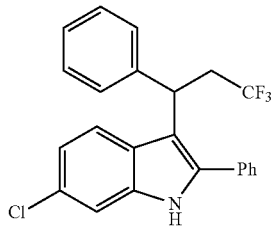 [SMILES: FC(F)(F)CC(c1ccccc1)c1c(-c2ccccc2)[nH]c2cc(Cl)ccc12]

Using a method analogous to Method Q, with compound 48 (81 mg, 0.183 mmol), Et₃SiH (128 mg, 176 µL, 1.10 mmol) and trifluoroacetic acid (105 mg, 70 µL, 0.921 mmol). Purification by flash column chromatography (silica gel, hexanes:EtOAc 10:1) gave compound 51 (63 mg, 86% for 2 steps) as a white solid.

$^1$H NMR (400 MHz, CDCl₃) δ=8.08 (br s, 1H), 7.59-7.38 (m, 6H), 7.37-7.18 (m, 6H), 7.09 (dd, J=8.5, 1.9 Hz, 1H), 4.76 (dd, J=9.0, 5.2 Hz, 1H), 3.25-2.89 (m, 2H); $^{13}$C NMR (101 MHz, CDCl₃) δ=142.7, 136.7, 136.6, 132.2, 128.9, 128.8, 128.63, 128.61, 128.1, 127.3, 126.62, 126.59 (q, J=278.3 Hz), 125.8, 121.0, 120.7, 113.2, 111.2, 39.3 (q, J=27.3 Hz), 31.9 (q, J=3.2 Hz); $^{19}$F NMR (376 MHz, CDCl₃) δ=−64.35 (t, J=10.7 Hz, 3F). m/z (ESI) 400.1 [M+H⁺].

Synthesis 52—1-Iodo-2-nitro-4-(trifluoromethyl)benzene (52)

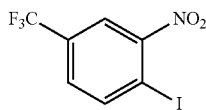

Method R: A solution of 2-nitro-4-(trifluoromethyl)aniline (808 mg, 3.92 mmol) in conc. HCl (12 M, 7 mL) was heated at 100° C. for 5 min. The solution was then cooled to 0° C. before a solution of NaNO₂ (500 mg, 5.88 mmol) in H₂O (2 mL) was added dropwise at 0° C. The resulting mixture was stirred for 1 h prior to adding a solution of KI (1.301 g, 7.85 mmol) in H₂O (2 mL) at 0° C. The resulting mixture was stirred at 23° C. for further 1 h before H₂O (10 mL) was added and diluted with EtOAc (30 mL). The layers were separated, and the organic layer was extracted with H₂O (3×10 mL). The combined organic layers were dried over Na₂SO₄ and concentrated in vacuo. The residue was purified by flash column chromatography (silica gel, hexanes:EtOAc 10:1) to give compound 52 (920 mg, 74%) as a yellow oil.

$^1$H NMR (400 MHz, CDCl₃) δ=8.24 (d, J=8.3 Hz, 1H), 8.13 (d, J=1.7 Hz, 1H), 7.54 (dd, J=8.3, 2.0 Hz, 1H); $^{19}$F NMR (376 MHz, CDCl₃) δ=−63.22. m/z (ESI) 317.9 [M+H⁺].

Synthesis 53—2-Iodo-5-(trifluoromethyl)aniline (53)

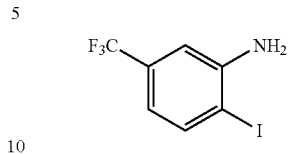

Method S: To a solution of compound 52 (850 mg, 2.68 mmol) in HOAc-EtOH (10 mL, 1:5, v/v) was added iron dust (750 mg, 13.43 mmol) at 23° C. The resulting mixture was stirred at 23° C. for 3 h before it was quenched with a saturated solution of NaHCO₃ (20 mL) and diluted with EtOAc (50 mL). The layers were separated, and the organic layer was extracted with H₂O (3×10 mL). The combined organic layers were dried over Na₂SO₄ and concentrated in vacuo. The residue was purified by flash column chromatography (silica gel, hexanes:EtOAc 10:1) to give compound 53 (754 mg, 98%) as a yellow solid.

$^1$H NMR (400 MHz, CDCl₃) δ=7.76 (dd, J=8.2, 0.7 Hz, 1H), 6.96 (d, J=1.7 Hz, 1H), 6.72 (ddd, J=8.2, 2.0, 0.6 Hz, 1H), 4.32 (brs, 2H). m/z (ESI) 288.0 [M+H⁺].

Synthesis 54—2-(Phenylethynyl)-5-(trifluoromethyl)aniline (54)

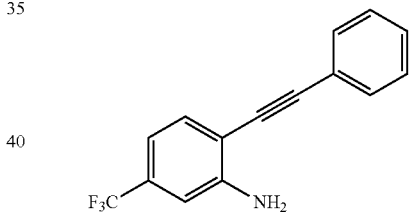

Method T: To a solution of compound 53 (620 mg, 2.16 mmol) in DMF (5 mL) was added phenylacetylene (331 mg, 356 µL, 3.24 mmol), PdCl₂(PPh₃)₂ (76 mg, 0.108 mmol), CuI (25 mg, 0.131 mmol) and Et₃N (656 mg, 903 µL, 6.48 mmol) at 23° C. The reaction mixture was stirred for 6 h at 23° C. before it was quenched with a saturated solution of NH₄Cl (10 mL) and diluted with EtOAc (50 mL). The layers were separated, and the organic layer was extracted with H₂O (3×10 mL). The combined organic layers were dried over Na₂SO₄ and concentrated in vacuo. The residue was purified by flash column chromatography (silica gel, hexanes:EtOAc 5:1) to give compound 54 (518 mg, 92%) as pale yellow solid.

$^1$H NMR (400 MHz, CDCl₃) δ=7.56 (m, 2H), 7.47 (dd, J=8.5, 0.8 Hz, 1H), 7.42-7.38 (m, 3H), 6.98-6.96 (m, 2H), 4.48 (brs, 2H); $^{13}$C NMR (101 MHz, CDCl₃) δ=147.8, 132.5, 131.6, 131.5 (q, J=32.2 Hz), 128.7, 128.5, 124.0 (q, J=272.3 Hz), 122.6, 114.3 (q, J=3.8 Hz), 111.2, 110.7 (q, J=4.0 Hz), 96.5, 84.6; $^{19}$F NMR (376 MHz, CDCl₃) δ=−63.13. m/z (ESI) 262.1 [M+H⁺].

Synthesis 55—2-Phenyl-6-(trifluoromethyl)-1H-indole (55)

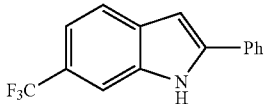 [SMILES: FC(F)(F)c1ccc2cc(-c3ccccc3)[nH]c2c1]

Method U: To a solution of compound 54 (518 mg, 1.98 mmol) in toluene (10 mL) was added ZnBr$_2$ (45 mg, 0.2 mmol) at 23° C. The resulting mixture was heated to 120° C. for 3 h before it was quenched with a saturated solution of NH$_4$Cl (10 mL) and diluted with EtOAc (50 mL). The layers were separated, and the organic layer was extracted with H$_2$O (3×10 mL). The combined organic layers were dried over Na$_2$SO$_4$ and concentrated in vacuo. The residue was purified by flash column chromatography (silica gel, hexanes:EtOAc 5:1) to give compound 55 (450 mg, 86%) as pale yellow solid.

$^1$H NMR (400 MHz, CDCl$_3$) δ=8.55 (brs, 1H), 7.74-7.69 (m, 4H), 7.53-7.48 (m, 2H), 7.43-7.36 (m, 2H), 6.90 (dd, J=2.1, 0.8 Hz, 1H); $^{13}$C NMR (101 MHz, CDCl$_3$) δ=140.6, 135.6, 131.6, 129.2, 128.5, 125.4, 125.2 (q, J=271.4 Hz), 124.2 (q, J=32.1 Hz), 120.9, 117.0 (q, J=3.4 Hz), 108.4 (q, J=4.4 Hz), 100.0; $^{19}$F NMR (376 MHz, CDCl$_3$) δ=−60.86. m/z (ESI) 262.1 [M+H$^+$].

Synthesis 56—1-(Methoxymethyl)-2-phenyl-6-(trifluoromethyl)-1H-indole (56)

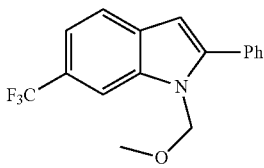 [SMILES: COCn1c(-c2ccccc2)cc2ccc(C(F)(F)F)cc21]

Method V: To a solution of compound 55 (439 mg, 1.68 mmol) in THF (5 mL) was added NaH (100 mg, 2.5 mmol, 60% in mineral oil) at 0° C. The resulting mixture was stirred at 0° C. for 30 min before chloromethyl methyl ether (161 mg, 152 µL, 2 mmol) was added. The reaction mixture was stirred for a further 2 h before it was quenched with a saturated solution of NH$_4$Cl (20 mL) and diluted with CH$_2$Cl$_2$ (10 mL). The resulting mixture was extracted with CH$_2$Cl$_2$ (3×10 mL), the combined organic layers were dried over Na$_2$SO$_4$ and concentrated in vacuo. The residue was purified by flash column chromatography (silica gel, hexanes:EtOAc 10:1) to give compound 56 (451 mg, 88%).

$^1$H NMR (400 MHz, CDCl$_3$) δ=7.83 (s, 1H), 7.74 (d, J=8.3 Hz, 1H), 7.68-7.59 (m, 2H), 7.59-7.39 (m, 4H), 6.69 (d, J=0.6 Hz, 1H), 5.48 (s, 2H), 3.34 (s, 3H); $^{13}$C NMR (101 MHz, CDCl$_3$) δ=144.5, 137.1, 132.5, 131.7, 130.8, 129.6, 128.9, 128.8, 125.2 (q, J=271.6 Hz), 124.3 (q, J=30.6 Hz), 120.9, 117.5 (q, J=3.4 Hz), 107.8 (q, J=4.2 Hz), 103.8, 74.8, 56.0; $^{19}$F NMR (376 MHz, CDCl$_3$) δ=−60.48. m/z (ESI) 306.1 [M+H$^+$].

Synthesis 57—3-Ethynyl-1-(methoxymethyl)-2-phenyl-6-(trifluoromethyl)-1H-indole (57)

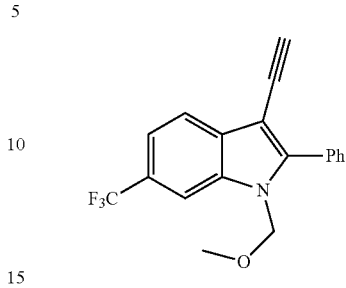

Using a method analogous to Method M, with compound 56 (422 mg, 1.38 mmol), N-iodosuccinimide (317 mg, 1.41 mmol), trimethylsilylacetylene (213 mg, 300 µL, 2.17 mmol), PdCl$_2$(PPh$_3$)$_2$ (48 mg, 0.069 mmol), CuI (16 mg, 0.084 mmol), Et$_3$N (419 mg, 577 µL, 4.14 mmol) and tetra-n-butylammonium fluoride (1.67 mL, 1.67 mmol, 1.0 M in THF). Purification by flash column chromatography (silica gel, hexanes:EtOAc 5:1) gave compound 57 (368 mg, 81% for 3 steps) as a colourless oil.

$^1$H NMR (400 MHz, CDCl$_3$) δ=7.88 (d, J=8.3 Hz, 1H), 7.83 (d, J=0.6 Hz, 1H), 7.76-7.68 (m, 2H), 7.61-7.47 (m, 5H), 5.44 (s, 2H), 3.30 (s, 3H), 3.19 (s, 1H); $^{13}$C NMR (101 MHz, CDCl$_3$) δ=147.2, 135.6, 131.7, 131.0, 130.3, 129.6, 129.5, 128.7, 125.6 (q, J=31.9 Hz), 124.9 (q, J=271.0 Hz), 120.5, 118.3 (q, J=3.5 Hz), 108.2 (q, J=4.2 Hz), 97.6, 80.5, 75.1, 56.1; $^{19}$F NMR (376 MHz, CDCl$_3$) δ=−60.68. m/z (ESI) 330.1 [M+H$^+$].

Synthesis 58—1-(Methoxymethyl)-2-phenyl-6-(trifluoromethyl)-3-(3,3,3-trifluoroprop-1-yn-1-yl)-1H-indole (58)

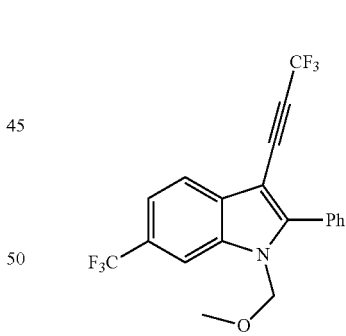

Using a method analogous to Method N, with compound 57 (255 mg, 0.774 mmol), N,N,N',N'-tetramethylethylenediamine (136 mg, 186 µL, 1.17 mmol), CuI (223 mg, 1.17 mmol), K$_2$CO$_3$ (321 mg, 2.32 mmol) and trimethyl(trifluoromethyl)silane (440 mg, 458 µL, 3.1 mmol). Purification by flash column chromatography (silica gel, hexanes:EtOAc 4:1) gave compound 58 (283 mg, 92%) as an orange solid.

$^1$H NMR (400 MHz, CDCl$_3$) δ=7.89-7.83 (m, 2H), 7.72-7.65 (m, 2H), 7.64-7.54 (m, 4H), 5.46 (s, 2H), 3.32 (s, 3H); $^{13}$C NMR (101 MHz, CDCl$_3$) δ=149.7, 135.7, 130.2, 130.1, 128.9, 128.6, 126.3 (q, J=32.1 Hz), 124.7 (q, J=271.8 Hz), 123.4, 120.3, 119.1 (q, J=3.1 Hz), 115.2 (q, J=256.9

Hz), 108.7 (q, J=4.3 Hz), 94.1 (q, J=1.5 Hz), 81.7 (q, J=6.3 Hz), 79.2 (q, J=52.6 Hz), 75.3, 56.3; $^{19}$F NMR (376 MHz, CDCl$_3$) δ=−49.02 (s, 3F), −60.88 (s, 3F). m/z (ESI) 398.1 [M+H$^+$].

Synthesis 59—(E)-1-(Methoxymethyl)-2-phenyl-3-(3,3,3-trifluoro-1-iodoprop-1-en-1-yl)-6-(trifluoromethyl)-1H-indole (59)

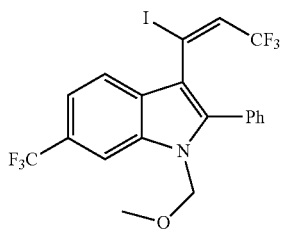 [SMILES: COCn1c(-c2ccccc2)c(/C(I)=C\C(F)(F)F)c2ccc(C(F)(F)F)cc21]

Using a method analogous to Method O, with compound 58 (268 mg, 0.67 mmol), LiI (108 mg, 0.81 mmol). Purification by flash column chromatography (silica gel, hexanes:EtOAc 10:1) gave compound 59 (333 mg, 94%; ca. 1:10 mixture of inseparable stereoisomers determined by $^1$H NMR) as pale yellow solid.

$^1$H NMR (400 MHz, CDCl$_3$) δ=7.87 (d, J=1.3 Hz, 1H), 7.78 (d, J=8.3 Hz, 1H), 7.65-7.51 (m, 6H), 6.75 (q, J=7.1 Hz, 1H), 5.43 (s, 2H), 3.25 (d, 3H); $^{19}$F NMR (376 MHz, CDCl$_3$) δ=−60.74 (s, 3F); −60.84 (d, J=7.1 Hz, 3F). m/z (ESI) 526.0 [M+H$^+$].

Synthesis 60—(Z)-1-(Methoxymethyl)-2-phenyl-3-(3,3,3-trifluoro-1-phenylprop-1-en-1-yl)-6-(trifluoromethyl)-1H-indole (60)

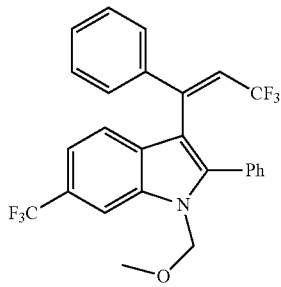 [SMILES: COCn1c(-c2ccccc2)c(/C(=C\C(F)(F)F)c2ccccc2)c2ccc(C(F)(F)F)cc21]

Using a method analogous to Method P, with compound 59 (130 mg, 0.248 mmol), tri-n-butyl(phenyl)stannane (136 mg, 0.370 mmol), P(o-Tol)$_3$ (11.5 mg, 0.038 mmol), PdCl$_2$(MeCN)$_2$ (6.5 mg, 0.025 mmol) and CuI (7.1 mg, 0.037 mmol). Purification by flash column chromatography (silica gel, hexanes:EtOAc 10:1) gave compound 60 (68 mg, 58%; ca. 1:8 mixture of inseparable stereoisomers determined by $^1$H NMR) as a colourless oil.

$^1$H NMR (400 MHz, CDCl$_3$) δ=7.93 (s, 1H), 7.55 (d, J=8.3 Hz, 1H), 7.53-7.44 (m, 1H), 7.44-7.35 (m, 5H), 7.35-7.20 (m, 5H), 6.34 (q, J=8.1 Hz, 1H), 5.50 (s, 2H), 3.27 (s, 3H); $^{19}$F NMR (376 MHz, CDCl$_3$) δ=−58.91 (d, J=8.1 Hz, 3F), −60.53 (s, 3F). m/z (ESI) 476.1 [M+H$^+$].

Synthesis 61—2-Phenyl-3-(3,3,3-trifluoro-1-phenylpropyl)-6-(trifluoromethyl)-1H-indole (61, ABD1221)

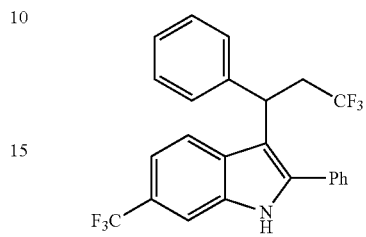

Using a method analogous to Method Q, with compound 60 (50 mg, 0.105 mmol), Et$_3$SiH (73 mg, 100 μL, 0.63 mmol) and trifluoroacetic acid (60 mg, 40 μL, 0.53 mmol). Purification by flash column chromatography (silica gel, hexanes:EtOAc 10:1) gave compound 61 (33 mg, 72% for 2 steps) as a white solid.

$^1$H NMR (400 MHz, CDCl$_3$) δ=8.30 (brs, 1H), 7.75-7.60 (m, 2H), 7.60-7.42 (m, 5H), 7.42-7.13 (m, 6H), 4.83 (dd, J=9.2, 5.0 Hz, 1H), 3.30-2.90 (m, 2H); $^{13}$C NMR (101 MHz, CDCl$_3$) δ=142.6, 138.8, 135.0, 131.9, 129.4, 129.02, 128.96, 128.9, 128.7, 127.3, 126.7, 126.6 (q, J=277.8 Hz), 125.1 (q, J=271.8 Hz), 124.3 (q, J=31.7 Hz), 120.5, 116.7 (q, J=3.4 Hz), 113.5, 108.8 (q, J=4.2 Hz), 38.7 (q, J=27.1 Hz), 35.6 (q, J=2.6 Hz); $^{19}$F NMR (376 MHz, CDCl$_3$) δ=−60.71 (s, 3F), −64.28 (t, J=10.5 Hz). m/z (ESI) 434.1 [M+H$^+$].

Synthesis 62—(E)-1-(Methoxymethyl)-2-phenyl-3-(3,3,3-trifluoro-1-(thiophen-2-yl)prop-1-en-1-yl)-6-(trifluoromethyl)-1H-indole (62)

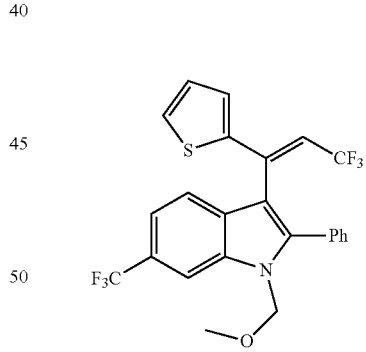

Using a method analogous to Method P, with compound 59 (100 mg, 0.190 mmol), tri-n-butyl(thiophen-2-yl)stannane (106 mg, 0.286 mmol), P(o-Tol)$_3$ (8.7 mg, 0.029 mmol), PdCl$_2$(MeCN)$_2$ (5 mg, 0.019 mmol) and CuI (5.4 mg, 0.028 mmol). Purification by flash column chromatography (silica gel, hexanes:EtOAc 10:1) gave compound 62 (85 mg, 93%; ca. 1:8 mixture of inseparable stereoisomers determined by $^1$H NMR) as a colourless oil.

$^1$H NMR (400 MHz, CDCl$_3$) δ=7.92 (s, 1H), 7.62-7.52 (m, 1H), 7.52-7.39 (m, 5H), 7.32-7.24 (m, 2H), 6.99-6.89 (m, 2H), 6.36 (q, J=8.0 Hz, 1H), 5.51 (s, 2H), 3.26 (s, 3H); $^{19}$F NMR (376 MHz, CDCl$_3$) δ=−58.20 (d, J=8.0 Hz, 3F), −60.56 (s, 3F). m/z (ESI) 482.1 [M+H$^+$].

Synthesis 63—2-Phenyl-3-(3,3,3-trifluoro-1-(thiophen-2-yl)propyl)-6-(trifluoromethyl)-1H-indole (63, ABD1221)

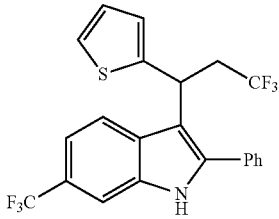 [SMILES: FC(F)(F)CC(c1cccs1)c1c(-c2ccccc2)[nH]c2cc(C(F)(F)F)ccc12]

Using a method analogous to Method Q, with compound 62 (56 mg, 0.116 mmol), Et$_3$SiH (81 mg, 112 µL, 0.698 mmol) and trifluoroacetic acid (67 mg, 45 µL, 0.588 mmol). Purification by flash column chromatography (silica gel, hexanes:EtOAc 10:1) gave compound 63 (42 mg, 82% for 2 steps) as a white solid.

$^1$H NMR (400 MHz, CDCl$_3$) δ=8.37 (brs, 1H), 7.71 (s, 1H), 7.65-7.43 (m, 6H), 7.36 (d, J=8.4 Hz, 1H), 7.21 (d, J=5.0 Hz, 1H), 7.02-6.83 (m, 2H), 4.97 (dd, J=9.5, 4.6 Hz, 1H), 3.33-2.94 (m, 2H); $^{13}$C NMR (101 MHz, CDCl$_3$) δ=147.2, 138.8, 135.0, 131.6, 129.08, 129.06, 128.95, 128.8, 126.9, 126.1 (q, J=277.6 Hz), 125.0 (q, J=271.6 Hz), 124.40, 124.38 (q, J=32.2 Hz), 124.2, 120.4, 116.7 (q, J=3.6 Hz), 113.2, 108.8 (q, J=4.3 Hz), 39.3 (q, J=27.3 Hz), 31.9 (q, J=2.8 Hz); $^{19}$F NMR (376 MHz, CDCl$_3$) δ=−60.77 (s, 3F), −64.40 (t, J=10. Hz). m/z (ESI) 440.1 [M+H$^+$].

Synthesis 64—2-(Cyclopentylethynyl)-5-(trifluoromethyl)aniline (64)

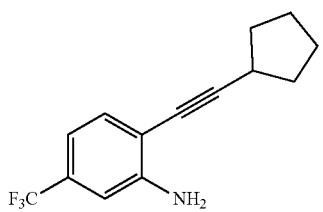 [SMILES: Nc1cc(C(F)(F)F)ccc1C#CC1CCCC1]

Using a method analogous to Method T, with compound 53 (440 mg, 1.53 mmol), cyclopentylacetylene (216 mg, 266 µL, 2.26 mmol), PdCl$_2$(PPh$_3$)$_2$ (54 mg, 0.077 mmol), CuI (18 mg, 0.095 mmol) and Et$_3$N (464 mg, 640 µL, 4.59 mmol). Purification by flash column chromatography (silica gel, hexanes:EtOAc 5:1) gave compound 64 (326 mg, 84%) as a colourless oil.

$^1$H NMR (400 MHz, CDCl$_3$) δ=7.34 (dd, J=8.5, 0.7 Hz, 1H), 6.97-6.87 (m, 2H), 4.36 (brs, 2H), 2.93 (quintet, J=7.4 Hz, 1H), 2.14-1.98 (m, 2H), 1.89-1.71 (m, 4H), 1.71-1.56 (m, 2H); $^{13}$C NMR (101 MHz, CDCl$_3$) δ=147.6, 132.3, 130.4 (q, J=31.8 Hz), 124.1 (q, J=272.6 Hz), 114.1 (q, J=3.8 Hz), 112.3, 110.4 (q, J=4.1 Hz), 102.4, 75.5, 34.1, 31.0, 25.1; $^{19}$F NMR (376 MHz, CDCl$_3$) δ=−62.97 (s, 3F). m/z (ESI) 254.1 [M+H$^+$].

Synthesis 65—2-Cyclopentyl-6-(trifluoromethyl)-1H-indole (65)

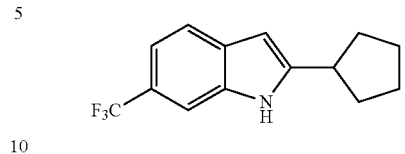

Using a method analogous to Method U, with compound 64 (310 mg, 1.22 mmol) and ZnBr$_2$ (28 mg, 0.124 mmol). Purification by flash column chromatography (silica gel, hexanes:EtOAc 5:1) gave compound 65 (286 mg mg, 92%) as a colourless solid.

$^1$H NMR (400 MHz, CDCl$_3$) δ=8.07 (brs, 1H), 7.65 (dd, J=8.3, 0.5 Hz, 1H), 7.61 (d, J=0.7 Hz, 1H), 7.39 (dd, J=8.3 Hz, 1.1, 1H), 6.38 (dt, J=1.8, 0.8 Hz, 1H), 3.22 (quintet, J=7.8 Hz, 1H), 2.30-2.04 (m, 2H), 1.99-1.71 (m, 6H); $^{13}$C NMR (101 MHz, CDCl$_3$) δ=147.2, 134.7, 128.3, 125.5 (q, J=271.7 Hz), 122.9 (q, J=31.6 Hz), 120.0, 116.4 (q, J=3.5 Hz), 107.8 (q, J=4.3 Hz), 98.4, 38.9, 32.8, 25.2; $^{19}$F NMR (376 MHz, CDCl$_3$) δ=−60.19 (s, 3F). m/z (ESI) 254.1 [M+H$^+$].

Synthesis 66—2-cyclopentyl-1-(methoxymethyl)-6-(trifluoromethyl)-1H-indole (66)

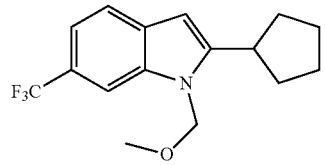 [SMILES: COCn1c(C2CCCC2)cc2ccc(C(F)(F)F)cc21]

Using a method analogous to Method V, with compound 65 (286 mg, 1.13 mmol), NaH (68 mg, 1.69 mmol, 60% in mineral oil) and chloromethyl methyl ether (109 mg, 103 µL, 1.36 mmol). Purification by flash column chromatography (silica gel, hexanes:EtOAc 10:1) gave compound 66 (308 mg, 92%) as a colourless oil.

$^1$H NMR (400 MHz, CDCl$_3$) δ=7.69 (s, 1H), 7.61 (d, J=8.2 Hz, 1H), 7.36 (d, J=8.2 Hz, 1H), 6.42 (s, 1H), 5.53 (s, 2H), 3.37-3.26 (m, 4H), 2.26-2.08 (m, 2H), 1.95-1.81 (m, 2H), 1.81-1.67 (m, 4H); $^{13}$C NMR (101 MHz, CDCl$_3$) δ=149.1, 136.7, 130.8, 125.3 (q, J=270.2 Hz), 123.2 (q, J=31.8 Hz), 120.1, 116.9 (q, J=3.6 Hz), 106.6 (q, J=4.5 Hz), 98.9, 74.0, 55.9, 36.8, 33.3, 25.3; $^{19}$F NMR (376 MHz, CDCl$_3$) δ=−60.34 (s, 3F). m/z (ESI) 298.1 [M+H$^+$].

Synthesis 67—2-Cyclopentyl-3-ethynyl-1-(methoxymethyl)-6-(trifluoromethyl)-1H-indole (67)

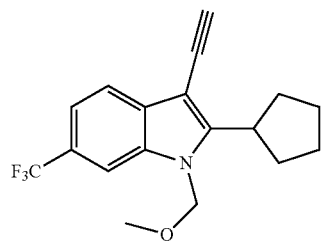 [SMILES: C#Cc1c(C2CCCC2)n(COC)c2cc(C(F)(F)F)ccc12]

Using a method analogous to Method M, with compound 66 (290 mg, 0.98 mmol), N-iodosuccinimide (225 mg, 1.00 mmol), trimethylsilylacetylene (144 mg, 203 µL, 1.46 mmol), PdCl$_2$(PPh$_3$)$_2$ (34 mg, 0.049 mmol), CuI (11 mg, 0.059 mmol), Et$_3$N (296 mg, 408 µL, 2.93 mmol) and tetra-n-butylammonium fluoride (1.17 mL, 1.17 mmol, 1.0 M in THF). Purification by flash column chromatography (silica gel, hexanes:EtOAc 5:1) gave compound 67 (272 mg, 87% for 3 steps) as a colourless oil.

$^1$H NMR (400 MHz, CDCl$_3$) δ=7.78 (d, J=8.3 Hz, 1H), 7.71 (s, 1H), 7.47 (dd, J=8.3, 0.9 Hz, 1H), 5.53 (s, 2H), 3.51 (s, 1H), 3.41 (quintet, J=9.0 Hz, 1H), 3.31 (s, 3H), 2.41-2.24 (m, 2H), 2.19-2.08 (m, 2H), 2.08-1.95 (m, 2H), 1.85-1.70 (m, 2H); $^{13}$C NMR (101 MHz, CDCl$_3$) δ=152.2, 135.1, 132.4, 125.1 (q, J=272.2 Hz), 124.6 (q, J=31.9 Hz), 119.5, 117.8 (q, J=3.5 Hz), 107.0 (q, J=4.4 Hz), 94.8, 83.4, 76.8, 73.9, 55.9, 37.3, 32.8, 26.5; $^{19}$F NMR (376 MHz, CDCl$_3$) δ=−60.47 (s, 3F). m/z (ESI) 322.1 [M+H$^+$].

Synthesis 68—2-Cyclopentyl-1-(methoxymethyl)-6-(trifluoromethyl)-3-(3,3,3-trifluoroprop-1-yn-1-yl)-1H-indole (68)

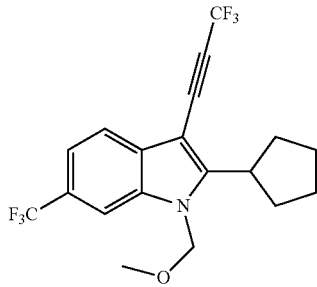 [SMILES: COCn1c(C2CCCC2)c(C#CC(F)(F)F)c2ccc(C(F)(F)F)cc21]

Using a method analogous to Method N, with compound 67 (266 mg, 0.83 mmol), N,N,N',N'-tetramethylethylenediamine (144 mg, 198 µL, 1.24 mmol), CuI (237 mg, 1.24 mmol), K$_2$CO$_3$ (343 mg, 2.48 mmol) and trimethyl(trifluoromethyl)silane (471 mg, 490 µL, 3.32 mmol). Purification by flash column chromatography (silica gel, hexanes:EtOAc 6:1) gave compound 68 (310 mg, 96%) as an orange oil.

$^1$H NMR (400 MHz, CDCl$_3$) δ=7.78-7.67 (m, 2H), 7.50 (dd, J=8.3, 0.9 Hz, 1H), 5.55 (s, 2H), 3.45 (quintet, J=8.9 Hz, 1H), 3.34 (s, 3H), 2.32-2.11 (m, 4H), 2.11-1.93 (m, 2H), 1.86-1.72 (m, 2H); $^{13}$C NMR (101 MHz, CDCl$_3$) δ=155.7, 135.1, 131.6, 125.4 (q, J=31.8 Hz), 124.6 (q, J=271.6 Hz), 119.4, 118.6 (q, J=3.5 Hz), 115.6 (q, J=256.4 Hz), 107.4 (q, J=4.2 Hz), 91.1 (q, J=1.8 Hz), 82.5 (q, J=52.2 Hz), 81.9 (q, J=6.5 Hz), 74.0, 56.1, 37.3, 33.3, 26.6; $^{19}$F NMR (376 MHz, CDCl$_3$) δ=−48.91, (s, 3F), −60.76 (s, 3F). m/z (ESI) 390.1 [M+H$^+$].

Synthesis 69—(E)-2-Cyclopentyl-1-(methoxymethyl)-3-(3,3,3-trifluoro-1-iodoprop-1-en-1-yl)-6-(trifluoromethyl)-1H-indole (69)

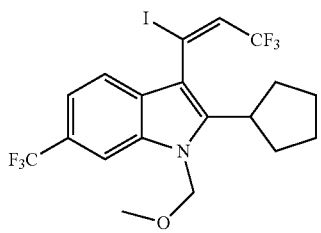 [SMILES: COCn1c(C2CCCC2)c(/C(I)=C\C(F)(F)F)c2ccc(C(F)(F)F)cc21]

Using a method analogous to Method O, with compound 68 (72 mg, 0.85 mmol), LiI (30 mg, 0.224 mmol). Due to instability of the compound 69, crude product was used without further purification.

Synthesis 70—(E)-2-Cyclopentyl-1-(methoxymethyl)-3-(3,3,3-trifluoro-1-(thiophen-2-yl)prop-1-en-1-yl)-6-(trifluoromethyl)-1H-indole (70)

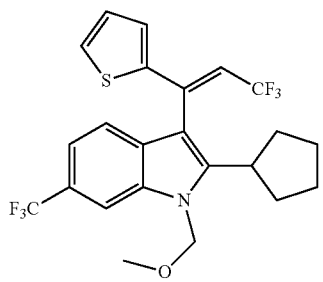 [SMILES: COCn1c(C2CCCC2)c(/C(=C\C(F)(F)F)c2cccs2)c2ccc(C(F)(F)F)cc21]

Using a method analogous to Method P, with crude compound 69 (54 mg, 0.104 mmol), tri-n-butyl(thiophen-2-yl)stannane (58 mg, 0.155 mmol), P(o-Tol)$_3$ (4.8 mg, 0.016 mmol), PdCl$_2$(MeCN)$_2$ (2.7 mg, 0.010 mmol) and CuI (3.0 mg, 0.016 mmol). Purification by flash column chromatography (silica gel, hexanes:EtOAc 10:1) gave compound 70 (35 mg, 71%; ca. 1:10 mixture of inseparable stereoisomers determined by $^1$H NMR) as a colourless oil.

$^1$H NMR (400 MHz, CDCl$_3$) δ=7.73 (s, 1H), 7.40 (d, J=8.3 Hz, 1H), 7.36-7.31 (m, 2H), 6.95 (dd, J=5.0, 3.7 Hz, 1H), 6.91-6.85 (m, 1H), 6.45 (q, J=7.8 Hz, 1H), 5.58 (s, 2H), 3.45-3.21 (m, 4H), 2.25-2.08 (m, 1H), 2.08-1.94 (m, 1H), 1.94-1.80 (m, 2H), 1.80-1.56 (m, 4H); $^{19}$F NMR (376 MHz, CDCl$_3$) δ=−57.81 (d, J=7.8 Hz, 3F), −60.48 (s, 3F). m/z (ESI) 474.1 [M+H$^+$].

Synthesis 71—2-Cyclopentyl-3-(3,3,3-trifluoro-1-(thiophen-2-yl)propyl)-6-(trifluoromethyl)-1H-indole (71, ABD1223)

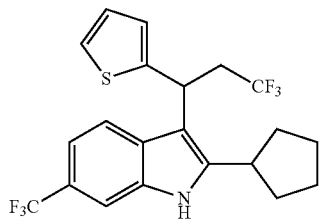 [SMILES: FC(F)(F)CC(c1cccs1)c1c(C2CCCC2)[nH]c2cc(C(F)(F)F)ccc12]

Using a method analogous to Method Q, with compound 70 (35 mg, 0.074 mmol), Et$_3$SiH (52 mg, 72 µL, 0.451 mmol) and trifluoroacetic acid (42 mg, 28 µL, 0.366 mmol). Purification by flash column chromatography (silica gel, hexanes:EtOAc 10:1) gave compound 71 (26 mg, 81% for 2 steps) as a colourless oil.

$^1$H NMR (400 MHz, CDCl$_3$) δ=8.10 (brs, 1H), 7.61 (s, 1H), 7.43 (d, J=8.3 Hz, 1H), 7.26 (dd, J=8.3, 0.8 Hz, 1H), 7.17 (dd, J=5.0, 0.8 Hz, 1H), 6.94 (dd, J=5.0, 3.6 Hz, 1H), 6.91 (dd, J=2.9, 1.7 Hz, 1H), 4.88 (dd, J=8.7, 5.6 Hz, 1H), 3.41 (quintet, J=8.6 Hz, 1H), 3.26-3.03 (m, 2H), 2.27-2.05 (m, 2H), 1.99-1.64 (m, 6H); $^{13}$C NMR (101 MHz, CDCl$_3$)

δ=147.3, 142.6, 134.7, 128.9, 126.7, 126.3 (q, J=279.1 Hz), 125.2 (q, J=270.0 Hz), 124.3, 123.9, 123.3 (q, J=32.0 Hz), 119.2, 116.2 (q, J=3.7 Hz), 112.1, 108.2 (q, J=4.4 Hz), 39.3 (q, J=26.8 Hz), 36.8, 33.9, 32.8, 31.5 (q, J=3.0 Hz), 25.8, 25.8; $^{19}$F NMR (376 MHz, CDCl$_3$) δ=−60.60 (s, 3F), −64.35 (t, J=10.4 Hz, 3F). m/z (ESI) 432.1 [M+H$^+$].

Biological Studies

Cannabinoid (CB) Receptor Allosteric Modulators—Functional Characteristics

Cannabinoid receptor allosteric ligands may be functionally characterised, for example, according to:

(1) their effect upon agonist binding; and/or
(2) their effect upon agonist-induced signalling efficacy.

For example, allosteric interactions at the cannabinoid CB1 receptor have recently been described (see, e.g., Price et al., 2005). Three compounds, ORG27569, ORG29647 and ORG27759, produce a slowing of the dissociation of radiolabelled CB1receptor agonist CP55940 from the CB1 receptor in mouse brain membranes. This slowing of the dissociation of the agonist is indicative of an allosteric modulator (see, e.g., Price et al, 2005). These three ORG compounds also induce an increase in the binding of CP55940 in an equilibrium binding assay and a decrease in the binding of a radiolabelled inverse agonist SR141716A. Thus, these modulators display a markedly divergent effect on orthosteric ligand affinity versus efficacy; they are allosteric enhancers of agonist binding affinity and allosteric inhibitors of agonist signalling efficacy.

Irrespective of mechanism, ligands can be classified solely on their overall functional effects: ligands which amplify the effect of an agonist are known as allosteric enhancers or positive allosteric modulators; ligands which suppress the effect of an agonist are known as allosteric inhibitors or negative allosteric modulators.

Assays Used to Investigate Allosteric Modulation

In order to fully investigate the effects of allosteric modulators, it is important to investigate the effects on both agonist affinity and efficacy.

The radioligand equilibrium binding assay can be used to determine the effects on binding. When an allosteric ligand binds, it can either increase or decrease the dissociation rates of radiolabelled ligands. The use of functional assays to find allosteric modulators is also widely used as a screening mechanism and is required in order to define the overall modulatory effect, positive or negative. It is possible to find allosteric modulators that affect signalling but don't affect affinity, which could be missed using the radioligand binding assays (equilibrium and dissociation) (see, e.g., Christopolous et al., 2004). Functional assays such as the β-arrestin recruitment assay represent an excellent starting point for G-protein coupled receptor based drug discovery where the main purpose of drug discovery is to find compounds that exert functional effects.

Binding Assays

Radioligand equilibrium binding assays are used to investigate whether or not the compound under investigation has an effect on the affinity of the orthosteric ligand binding. When an allosteric ligand binds, it can either increase or decrease the dissociation rates of radiolabelled ligands. Using this method to look for allosteric modulators of orthosteric agonist affinity can be advantageous. If the modulator has an allosteric effect on the affinity of an orthosteric agonist for its receptor, there may be a displacement (full or partial), no displacement, or even an enhancement of orthosteric ligand binding. However, orthosteric and allosteric ligands share the ability to appear to fully "displace" an orthosteric ligand in an equilibrium binding assay. When a compound appears to "fully displace" the orthosteric ligand, it might be assumed it is acting at the orthosteric site but it may be acting at the allosteric site. This assay is useful in determining the effect the allosteric compound has on the affinity of the orthosteric compound. However, it is normally used along with another assay in order to correctly identify and confirm an allosteric action and prevent misidentification. This is often an important step in a full characterisation of an allosteric modulator, particularly those modulators which affect orthosteric binding affinity or of those that differentially affect orthosteric functional efficacy (see, e.g., Price et al., 2005).

Functional Assays

Functional assays are used to find allosteric modulators, and are also widely used as a screening mechanism and are required in order to define the overall modulatory effect, positive or negative. It is possible to identify allosteric modulators that affect signalling but don't affect affinity, and which could be missed using only a radioligand binding assay (equilibrium and dissociation) (see, e.g., Christopolous et al., 2004).

Negative allosteric modulators will cause a characteristic decrease in efficacy ($E_{max}$) of an orthosteric agonist in a functional assay. In contrast, competitive antagonists cause no change in agonist efficacy, but do cause a decrease in the potency ($EC_{50}$). Positive allosteric modulators will show a characteristic increase in the efficacy ($E_{max}$) of the orthosteric agonist.

PathHunter™ β-Arrestin Assays

β-Arrestins are multifunctional intracellular proteins that interact with a structurally diverse group of cell surface receptors including GPCRs, to regulate cellular functions (see, e.g., Violin and Lefkowitz, 2007).

PathHunter™ enzyme fragment complementation is the most important method to measure β-arrestin recruitment. PathHunter™ β-Arrestin assays developed by DiscoveRX are revolutionary high-throughput screening assays for monitoring GPCR activation following ligand stimulation, without an imaging instrument, fluorescent protein tag, or radioactivity.

Instead, the assays detect GPCR activation through binding of β-arrestin to the expressed GPCR of interest, and measure the interaction of the two proteins using enzyme fragment complementation (EFC). The EFC approach offers a range of benefits for screening; including signal amplification and robust performance.

In this assay, the β-galactosidase enzyme (β-gal) is split into two inactive fragments. The larger portion of β-gal, termed EA for enzyme acceptor, is fused to the C-terminus of β-arrestin. The smaller, complementing fragment of β-gal, the ProLink™ tag, is expressed as a fusion protein with the GPCR of interest at the C-terminus. Upon activation, the GPCR is bound by β-arrestin. The interaction of β-arrestin and the GPCR forces the interaction of ProLink and EA, thus allowing complementation of the two fragments of β-gal and the formation of a functional enzyme capable of hydrolyzing substrate and generating a fluorescence signal.

Using the PathHunter™ CB1 kit from DiscoveRX, a cannabinoid CB1 receptor agonist is added and activates the receptor, EA, which is fused to the C-terminus of β-arrestin, and then interacts with the ProLink™ tag which is fused to the CB1 receptor. This will result in the fluorescence signal that is recorded by a luminescence plate reader. The fluorescence signal is directly related to the activation of the receptor, therefore a higher concentration of agonist will yield a larger fluorescence signal. The cannabinoid agonist is added in increasing concentrations to obtain an agonist dose response curve. With pre-incubation of a potential allosteric modulator, either an enhancement of agonist signalling with an allosteric enhancer or a decrease in the maximal response of the agonist with an allosteric inhibitor is expected.

All raw data are obtained as luminescence (relative light units), and are normalised and presented as a percentage of the maximal response for the endogenous cannabinoid CB1 receptor agonist anandamide (N-arachidonoyletha-nolamine).

[$^{35}$S]GTPγS Binding Assay

The [$^{35}$S]GTPγS binding assay was initially used and characterized with purified receptor and G-protein complexes in phospholipid vesicles using β-adrenergic receptors (see, e.g., Asano et al., 1984). It is now common for this assay to be done using cell membranes that possess the receptor of interest (see, e.g., Harrison et al., 2003).

All G-protein coupled receptors must function through an interaction and activation of G-proteins (see, e.g., Milligan, 2003). The [$^{35}$S]GTPγS binding assay measures the amount of G-protein activation after a ligand binds to the G-protein coupled receptor (see, e.g., Harrison et al., 2003). In its inactive state, the G-protein exists as a heterodimer (Gα (GDP)βγ) with GDP bound to the Gα subunit. When the G-protein is activated by a ligand binding to the receptor, there is an exchange of GDP to GTP at the Gα subunit; this is known as the guanine nucleotide exchange (see, e.g., Harrison et al., 2003). This binding of the GTP to the Gα subunit leads to the dissociation of the βγ subunit, which will in turn lead to the downstream effects exerted by the activation of the particular G-protein (see, e.g., Milligan, 2003). The Gα(GDP)βγ heterodimer is then reformed by GTPase which reforms the Gα to GDP which then leads to the binding of the βγ complex (see, e.g., Harrison et al., 2003). The guanine nucleotide exchange is an event that happens very early in the signal transduction cascade, making this assay an excellent measure of pharmacological characteristics and the efficacy of ligands binding to the receptor (see, e.g., Milligan, 2003).

[$^{35}$S]GTPγS is an analogue of GTP; it is non-hydrolysable and therefore resistant to the GTPase activity of the Gα subunit. In the [$^{35}$S]GTPγS binding assay, [$^{35}$S]GTPγS is used to replace the naturally occurring GTP. As this analogue is not hydrolysed by the GTPase, the GDP is not then able to reassociate with the Gα subunit, meaning that there will then be a build-up of membrane bound [$^{35}$S]GTPγS (see, e.g., Milligan, 2003). The amount of [$^{35}$S]GTPγS bound is then quantified through filtration onto fibre glass filters which will retain any radioactivity. These filters are then used in a liquid scintillation counter. The data collected are expressed as a percentage over the amount of basal binding.

Human and Rat Liver Microsomal Stability Assay

The metabolic stability of the compounds of the Formula (I) was measured by determination of the rate of compound disappearance when incubated in the presence of both human and rat liver microsomes. Liver microsomes are prepared from the endoplasmic reticulum of hepatocytes and are the primary source of the most important enzymes (cytochrome P450) involved in drug metabolism. Study of drug stability in the presence of liver microsomes is accepted as a valuable model permitting rapid prediction of in vivo drug stability.

Protocol Summary

Human and rat liver microsomes were obtained from a commercial source. Test compounds (3 µM) were incubated with pooled liver microsomes (male and female). Samples were incubated for a 45 minute period and removed at 5 time points and test compounds were analysed by LC-MS/MS.

Microsomes (final protein concentration 0.5 mg/mL), 0.1 M phosphate buffer pH 7.4, and test compound (final concentration 3 µM; diluted from 10 mM stock solution to give a final DMSO concentration of 0.25%) were incubated at 37° C. prior to the addition of NADPH (final concentration 1 mM) to initiate the reaction. The final incubation volume was 25 µL. A control incubation was included for each compound tested, where 0.1 M phosphate buffer pH 7.4 was added instead of NADPH. The control compounds testosterone and 7-hydroxycoumarin were included in each experiment and all incubations were performed singularly for each compound.

Each compound was incubated for 0, 5, 15, 30, and 45 minutes. The control (minus NADPH) was incubated for 45 minutes only. The reactions were stopped by the addition of 50 µL methanol containing internal standard at the appropriate time points. The incubation plates were centrifuged at 2500 rpm for 20 minutes at 4° C. to precipitate the protein.

Quantitative Analysis:

Following protein precipitation, the sample supernatants were combined in cassettes of up to 4 compounds and analysed using standard LC-MS/MS conditions.

Data Analysis:

From a plot of the natural logarithm of the peak area ratio (i.e., the ratio of compound peak area:internal standard peak area) against time, the gradient of the line was determined. Subsequently, half-life and intrinsic clearance were calculated using the equations below:

Eliminated Rate Constant $(k)$=$(-$Gradient$)$.

Half-Life $(t_{1/2})$(min)=0.063/$k$.

Intrinsic Clearance $(CL_{int})$(µL/min/million cells)= $(V \times 0.693)/t_{1/2}$.

wherein V=Incubation Volume (µL/mg microsomal protein).

Biological Study 1

Initial screening of candidate compounds was performed using an in vitro assay to determine functional characteristics.

The PathHunter™ β-Arrestin assay (from DiscoveRX, Fremont, USA) was performed as follows. HEK293 CB1 β-arrestin cells were plated 48 hours before use and incubated at 37° C., 5% $CO_2$ in a humidified incubator. Test compounds were dissolved in dimethylsulfoxide (DMSO) and diluted in optimized cell culture media (OCC, as supplied by DiscoveRX) media to the required concentrations. 5 µL of test compound or vehicle solution was added to each well and incubated for 60 minutes at 37° C., 5% $CO_2$ in a humidified incubator. 5 µL of increasing concentrations of anandamide was added to each well followed by a 90 minute incubation at 37° C., 5% $CO_2$ in a humidified incubator. 55 µL of detection reagent (as supplied by DiscoveRX) was then added, followed by a further 90 minute incubation at room temperature in the dark. Chemiluminescence, reported in relative light units (RLU—a dimensionless value, standardised as a % of maximum stimulation with anandamide), was measured on a standard luminescence plate reader.

Data were plotted as % of maximal stimulation ($E_{max}$) caused by agonist versus the logarithm of concentration of agonist, in the presence or absence of a fixed concentration of test compound (modulator) or vehicle. For example, stimulation in the presence of agonist alone will give a value for stimulation expressed in RLU, which can be expressed as a range from 0% (at lowest agonist concentration, e.g., 1 nM) to 100% (at the highest agonist concentration, e.g., 10 µM). Addition of a test compound which is a positive allosteric modulator at a fixed concentration (e.g., 100 nM) will give increased RLU values leading to an increase in the maximum stimulation elicited by the agonist, which can be expressed as a % of the control (agonist alone). The percentage increase above the $E_{max}$ value will be represented for positive allosteric modulators.

Biological Data

Biological Study 1

The biological activity of a number of compounds of the Formula (I) was determined using the assays described previously.

The maximum % increase in the stimulation caused by the endogenous cannabinoid agonist anandamide were determined for range of concentrations of several NN-PAM compounds, and compared to values for nitro-bearing PAM compounds and other compounds with other bioisosteres of the nitro-group, using the β-arrestin assay described above. The results are summarised in Table 2.

The data in Table 2 demonstrate that it is possible to substitute the nitro group found in F-0870-0064, ZCZ011 and ABD999 with a select range of bioisosteres. However, the data also demonstrates that the obvious bioisosteric replacements for a nitro group do not give compounds with activity as CB1 positive allosteric modulators. Furthermore, the above data demonstrates the activity of compounds having substitution at the indole-6-position. In each case this gives a considerable increase in potency, converting a compound with activity only at 1000 nM, to a compound with activity at 100 or 300 nM.

Biological Study 2

The metabolic stability of a number of compounds of the Formula (I) was determined and compared with the metabolic stability of the parent nitro PAM compounds, using the assays described above.

Biological half-life values ($t_{1/2}$) were determined for several NN-PAM compounds, as well as perhexiline itself, using the human liver microsomal (HLM) and rat liver microsomal (RLM) stability assays described above. The results are summarized in the following Table 3.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 2

Increase in the stimulation caused by compounds of the Formula (I)

| Compound | Structure | Potency % Enhancement | | |
|---|---|---|---|---|
| | | 100 nM | 300 nM | 1000 nM |
| ZCZ011 (Prior art) | | 56.8 | — | 126.0 |
| ABD999 | 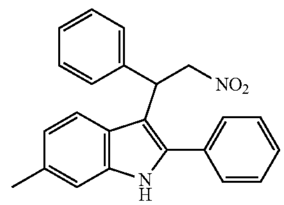 [SMILES: Cc1ccc2c(C(C[N+](=O)[O-])c3ccccc3)c(-c3ccccc3)[nH]c2c1] | — | — | 76.8 |
| ABD1003 | 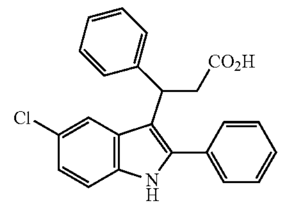 [SMILES: O=C(O)CC(c1ccccc1)c1c(-c2ccccc2)[nH]c2ccc(Cl)cc12] | — | — | 0 |
| ABD1009a | 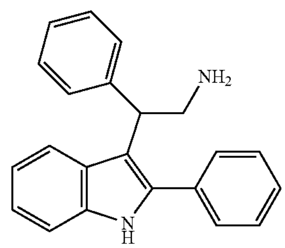 [SMILES: NCC(c1ccccc1)c1c(-c2ccccc2)[nH]c2ccccc12] | — | — | 0 |
| ABD1009 | 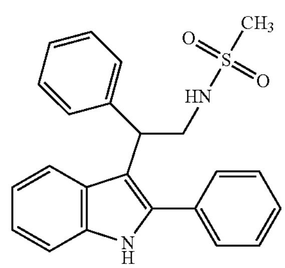 [SMILES: CS(=O)(=O)NCC(c1ccccc1)c1c(-c2ccccc2)[nH]c2ccccc12] | — | — | 0 |
| ABD1011 | 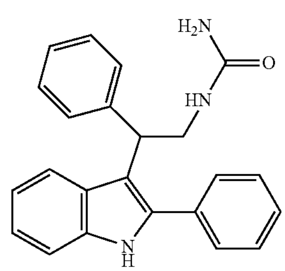 [SMILES: NC(=O)NCC(c1ccccc1)c1c(-c2ccccc2)[nH]c2ccccc12] | — | — | 0 |
| ABD1077 | 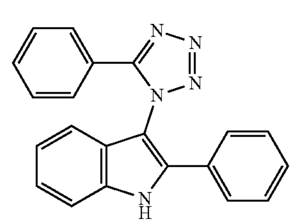 [SMILES: c1ccc(-c2[nH]c3ccccc3c2-n2nnnc2-c2ccccc2)cc1] | — | — | 0 |

TABLE 2-continued

Increase in the stimulation caused by compounds of the Formula (I)

| Compound | Structure | Potency % Enhancement | | |
|---|---|---|---|---|
| | | 100 nM | 300 nM | 1000 nM |
| ABD1078 | | — | — | 0 |
| ABD1097 | | — | — | 0 |
| ABD1098 | | — | — | 0 |
| ABD1101a | | — | — | 0 |
| ABD1101b | | — | — | 0 |
| ABD1105 | | — | — | 0 |
| ABD1106 | | — | — | 0 |
| ABD1117 | | — | — | 0 |
| ABD1131 | | — | — | 0 |
| ABD1100 | | — | 0 | 19.6 |
| ABD1102 | | — | 0 | 21.9 |
| ABD1132 | | — | 21.6 | 80.6 |

TABLE 2-continued

Increase in the stimulation caused by compounds of the Formula (I)

| Compound | Structure | Potency % Enhancement | | |
|---|---|---|---|---|
| | | 100 nM | 300 nM | 1000 nM |
| ABD1133 | 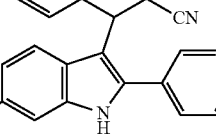 | — | 68.7 | 40.4 |
| ABD1137 | 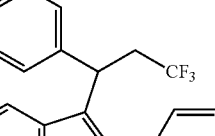 | — | 0 | 20.7 |
| ABD1139 | 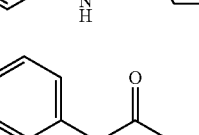 | — | 0 | 18.6 |

TABLE 2-continued

Increase in the stimulation caused by compounds of the Formula (I)

| Compound | Structure | Potency % Enhancement | | |
|---|---|---|---|---|
| | | 100 nM | 300 nM | 1000 nM |
| ABD1145 | 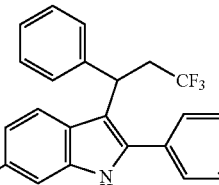 | 45.5 | — | 61.9 |
| ABD1146 | 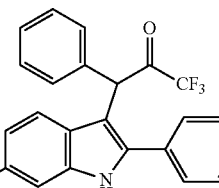 | 34.0 | — | 81.0 |
| ABD1155 | 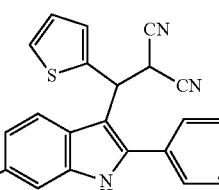 | — | — | 67.4 |

TABLE 3

Half-life values of compounds of the Formula (I)

| Compound | Structure | $CL_{int}$ (μL/min/mg protein) HLM | $T_{1/2}$ (min) HLM | $CL_{int}$ (μL/min/mg protein) RLM | $T_{1/2}$ (min) RLM |
|---|---|---|---|---|---|
| ZCZ011 (Prior art) | 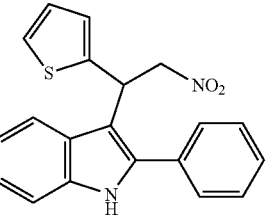 | 37.8 | 36.7 | 127 | 8.1 |
| ABD999 | 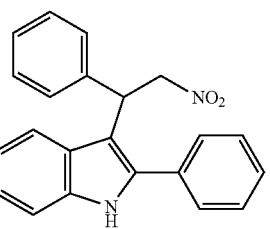 | 29.1 | 47.7 | — | — |

TABLE 3-continued

| | Half-life values of compounds of the Formula (I) | | | | |
|---|---|---|---|---|---|
| Compound | Structure | $CL_{int}$ (μL/min/mg protein) HLM | $T_{1/2}$ (min) HLM | $CL_{int}$ (μL/min/mg protein) RLM | $T_{1/2}$ (min) RLM |
| ABD1100 | | 52.9 | 26.2 | 93.7 | 14.8 |
| ABD1102 | | 32.4 | 42.7 | 95.4 | 14.5 |
| ABD1132 | | 30.3 | 45.7 | 74.0 | 18.7 |
| ABD1133 | | 35.2 | 39.3 | 112.0 | 12.4 |
| ABD1137 | | 16.3 | 85.2 | 34.0 | 40.7 |
| ABD1139 | | 27.1 | 51.1 | 33.5 | 41.4 |

TABLE 3-continued

| | Half-life values of compounds of the Formula (I) | | | | |
|---|---|---|---|---|---|
| Compound | Structure | CL$_{int}$ (μL/min/mg protein) HLM | T$_{1/2}$ (min) HLM | CL$_{int}$ (μL/min/mg protein) RLM | T$_{1/2}$ (min) RLM |
| ABD1145 | | 16.9 | 87.2 | 49.2 | 28.2 |
| ABD1146 | | 5.2 | 267 | 55.8 | 24.8 |
| ABD1156 | | 18.6 | 74.4 | 70.1 | 19.8 |
| ABD1187 | | 5.0 | 108 | 79.3 | 17.5 |
| ABD1188 | | 23.4 | 59.1 | 134 | 10.3 |
| ABD1216 | | 21.7 | 63.9 | 29.9 | 46.3 |

TABLE 3-continued

Half-life values of compounds of the Formula (I)

| Compound | Structure | $CL_{int}$ (µL/min/mg protein) HLM | $T_{1/2}$ (min) HLM | $CL_{int}$ (µL/min/mg protein) RLM | $T_{1/2}$ (min) RLM |
|---|---|---|---|---|---|
| ABD1217 | [6-chloro-3-(1-(thiophen-2-yl)-2-(trifluoromethyl)ethyl)-2-phenyl-1H-indole] | 8.8 | 157 | 25.5 | 54.3 |
| ABD1218 | [6-chloro-3-(1-phenyl-2-(trifluoromethyl)ethyl)-2-phenyl-1H-indole] | 14.1 | 98.6 | 17.8 | 78.0 |

REFERENCES

Adam et al., 2007, "Positive allosteric modulators of CB1 receptors." Symposium on the Cannabinoids. Burlington, Vt., USA. International Cannabinoid Research Society, p. 86.

Adam et al., 2012, "Low brain penetrant CB1 receptor agonists for the treatment of neuropathic pain," Bioorg. Med. Chem. Lett., Vol. 22, pp. 2932-2937

Asano et al., 1984, "Reconstitution of catecholamine-stimulated binding of Guanosine 5'-O-(3-Thiotriphosphate) to the stimulatory GTP-binding protein of adenylate cyclase." Biochemistry, Vol. 23, pp. 5460-5467

Babu et al., 2008, "Mild and Efficient Michael Addition of Activated Olefins to Indoles using TBAB as a Catalyst: Synthesis of 3-Substituted Indoles," Synthetic Communications: An International Journal for Rapid Communication of Synthetic Organic Chemistry, Vol. 38, pp. 1784-1791.

Baell and Holloway, 2010, "New Substructure Filters for Removal of Pan Assay Interference Compounds (PAINS) from Screening Libraries and for Their Exclusion in Bioassays," J. Med. Chem., Vol, 53, pp. 2719-2740.

Bailie et al., "In vitro effects of ZCZ011: A Positive Allosteric Modulator of the CB1 Receptor," 23rd Annual Symposium of the International Cannabinoid Reach Society, Vancouver British Columbia Canada Jun. 21, 2013. (abstract p13)

Bandini et al., 2002, "A Practical Indium Tribromide Catalysed Addition of Indoles to Nitroalkenes in Aqueous Media," Synthesis, pp. 1110-1114

Bensaid et al., 2003, "The cannabinoid CB1 receptor antagonist SR141716 increases Acrp30 mRNA expression in adipose tissue of obese fa/fa rats and in cultured adipocyte cells," Mol. Pharmacol., Vol. 63, pp. 908-914.

Bermúdez-Silva et al., 2008, "Presence of functional cannabinoid receptors in human endocrine pancreas," Diabetologia, Vol. 51, pp. 476-487.

Christopoulos et al., 2002, "G protein-coupled receptor allosterism and complexing," Pharmacol. Rev., Vol. 54, pp. 323-374.

Conn et al., 2009, "Allosteric modulators of GPCRs: a novel approach for the treatment of CNS disorders," Nat. Rev. Drug Disc., Vol. 8, pp. 41-54 (January 2009).

Cota et al., 2003, "The endogenous cannabinoid system affects energy balance via central orexigenic drive and peripheral lipogenesis," J. Clin. Invest., Vol. 112, pp. 423-431.

Cravatt et al., 2004, "The endogenous cannabinoid system and its role in nociceptive behaviour," J. Neurobiol., Vol. 61, pp. 149-160.

Croci et al., 2003, "Role of cannabinoid CB1 receptors and tumor necrosis factor-alpha in the gut and systemic anti-inflammatory activity of SR 141716 (rimonabant) in rodents," Brit. J. Pharmacol., Vol. 140, pp. 115-122.

Crowe et al., 2014, "The endocannabinoid system modulates stress, emotionality, and inflammation," Brain Behav. Immun., in press.

Di Marzo et al., 2004, "The endocannabinoid system and its therapeutic exploitation," Nat. Rev. Drug Disc., Vol. 3, pp. 771-784.

Di Marzo, 2008, "Targeting the endocannabinoid system: to enhance or reduce?" Nat. Rev. Drug Disc., Vol. 7, pp. 438-455.

Gao et al., 2006, "Keynote review: Allosterism in membrane receptors," Drug Disc. Today, Vol. 11, pp. 191-202.

Greig et al., 2004, international patent application publication number WO 2004/078261 A1 published 16 Sep. 2004.

Gu et al., 2008, "Glycerol as An Efficient Promoting Medium for Organic Reactions," Adv. Synth. Catal., 2008, Vol. 350, pp. 2007-2012.

Guindon et al., 2007, "The antinociceptive effects of intraplantar injections of 2-Arachidonoylglycerol are mediated by cannabinoid CB2 receptors," Br. J. Pharmacol., Vol. 150, pp. 693-701.

Guo et al., 2010, "Enantioselective Oxidative Cross-Coupling Reaction of 3-Indolylmethyl C—H Bonds with 1,3-Dicarbonyls Using a Chiral Lewis Acid-Bonded Nucleophile to Control Stereochemistry," *Angewandte Chemie—Int. Ed.*, Vol. 49, pp. 5558-5562.

Habib et al., 2008, "Catalyst-free aqueous-mediated conjugative addition of indoles to β-nitrostyrenes," *Tet. Lett.* Vol. 49, pp. 7005-7007.

Habib et al., 2010, "Catalyst free conjugate addition of indoles and pyrroles to nitro alkenes under solvent free condition (SFC): an effective greener route to access 3-(2-nitro-1-phenylethyl)-1H-indole and 2-(2-nitro-1-phenylethyl)-1H-pyrrole derivatives," *Tetrahedron*, Vol. 66, pp. 7050-7056.

Harrison and Traynor, 2003, "The [$^{35}$S]GTPγS binding assay: approaches and applications in pharmacology," *Life Sciences*, Vol. 74, pp 489-508.

Idris et al., 2005, "Regulation of bone mass, bone loss and osteoclast function by cannabinoid receptors", *Nat. Med.*, Vol. 11, pp. 774-779.

Ignatowska-Jankowska et al., 2013, "In vivo effects of ZCZ011: A Positive Allosteric Modulator of the CB1 Receptor," 23rd Annual Symposium of the International Cannabinoid Reach Society, Vancouver British Columbia Canada Jun. 21, 2013. (abstract p14).

Ignatowska-Jankowska et al., 2015, "A CB1 Receptor Positive Allosteric Modulator Reduces Neuropathic Pain in the Mouse with no Psychoactive Effects. Neuropsychopharmacology." epub ahead of print Jun. 8, 2015.

Kelly and Kim, 1994, "Relative Binding Affinity of Carboxylate and Its Isosteres: Nitro, Phosphate, Phosphonate, Sulfonate, and δ-Lactone." *J. Am. Chem. Soc.*, Vol. 116, pp. 7072-7080.

Kumar et al., 2008, "Friedel-Crafts alkylation of indoles with nitroolefins in the presence of β-cyclodextrin in water under neutral conditions," *Can. J. Chem.*, Vol. 86, pp. 907-911

Kuo et al., 2009, "An Efficient Method for the N-Bromosuccinimide Catalyzed Synthesis of Indolyl-Nitroalkanes," *Molecules*, Vol. 14, pp. 3952-3963.

Kunos et al., 2009, "Should peripheral CB(1) cannabinoid receptors be selectively targeted for therapeutic gain?" *Trends Pharmacol. Sci.*, Vol. 30, pp. 1-7.

Lynch and Campbell, 2011, "Cannabinoids for treatment of chronic non-cancer pain; a systematic review of randomized trials," *Br. J. Clin. Pharmacol.*, Vol. 72, pp. 735-44.

May et al., 2003, "Allosteric modulators of G-protein-coupled receptors," *Curr. Opin. Pharmacol.*, Vol. 3, pp. 551-556.

Meanwell, 2011, Synopsis of Some Recent Tactical Application of Bioisosteres in Drug Design, *J. Med. Chem.*, Vol. 54, pp. 2529-2591

Mechoulam and Parker, 2012, "The Endocannabinoid System and the Brain," *Annu. Rev. Psychol.*, Vol. 64, pp. 21-47.

Milligan, 2003. "Principles: extending the utility of [$^{35}$S] GTPγS binding assays." *TRENDS in Pharmacological Sciences* Vol. 24, pp. 87-90

Muegge et al., 2001, "Simple Selection Criteria for Drug-like Chemical Matter," *J. Med. Chem.*, Vol. 44, pp. 1841-6.

Noland and Lange, 1959, "The Nitroethylation of Indoles. III.1-3 A Synthetic Route to Substituted Tryptamines," *J. Amer. Chem. Soc.*, Vol. 81, pp. 1203-1209

Osei-Hyiaman et al., 2005, "Endocannabinoid activation at hepatic CB1 receptors stimulates fatty acid synthesis and contributes to diet-induced obesity," *J. Clin. Invest.*, Vol. 115, pp. 1298-1305.

Pacher et al., 2006, "The Endocannabinoid System as an Emerging Target of Pharmacotherapy," *Pharmacol. Rev.*, Vol. 58, pp. 389-462

Parolaro et al., 2010, "The endocannabinoid system and psychiatric disorders," *Experimental Neurology*, Vol. 224, pp. 3-14.

Patti, 2010, "Rehashing endocannabinoid antagonists: can we selectively target the periphery to safely treat obesity and type 2 diabetes?", *J. Clin. Invest.*, Vol. 120, pp. 2646-2648.

Pertwee, 2005, "The Therapeutic potential of drugs that target cannabinoid receptors or modulate the tissue levels or actions of endocannabinoids," *AAPS Journal*, Vol. 7, pp. E625-E654.

Pertwee, 2007, "Cannabinoids and multiple sclerosis," *Mol. Neurobiol.*, Vol. 36, pp. 45-59.

Pertwee, 2009, "Emerging strategies for exploiting cannabinoid receptor agonists as medicines," *Br. J. Pharmacol.*, Vol. 156, pp. 397-411

Pertwee, 2012, "Targeting the endocannabinoid system with cannabinoid receptor agonists: pharmacological strategies and therapeutic possibilities," *Phil. Trans. R. Soc.*, Vol. 367, pp. 3353-3363.

Piomelli et al., 2006, "Pharmacological profile of the selective FAAH inhibitor KDS-4103 (URB597)," *CNS Drug Reviews*, Vol. 12, pp. 1-38.

Price et al., 2005, "Allosteric Modulation of the Cannabinoid CB1 Receptor, *Mol. Pharmacol.*, Vol. 68, pp. 1484-1495.

Qu et al., 2011, "Synthesis of 3-indole derivatives by copper sulfonato Salen catalysed three-component reactions in water." *Chem. Commun.*, Vol. 47, pp. 3912-3914

Rees et al., 2002, "GPCR drug discovery through the exploitation of allosteric drug binding sites," *Receptors and Channels*, Vol. 8, pp. 261-268.

Ross, 2003, "Anandamide and Vanilloid TRPV1 Receptors," *Br. J. Pharmacol.*, Vol 140, pp. 790-801.

Ross, 2007, "Allosterism and cannabinoid CB(1) receptors: the shape of things to come," *Trends Pharmacol. Sci.*, Vol. 28, pp. 567-572.

Ryberg et al., 2007, "The orphan receptor GPR55 is a novel cannabinoid receptor," *Br. J. Pharmacol.*, Vol. 152, pp. 1092-1101.

Rydzewski, 2008, Real World Drug Discovery, Elsevier Press pp. 461-2.

Scheen et al., 2006, "Efficacy and tolerability of rimonabant in overweight or obese patients with type 2 diabetes: a randomised controlled study," *Lancet*, Vol. 368, pp. 1660-1672.

Seierstad and Breitenbucher, 2008, "Discovery and development of fatty acid amide hydrolase (FAAH) inhibitors.", *J. Med. Chem.*, Vol. 51, pp. 7327-7343

Son et al., 2010, "Peripherally acting CB1-receptor antagonist: the relative importance of central and peripheral CB1 receptors in adiposity control," *Int. J. Obesity*, Vol. 34, pp. 547-556.

Soudijn et al., 2004, "Allosteric modulation of G protein-coupled receptors: perspectives and recent developments," *Drug Disc. Today*, Vol. 9, pp. 752-758.

Talwar and Potluri, 2011, "Cannabinoid 1 (CB1) receptor-pharmacology, role in pain and recent developments in emerging CB1 agonists," *CNS Neurol. Disord. Drug Targets*, Vol. 10, pp. 536-44.

Tam et al., 2010, "Peripheral CB1 cannabinoid receptor blockade improves cardiometabolic risk in mouse models of obesity," *J. Clin. Invest.*, Vol. 120, pp. 2953-2966.

Thakur and Kulkarni, 2013, "Allosteric Modulators of CB1 Cannabinoid Receptors," international patent application publication number WO WO2013/103967 A1 published 11 Jul. 2013

Violin and Lefkowitz, 2007, "Beta-arrestin-biased ligands at seven-transmembrane receptors," *Trends Pharmacol. Sci.*, Vol. 28, pp. 416-22.

Wadman, 2006, "Rimonabant adds appetizing choice to slim obesity market," *Nat. Med.*, Vol. 12, p. 27.

Wang et al., 2009, "Allosteric modulators of G protein-coupled receptors: future therapeutics for complex physiological disorders," *J. Pharmacol. Exp. Ther.*, Vol. 331, pp. 340-348.

Wu et al., Zhuang et al., (2001), "Catalytic enantioselective alkylation of heteroaromatic compounds using alkylidene malonates," *Chem. Commun.*, pp. 347-8.

The invention claimed is:

1. A compound of the Formula (I)

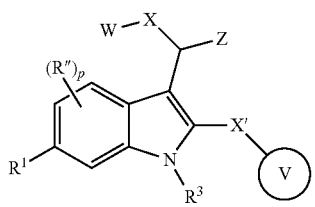

(I)

wherein,
W is $(C_1-C_{10})$-alkyl, $(C_3-C_{10})$-cycloalkyl, $(C_3-C_{10})$-heterocycloalkyl, $(C_6-C_{10})$-aryl, or $(C_5-C_{10})$-heteroaryl, each of which is optionally substituted with one or more of halo, —$CF_3$, —$OCF_3$, —CN, —$NO_2$, —R, —OR, —SR, —$NR_2$, —$NR'_2$, —C(=O)R, —C(=O)OR, —NRC(=O)R, —C(=O)$NR_2$, —C(=O)$NR'_2$, —S(=O)$_2NR_2$, —S(=O)$_2NR'_2$, —NRS(=O)$_2$R, —S(=O)$_2$R or —S(=O)$CF_3$,
wherein R is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl, and
R' is independently or simultaneously H, azetidino, pyrrolidino, piperidino, piperazino, morpholino, azepano, or diazepano;
X and X' are independently or simultaneously $(C_0-C_4)$-alkylene, optionally substituted with one or more of halo, —$CF_3$, OH, $OCF_3$, or —O—$(C_1-C_4)$alkyl;
Z is —$CH_2CF_3$ or —$C(=O)CF_3$;
Ring V is $(C_3-C_{10})$-cycloalkyl, $(C_3-C_{10})$-heterocycloalkyl, $(C_6-C_{10})$-aryl, or $(C_5-C_{10})$-heteroaryl, each of which is optionally substituted with one or more of the optional substituents defined in the variable W;
$R^1$ is halo, —$CF_3$, —$OCF_3$, —CN, —$NO_2$, —$R^2$, —$OR^2$, —SR, —$N(R^2)_2$, —$(NR^{2'})_2$, —C(=O)$R^2$, —C(=O)$OR^2$, —$NR^2$C(=O)$R^2$, —C(=O)$N(R^2)_2$, —C(=O)$N(R^{2'})_2$, —S(=O)$_2N(R^2)_2$, —S(=O)$_2N(R^{2'})_2$, —NRS(=O)$_2$R, —S(=O)$_2R^2$ or —S(=O)$CF_3$,
wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl, and
$R^{2'}$ is independently or simultaneously H, azetidino, pyrrolidino, piperidino, piperazino, morpholino, azepano, or diazepano;

$R^3$ is H or $(C_1-C_6)$alkyl;
R" is halo, —$CF_3$, —$OCF_3$, —CN, —$NO_2$, —$R^4$, —$OR^4$, —SR, —$N(R^4)_2$, —$(NR^{4'})_2$, —C(=O)$R^4$, —C(=O)$OR^4$, —$NR^4$C(=O)$R^4$, —C(=O)$N(R^4)_2$, —C(=O)$N(R^{4'})_2$, —S(=O)$_2N(R^4)_2$, —S(=O)$_2N(R^{4'})_2$, —$NR^4$S(=O)$_2R^4$, —S(=O)$_2R^4$ or —S(=O)$CF_3$,
wherein $R^4$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl, and
$R^{4'}$ is independently or simultaneously H, azetidino, pyrrolidino, piperidino, piperazino, morpholino, azepano, or diazepano;
p is the integer 0, 1, 2 or 3, and
pharmaceutically acceptable salts, stereoisomers, and/or solvates thereof.

2. The compound of the Formula (I) as claimed in claim 1, wherein W is $(C_1-C_6)$-alkyl, $(C_3-C_6)$-cycloalkyl, $(C_3-C_6)$-heterocycloalkyl, $(C_6)$-aryl, or $(C_5-C_6)$-heteroaryl, each of which is optionally substituted.

3. The compound of the Formula (I) as claimed in claim 1, wherein W is isopropyl, cyclopropyl, piperidine, tetrahydropyran, phenyl, thiophenyl, furanyl, pyridinyl, pyrimidinyl or pyrazinyl, each of which is optionally substituted.

4. The compound of the Formula (I) as claimed in claim 1, wherein W is phenyl, furanyl, cyclopropyl or thiophenyl, each of which is optionally substituted.

5. The compound of the Formula (I) as claimed claim 1, wherein the optional substituents on W are one or more of halo, —$CF_3$, —$OCF_3$, —CN, —R, or —OR.

6. The compound of the Formula (I) as claimed in claim 1, wherein X and X' are independently or simultaneously $(C_0-C_2)$-alkylene.

7. The compound of the Formula (I) as claimed in claim 1, wherein Ring V is $(C_3-C_6)$-cycloalkyl, $(C_3-C_6)$-heterocycloalkyl, $(C_6)$-aryl, or $(C_5-C_6)$-heteroaryl, each of which is optionally substituted.

8. The compound of the Formula (I) as claimed in claim 1, wherein Ring V is cyclopropyl, cyclopentyl, piperidinyl, tetrahydropyranyl, phenyl, thiophenyl, furanyl, pyridinyl, pyrimidinyl or pyrazinyl, each of which is optionally substituted.

9. The compound of the Formula (I) as claimed in claim 8, wherein Ring V is phenyl or cyclopentyl, each of which is optionally substituted.

10. The compound of the Formula (I) as claimed in claim 1, wherein the optional substituents on Ring V are one or more of halo, —$CF_3$, —$OCF_3$, —CN, —R, or —OR.

11. The compound of the Formula (I) as claimed in claim 1, wherein $R^1$ is halo, —$CF_3$, —$OCF_3$, —CN, —$R^2$, —$OR^2$, —SR, or —$N(R^2)_2$, wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl.

12. The compound of the Formula (I) as claimed in claim 1, wherein $R^1$ is halo, 13$CF_3$, —$OCF_3$, —CN, or —$R^2$ wherein $R^2$ is independently or simultaneously H, $(C_1-C_6)$-alkyl, $(C_2-C_6)$-alkenyl, $(C_2-C_6)$-alkynyl, $(C_3-C_6)$-cycloalkyl, phenyl or benzyl.

13. The compound of the Formula (I) as claimed in claim 1, wherein $R^1$ is halo, —$CF_3$, or —$R^2$, wherein $R^2$ is independently or simultaneously H, $(C_1-C_3)$-alkyl, $(C_2-C_3)$-alkenyl, $(C_2-C_3)$-alkynyl, or $(C_3-C_6)$-cycloalkyl.

14. The compound of the Formula (I) as claimed in claim 13, wherein $R^1$ is Cl, —$CF_3$, or methyl.

15. The compound of the Formula (I) as claimed in claim 1, wherein the compound of the Formula (I) is
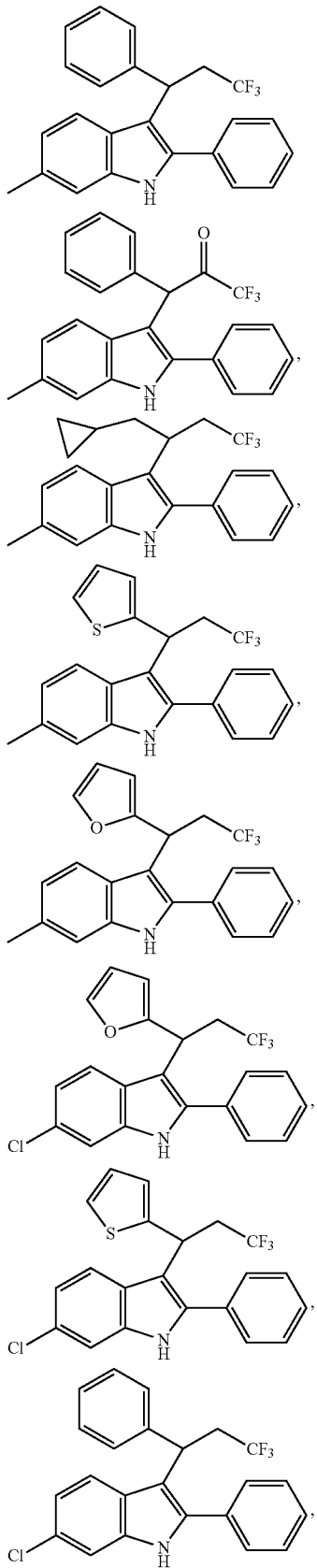
-continued
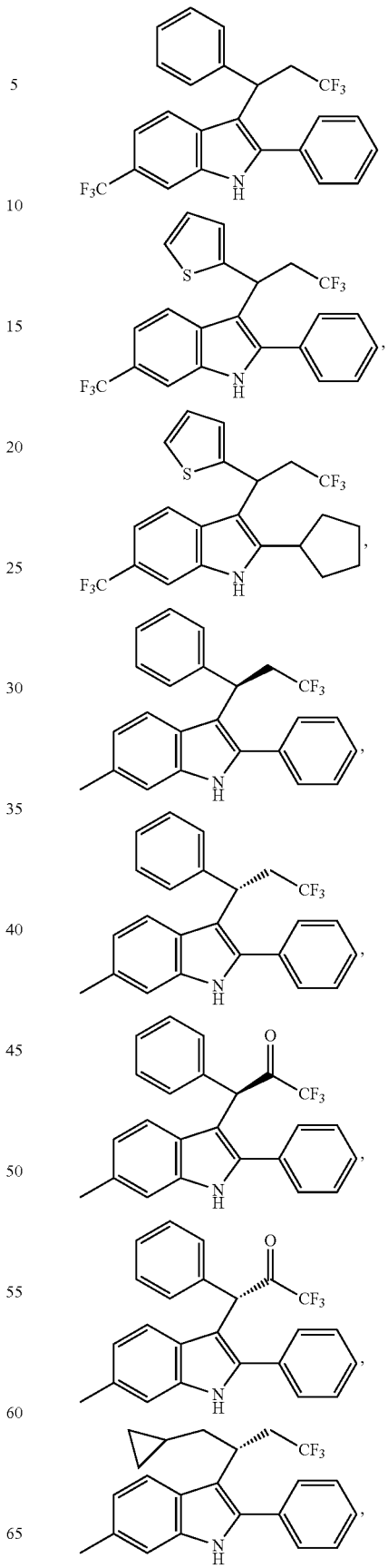

117
-continued
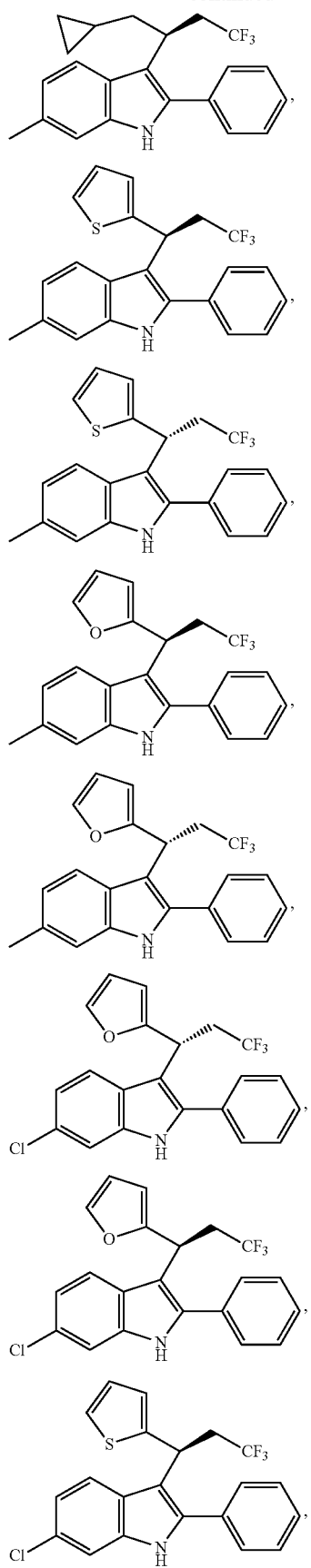
118
-continued
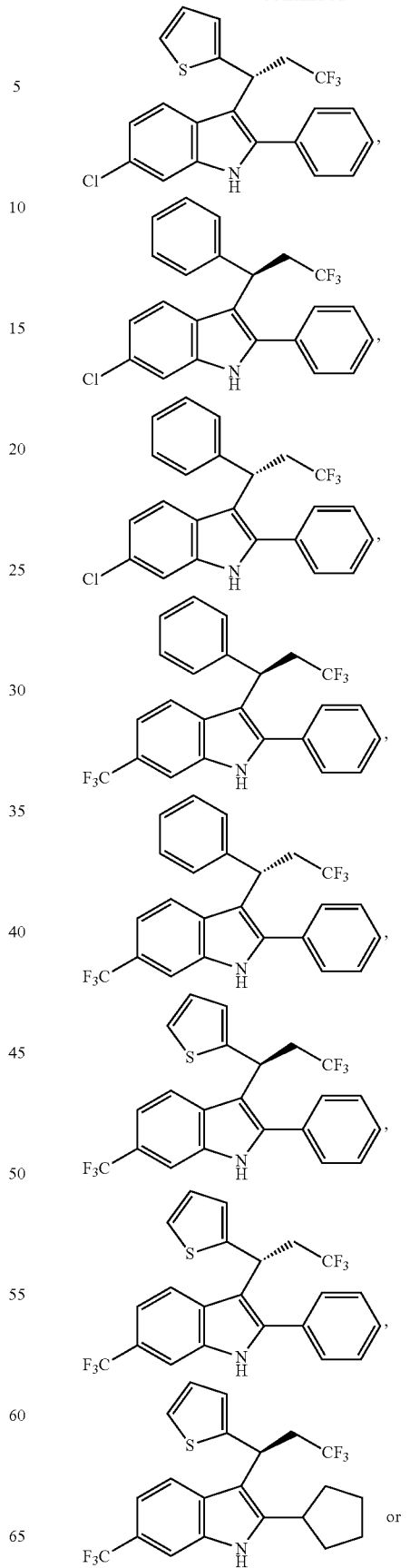

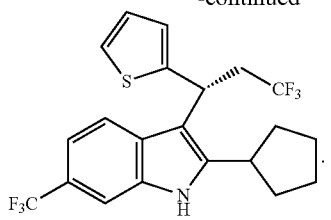
* * * * *

UNITED STATES PATENT AND TRADEMARK OFFICE
CERTIFICATE OF CORRECTION

PATENT NO. : 10,377,711 B2
APPLICATION NO. : 15/507079
DATED : August 13, 2019
INVENTOR(S) : Ross et al.

Page 1 of 1

It is certified that error appears in the above-identified patent and that said Letters Patent is hereby corrected as shown below:

In the Claims

In Column 114, Line 57, in Claim 12, delete "13CF$_3$," and insert -- -CF$_3$,-- therefor Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*